United States Patent
Diamond et al.

(10) Patent No.: US 10,376,575 B2
(45) Date of Patent: *Aug. 13, 2019

(54) MVA VACCINE FOR DELIVERY OF A UL128 COMPLEX AND PREVENTING CMV INFECTION

(71) Applicant: CITY OF HOPE, Duarte, CA (US)

(72) Inventors: Don J. Diamond, Glendora, CA (US); Felix Wussow, Duarte, CA (US)

(73) Assignee: CITY OF HOPE, Duarte, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/919,110

(22) Filed: Mar. 12, 2018

(65) Prior Publication Data

US 2018/0303930 A1    Oct. 25, 2018

Related U.S. Application Data

(63) Continuation of application No. 14/606,973, filed on Jan. 27, 2015, now Pat. No. 9,931,395, which is a continuation of application No. PCT/US2013/032554, filed on Mar. 15, 2013.

(60) Provisional application No. 61/676,846, filed on Jul. 27, 2012.

(51) Int. Cl.
| | |
|---|---|
| *C12N 7/00* | (2006.01) |
| *A61K 39/00* | (2006.01) |
| *A61K 39/12* | (2006.01) |
| *A61K 39/245* | (2006.01) |
| *C07K 14/005* | (2006.01) |

(52) U.S. Cl.
CPC ............ *A61K 39/245* (2013.01); *A61K 39/12* (2013.01); *C07K 14/005* (2013.01); *C12N 7/00* (2013.01); *A61K 2039/5254* (2013.01); *A61K 2039/5256* (2013.01); *A61K 2039/70* (2013.01); *C12N 2710/16122* (2013.01); *C12N 2710/16134* (2013.01); *C12N 2710/24143* (2013.01); *C12N 2799/023* (2013.01); *C12N 2800/204* (2013.01)

(58) Field of Classification Search
CPC .. C07K 14/005; C07K 16/088; C07K 14/045; C07K 16/085; A61K 39/12; A61K 39/42; A61K 39/25; A61K 2039/525; A61K 2039/6075; A61K 35/76; A61K 35/763; C12N 2710/16134; C12N 7/00; C12N 2710/16122; C12N 2710/16151; C12N 2710/16111
See application file for complete search history.

(56) References Cited

U.S. PATENT DOCUMENTS

| | | | |
|---|---|---|---|
| 8,173,362 B2 | 5/2012 | Shenk et al. | |
| 8,580,276 B2 | 11/2013 | Diamond et al. | |
| 2003/0064077 A1 | 4/2003 | Paoletti et al. | |
| 2003/0166848 A1 | 9/2003 | Eaton et al. | |
| 2004/0110188 A1 | 6/2004 | Hahn | |
| 2004/0265325 A1 | 12/2004 | Diamond et al. | |
| 2006/0045873 A1 | 3/2006 | Taira et al. | |
| 2006/0229438 A1 | 10/2006 | Nagaraja et al. | |
| 2008/0187545 A1 | 8/2008 | Shenk et al. | |
| 2009/0081230 A1 | 11/2009 | Lanzavecchia et al. | |
| 2010/0143402 A1 | 6/2010 | Moss et al. | |
| 2010/0285059 A1 | 11/2010 | Shenk et al. | |
| 2010/0316667 A1 | 12/2010 | Diamond et al. | |
| 2010/0329980 A1 | 12/2010 | Kumar et al. | |
| 2011/0136896 A1 | 6/2011 | Fu et al. | |
| 2011/0209246 A1 | 8/2011 | Kovalic et al. | |
| 2012/0076801 A1 | 3/2012 | Lanzavecchia et al. | |
| 2013/0259876 A1 | 10/2013 | Murphy et al. | |
| 2014/0065181 A1 | 3/2014 | Diamond et al. | |
| 2014/0193428 A1 | 7/2014 | Lanzavecchia | |

FOREIGN PATENT DOCUMENTS

| | | |
|---|---|---|
| JP | 2011527899 A | 11/2011 |
| WO | 2006/056027 A1 | 6/2006 |
| WO | 2009/049138 A1 | 4/2009 |
| WO | 2012/034025 | 3/2012 |
| WO | 2014/005959 A1 | 1/2014 |
| WO | 2014/018117 A1 | 1/2014 |

OTHER PUBLICATIONS

Wang, Z., et al., "Pre-Clinical Development of a Subunit Vaccine Expressing an IE1-IE2 Fusion Protein of HCMV," Blood 110:165 (2007).
Abel et al., "Vaccine-induced control of viral shedding following rhesus cytomegalovirus challenge in rhesus macaques," J.Virol. (85):2878-2890 (2011).
Abel et al., "A heterologous DNA prime/protein boost immunization strategy for rhesus cytomegalovirus," Vaccine (26):6013-6025 (2008).

(Continued)

*Primary Examiner* — Rachel B Gill
(74) *Attorney, Agent, or Firm* — Perkins Coie LLP; Yang Tang

(57) ABSTRACT

In one embodiment, an expression system for expressing a UL128 complex is provided herein. The expression system may include a bacterial artificial chromosome (BAC) construct, wherein the BAC construct comprises a viral vector inserted with a set of DNA sequences that encode a UL128 complex. In another embodiment, a vaccine composition for preventing HCMV infection is provided. The vaccine composition may include a viral or bacterial vector capable of expressing a UL128 complex and a pharmaceutically acceptable carrier, adjuvant, additive or combination thereof or additional vector expressing a protein adjuvant. The viral vector may be an MVA and the UL128 complex includes five HCMV proteins or antigenic fragments thereof: UL128, UL130, UL131A, gL, and gH. In some embodiments, the viral vector is further inserted with one or more additional DNA sequences that encode one or more additional HCM-VHCMV proteins or antigenic fragments thereof such as pp65, gB or both, or such as gM/gN or gO.

20 Claims, 15 Drawing Sheets

Specification includes a Sequence Listing.

(56) References Cited

OTHER PUBLICATIONS

Acres, "Cancer immunotherapy: phase II clinical studies with TG4010 (MVA-MUC1-IL2)," J. Buon. 12 Suppl 1:S71-5 (2007).
Adler et al., "Recent advances in the prevention and treatment of congenital cytomegalovirus infections," Semin Perinatol. (31):10-18 (2007).
Adler et al., "Interrupting intrauterine transmission of cytomegalovirus." Rev Med Virol., (16):69-71 (2006).
Adler et al., "Role of human cytomegalovirus UL131A in cell type-specific virus entry and release," J.Gen.Virol. (87):2451-2460 (2006).
Adler et al., "Immunity induced by primary human cytomegalovirus infection protects against secondary infection among women of childbearing age." J.Infect.Dis., (171):26-32 (1995).
Adler et al., "Safety and immunogenicity of the Towne strain cytomegalovirus vaccine.", Pediatr.Infect.Dis.J. (17):200-206 (1998).
Andreoni, M., et al., "A rapid microneutralization assay for the measurement of neutralizing antibody reactive with human cytomegalovirus," J. Viral. Meth. 23:157-168 (1989).
Antoine et al., "The complete genomic sequence of the modified vaccinia Ankara strain: comparison with other orthopoxviruses," Virology 244:365-396 (1998).
Arvin et al., "Vaccine development to prevent cytomegalovirus disease: report from the National Vaccine Advisory Committee," Clin.Infect.Dis. (39):233-239 (2004).
Assaf et al., "Patterns of Acute Rhesus Cytomegalovirus (RhCMV) Infection Predict Long-Term RhCMV Infection," J.Virol. (86):6354-6357 (2012).
Avetisyan et al., "Evaluation of intervention strategy based on CMV-specific immune responses after allogeneic SCT," Bone Marrow Transplant 40:865-869 (2007).
Azuma et al., "2_-C-cyano-2_-deoxy-1-beta-Darabino-pentofuranosylcytosine: a novel anticancer nucleoside analog that causes both DNA strand breaks and G(2) arrest," Mol. Pharmacol.; 59(4):725-31 (2001).
Barouch et al., "Plasmid chemokines and colonystimulating factors enhance the immunogenicity of DNApriming-viral vector boosting human immunodeficiency virus type 1 vaccines," J. Virol. 77:8729-8735 (2003).
Barry et al., Primate Betaherpesviruses. 1051-1075 (2007).
Barry et al., Development of Breeding Populations of Rhesus Macaques That Are Specific Pathogen Free for Rhesus Cytomegalovirus, Comparative Medicine. (58):43-46 (2012).
Barry et al., Nonhuman primate models of intrauterine cytomegalovirus infection, Ilar.J. (47):49-64 (2006).
Berencsi et al., "A canarypox vector-expressing cytomegalovirus (cmv) phosphoprotein 65 induces long-lasting cytotoxic t cell responses in human cmv-seronegative subjects," J. Infect. Dis. 183:1171-1179 (2001).
Bernstein et al., Randomized, double-blind, Phase 1 trial of an alphavirus replicon vaccine for cytomegalovirus in CMV seronegative adult volunteers, Vaccine (28):484-493 (2009).
Bernstein, D. I., et al., "Safety and efficacy of a cytomegalovirus glycoprotein B (gB) vaccine in adolescent girls: A randomized clinical trial," Vaccine 34:313-319 (2016).
Blanchard et al., "Modified vaccinia virus Ankara undergoes limited replication in human cells and lacks several immunomodulatory proteins: implications for use as a human vaccine," J. Gen.Virol. 79(Pt 5):1159-1167 (1998).
Blut et al., Orthopox Viruses: Infections in Humans, Transfusion Med Hemother (37): 351-364 (2010).
Boeckh et al., "Immune monitoring with iTAg(TM) MHC tetramers for prediction of recurrent or persistent cytomegalovirus multicenter clinical trial," Biol. Blood Marrow Transplant. 12:79 (2006).
Boppana et al., "Antiviral antibody responses and intrauterine transmission after primary maternal cytomegalovirus infection.," J Infect Dis. (171):1115-1121 (1995).
Boppana et al., "Intrauterine transmission of cytomegalovirus to infants of women with preconceptional immunity," N. Engl. J. Med. (344):1366-1371. (2001).
Borst et al., Development of a cytomegalovirus vector for somatic gene therapy, Bone Marrow Transplant. 25 Suppl 2:S80-S82 (2000).
Britt et al., "Neutralizing antibodies detect a disulfide-linked glycoprotein complex within the envelope of human cytomegalovirus." Virology (135):369-378 (1984).
Britt et al., "Identification of a 65 000 dalton virion envelope protein of human cytomegalovirus," Virus Res 4:31-6 (1985).
Britt et al., "Structural and immunological characterization of the intracellular forms of an abundant 68,000 Mr human cytomegalovirus protein," J. Gen Virol; 68(Pt 7):1897-907) (1987).
Britt et al., "Induction of complement-dependent and -independent neutralizing antibodies by recombinant-derived human cytomegalovirus gp55-116 (gB) J. Virol." (62):3309-3318 (1988).
Britt et al., Cell surface expression of human cytomegalovirus (HCMV) gp55-116 (gB): use of HCMV-recombinant vaccinia virus-infected cells in analysis of the human neutralizing antibody response. J.Virol. 64:1079-1085 (1990).
Britt et al., Human cytomegalovirus virion proteins. Hum. Immunol. 65(5):395-402 (2004).
Britt et al., Manifestations of human cytomegalovirus infection: proposed mechanisms of acute and chronic disease. Curr Top Microbiol Immunol. (325):417-470 (2008).
Britt, W., "Controversies in the natural history of congenital human cytomegalovirus infection: the paradox of infection and disease in offspring of women with immunity prior to pregnancy," Med. Microbial. Immunol. 204:263-271 (2015).
Buscher, N., et al., "The proteome of human cytomegalovirus virions and dense bodies is conserved across different strains," Med. Microbial. Immunol. 204:285-293 (2015).
Butrapet et al, "Determining genetic stabilities of chimeric dengue vaccine candidates based on dengue 2 PDK-53 virus by sequencing and quantitative TaqMAMA," J Virol Methods; 131(1); 1-9 (2006).
Cannon, M. J., et al., "Washing our hands of the congenital cytomegalovirus disease epidemic," BMC Public Health 5:70 (2005).
Cannon, M. J., et al., "Awareness of and behaviors related to child-to-mother transmission of cytomegalovirus," Prev. Med. 54(5):351-357 (2012).
Carroll et al, "Highly attenuated modified vaccinia virus Ankara (MVA) as an effective recombinant vector: a murine tumor model," Vaccine 15:387-394 (1997).
Carroll et al, "Host range and cytopathogenicity of the highly attenuated MVA strain of vaccinia virus: propagation and generation of recombinant viruses in a nonhuman mammalian cell line," Virology 238:198-211 (1997).
Cha et al., Human cytomegalovirus clinical isolates carry at least 19 genes not found in laboratory strains. J Virol. (70):78-83 (1996).
Cha et al., Human cytomegalovirus clinical isolates carry at least 19 genes not found in laboratory strains. J Virol. (70):78-83 (1996).
Chakrabarti et al., "Compact, synthetic, vaccinia virus early/late promoter for protein expression," Biotechniques 23:1094-7 (1997).
Ciferri et al., "Antigenic Characterization of the HCMV gH/gL/gO and Pentamer Cell Entry Complexes Reveals Binding Sites for Potently Neutralizing Human Antibodies." PLoS Pathog. Oct. 20, 2015: 11(10): e1005230.
Ciferri, C., et al., "Structural and biochemical studies of HCMV gH/gL/gO and Pentamer reveal mutually exclusive cell entry complexes," PNAS 112(6):1767-1772 (2015).
Cobbold et al., "Adoptive transfer of cytomegalovirus-specific CTL to stem cell transplant patients after selection byHLA-peptide tetramers," J. Exp. Med. 202:379-386 (2005).
Cosma et al., "Therapeutic vaccination with MVA-HIV-1 Nef elicits Nef-specific T-helper cell responses in chronically HIV-1 infected individuals," Vaccine 22:21-9 (2003).
Cottingham et al., Rapid generation of markerless recombinant MVA vaccines by en passant recombineering of a self-excising bacterial artificial chromosome. J Virol Methods. (168):233-236 (2010).
Cottingham et al., Recombination-mediated genetic engineering of a bacterial artificial chromosome clone of modified vaccinia virus Ankara (MVA). PLoS.One. 3:e1638 (2008).

(56) References Cited

OTHER PUBLICATIONS

Cui et al., "Cytomegalovirus vaccines fail to induce epithelial entry neutralizing antibodies comparable to natural infection." Vaccine (26):5760-5766 (2008).
Cui, X., et al., "Antibody inhibition of human cytomegalovirus spread in epithelial cell cultures," J. Viral. Methods 192:44-50 (2013).
Cwynarski et al., "Direct visualization of cytomegalovirusspecific T-cell reconstitution after allogeneic stem cell transplantation," Blood 97:1232-1240 (2001).
Daftarian et al., "Novel conjugates of epitope fusion peptides with CpG-ODN display enhanced immunogenicity and HIV recognition," Vaccine 23:3453-3468 (2005).
Dasari, V.,et al., "Recent advances in designing an effective vaccine to prevent cytomegalovirus-associated clinical diseases," Expert Rev. Vaccines 12(6):661-676 (2013).
Davison AJ,. RecName: Full=Uncharacterized w protein UL 128. UniProtKB/Swiss-Prot: P16837.2. Updated Nov. 3, 2009.
Dawson et al., "Data for biochemical research," Oxford University Press; p. 260-1 (1986).
De Haan et al., "Coronaviruses as vectors: stability of foreign gene expression," J Virol 79:12742-51 (2005).
Dewaal et al., "Vaccination of infant macaques with a recombinant MVA expressing the RSV F and G genes does not predispose for immunopathology," Vaccine 22:923-926 (2004).
Diamond et al., "Development of a candidate HLA A*0201 restricted peptide-based vaccine against human cytomegalovirus infection," Blood 90:1751-67 (1997).
Domi et al., Cloning the vaccinia virus genome as a bacterial artificial chromosome in *Escherichia coli* and recovery of infectious virus in mammalian cells. Proc.Natl.Acad.Sci.U.S.A (99):12415-12420 (2002).
Domi et al., Engineering of a vaccinia virus bacterial artificial chromosome in *Escherichia coli* by bacteriophage λ-based recombination. Nat. Methods 2(2):95-97 (2005).
Drexler et al., "Modified vaccinia virus Ankara as antigen delivery system: how can we best use its potential?" Curr Opin Biotechnol 15:506-12 (2004).
Dunn et al., Functional profiling of a human cytomegalovirus genome. Proc Natl Acad Sci U S A. (100):14223-14228 (2003).
Earl et al., Generation of recombinant vaccinia viruses. Curr.Protoc. Mol.Biol. Chapter 16:Unit16 (2001).
Earl et al., Recombinant modified vaccinia virus Ankara provides durable protection against disease caused by an immunodeficiency virus as well as long-term immunity to an orthopoxvirus in a non-human primate. Virology. (366):84-97 (2007).
Earl et al., "Design and evaluation of multi-gene, multi-clade HIV-1MVAvaccines." Vaccine; 27(42):5885-95 (2009).
Einsele et al., "Infusion of cytomegalovirus (CMV)-specific T cells for the treatment of CMVinfection not responding to antiviral chemotherapy," Blood 99:3916-3922 (2002).
Endresz et al., Optimization of DNA immunization against human cytomegalovirus. Vaccine (19):3972-3980 (2001).
Erfle et al., "Vaccines based on Nef and on Nef/DeltaV2," Env. Microbes Infect; 7(14):1400-4 (2005).
Espenschied et al., "CTLA-4 blockage enhances the therapeutic effect of an attenuated poxvirus vaccine targeting p53 in an established murine tumor model," J Immunol 170:3401-7 (2003).
European Patent Office, Communication pursuant to Article 94(3) EPO dated Jul. 17, 2017 for European Application No. 13822266.6.
Even-Desrumeaux, K., et al., "Affinity determination of biotinylated antibodies by flow cytometry," Methods Mal. Biol. 907:443-449 (2012).
Fayzulin et al., "Evaluation of replicative capacity and genetic stability of West Nile virus replicons using highly efficient packaging cell lines," Virology; 351(1)196-209 (2006).
Fields, C., et al., "Creation of recombinant antigen-binding molecules derived from hybridomas secreting specific antibodies," Nat. Protoc. 8(6):1125-1148 (2013).

Firat et al., "Comparative analysis of the CD8(+) T cell repertoires of H-2 class I wild-type/HLA-A2.1 and H-2 class I knockout/HLA-A2.1 transgenic mice," Int. Immunol. 14:925-934 (2002).
Fisher, S., et al., "Human cytomegalovirus infection of placental cytotrophoblasts in vitro and in utero: Implications for transmission and pathogenesis," J. Viral. 7 4(15):6808-6820 (2000).
Fouts et al., "Antibodies against the gH/gL/UL128/UL130/UL131 complex comprise the majority of the anti-CMV neutralizing antibody response in CMV-HIG." J.Virol. (86):7444-7447 (2012).
Fouts, A E., "Pentameric complex of viral glycoprotein H is the primary target for potent neutralization by a human cytomegalovirus vaccine," J. Viral. 86(13):7 444-7 447 (2012).
Frank, H. G., et al., "Cell culture models of human trophoblast— Primary culture of trophoblast—A workshop report," Placenta 21 (Suppl. A):S120-S122 (2000).
Freed, D. C., et al., "Pentameric complex of viral glycoprotein H is the primary target for potent neutralization by a human cytomegalovirus vaccine," PNAS 110: E4997-E5005 (2013).
Gallez-Hawkins et al., "Ctyomegalovirusimmune reconstitution occurs in recipients of allogeneic hematopoietic celltransplants irrespective of detectable cytomegalovirus infection," Biol. Blood MarrowTransplant. 11:890-902 (2005).
Genini et al., Serum antibody response to the gH/gL/pUL128-131 five-protein complex of human cytomegalovirus (HCMV) in primary and reactivated HCMV infections. J.Clin.Virol. (52):113-118 (2011).
Gerna et al., "Human cytomegalovirus serum neutralizing antibodies block virus infection of endothelial/epithelial cells, but not fibroblasts, early during primary infection." J.Gen.Virol. (89):853-865 (2008).
Ghanekar et al., "Gamma interferon expression in CD8(+) T cells is a marker for circulating cytotoxic T lymphocytes that recognize an HLA A2-restricted epitope of human cytomegalovirus phosphoprotein pp65," Clin. Diagn. Lab. Immunol. 8:628-631 (2001).
Gherardi et al., "Recombinant poxviruses as mucosal vaccine vectors," J Gen Virol 86:2925-36 (2005).
Gilbert et al., "Cytomegalovirus selectively blocks antigen processing and presentation of its immediate-early gene product," Nature 383:720-722 (1996).
Gilbert et al., "Selective interference with class I major histocompatibility complex presentation of the major immediate-early protein infection with human cytomegalovirus," J. Virol. 67:3461-3469 (1993).
Gilbert et al., "Synergistic DNA-MVA prime-boost vaccination regimes for malaria and tuberculosis," Vaccine 24:4554-61 (2006).
Gomez et al., "Head-to-head comparison on the immunogenicity of two HIV/AIDS vaccine candidates based on the attenuated poxvirus strains MVA and NYVAC co-expressing in a single locus the HIV-1BX08 gp120 and HIV-1(IIIb) Gag-Pol-Nef proteins of clade B," Vaccine 25:2863-2885 (2007).
Gonczol et al., Isolated gA/gB glycoprotein complex of human cytomegalovirus envelope induces humoral and cellular immune-responses in human volunteers. Vaccine. (8):130-136 (1990).
Gonczol et al., Development of a cytomegalovirus vaccine: lessons from recent clinical trials. Expert Opin Biol Ther. (1):401-412 (2001).
Goonetilleke et al., "Induction of multifunctional human immunodeficiency virus type 1 (HIV-1)-specific T cells capable of proliferation in healthy subjects by using a prime-boost regimen of DNA and modified vaccinia virus Ankara-vectored vaccines expressing HIV-1 gag coupled to CD8+ T-cell epitopes," J. Virol. 80:4717-4728 (2006).
Gratama et al., "Tetramer-based quantification of cytomegalovirus (CMV)-specific CD8+ T lymphocytes in T-cell-depleted stem cell grafts and after transplantation may identify patients at risk for progressive CMV infection," Blood 98:1358-1364 (2001).
Grazia et al., in vitro selection of human cytomegalovirus variants unable to transfer virus and virus products from infected cells to polymorphonuclear leukocytes and to grow in endothelial cells. J Gen Virol. (82):1429-1438 (2001).
Greenspan N.S. et al., "Defining Epitopes: It's not as easy as it seems." Nat Biotechnol. Oct. 17, 1999 (10): 936-7.

(56) References Cited

OTHER PUBLICATIONS

Griffiths et al., "Cytomegalovirus glycoprotein-B vaccine with MF59 adjuvant in transplant recipients: a phase 2 randomised placebo-controlled trial." Lancet (377):1256-1263 (2011).
Griffiths, P., et al., "Desirability and feasibility of a vaccine against cytomegalovirus," Vaccine 31 (Suppl 2): B 197-8203 (2013).
Gyulai et al., "Cytotoxic T lymphocyte (CTL) responses to human cytomegalovirus pp65, IE1-Exon4, gB, pp150, and pp28 in healthy individuals: reevaluation of prevalence of IE1-Specific CTLs," J. Infect. Dis. 181:1537-1514 (2000).
Hahn et al., "Human cytomegalovirus UL131-128 genes are indispensable for virus growth in endothelial cells and virus transfer to leukocytes." J.Virol. (78):10023-10033 (2004).
Hanke et al., "Biodistribution and persistence of an MVAvectored candidate HIV vaccine in SIV-infected rhesus macaques and SCID mice." Vaccine. (23):1507-1514 (2005).
Hansen et al., "Evasion of CD8+ T cells is critical for superinfection by cytomegalovirus." Science. (328):102-106 (2010).
Hansen et al., "Complete sequence and genomic analysis of rhesus cytomegalovirus." J.Virol. (77):6620-6636 (2003).
Harrer, E., et al., "Therapeutic vaccination of H IV-1-infected patients on HAART with a recombinant HIV-1 net-expressing MVA: safety, immunogenicity and influence on viral load during treatment interruption," Antiviral Therapy 10:285-300 (2005).
Heineman et al., "A phase 1 study of 4 live, recombinant human cytomegalovirus Towne/Toledo chimeric vaccines." J Infect Dis. (193):1350-1360 (2006).
Huff et al., Differential detection of B virus and rhesus cytomegalovirus in rhesus macaques. J.Gen.Virol. (84):83-92 (2003).
Isaacson et al., Human cytomegalovirus glycoprotein B is required for virus entry and cell-to-cell spread but not for virion attachment, assembly, or egress. J.Virol. (83):3891-3903 (2009).
Jacob, C. L., et al., "Neutralizing antibodies are unable to inhibit direct viral cell-to-cell spread of human cytomegalovirus," Viral. 444: 140-147 (2013).
Jarvis et al., Molecular basis of persistence and latency. Human Herpesviruses: Biology, Therapy, and Immunoprophylaxis. Cambridge University Press; (2007).
Johnson et al., "O-linked oligosaccharides are acquired by herpes simplex virus glycoproteins in the Golgi apparatus." Cell (32):987-997 (1983).
Johnson, E. L., et al., "Placental Hofbauer cells limit HIV-1 replication and potentially offset mother to child transmission (MTCT) by induction of immunoregulatory cytokines," Retrovirol. 9: 101 (2012).
Johnson, E. L., et al., "Placental Hofbauer cells assemble and sequester HIV-1 in tetraspanin-positive compartments that are accessible to broadly neutralizing antibodies," J. Int. AIDS Soc. 18: 19385 (2015).
Johnson et al., "Domain mapping of the human cytomegalovirus IE1-72 and cellular p107 protein-protein interaction and the possible functional consequences," J. Gen. Virol. 80(5):1293-1303 (1999).
Kabanova, A., et al., "Antibody-driven design of a human cytomegalovirus gHglpUL 128L subunit vaccine that selectively elicits potent neutralizing antibodies," PNAS 111 (50): 17965-17970 (2014).
Kauvar, L. M., et al., "A high-affinity native human antibody neutralizes human cytomegalovirus infection of diverse cell types," Antimicrob. Agents Chem other. 59: 1558-1568 (2015).
Kenneson, A., et al., "Review and meta-analysis of the epidemiology of congenital cytomegalovirus (CMV) infection," Rev. Med. Viral. 17:253-276 (2007).
Kern et al., "Target structures of the CD8(+)-T-cell response to human cytomegalovirus: the 72 kilodalton major immediate-early protein revisited," J. Virol. 73:8179-8184 (1999).
Khan et al., "Comparative analysis of CD8+ T cell responses against human cytomegalovirus proteins pp65 and immediate early 1 shows similarities in precursor frequency, oligoclonality, and phenotype," J Infect Dis 185:1025-34 (2002).

Khan et al., "Identification of cytomegalovirus-specific cytotoxic T lymphocytes in vitro is greatly enhanced by the use of recombinant virus lacking the US2 to US11 region or modified vaccinia virus Ankara expressing individual viral genes," J. Virol. 79:2869-2879 (2005).
Khan et al., "T cell recognition patterns of immunodominant cytomegalovirus antigens in primary and persistent infection," J. Immunol. 178:4455-4465 (2007).
Khanna et al., "Human cytomegalovirus vaccine: time to look for alternative options," Trends Mol. Med. 12:26-33 (2006).
Kharfan-Dabaja et al., "A novel therapeutic cytomegalovirus DNA vaccine in allogeneic haemopoietic stem-cell transplantation: a randomised, double-blind, placebo-controlled, phase 2 trial." Lancet Infect. Dis. (12):290-299 (2012).
Kidokoro et al., "Genetically stable and fully effective smallpox vaccine strain constructed from highly attenuated vaccinia LC16m8," Proc Natl Acad Sci USA; 102(11):4152-7 (2005).
Kinzler et al., Characterization of human cytomegalovirus glycoproteininduced cell-cell fusion. J Virol. (79):7827-7837 (2005).
Krause, P. R., et al., "Priorities for CMV vaccine development," Vaccine 32( 1):4-10 (2013).
Kringelum, J. V., et al., "Structural analysis of B-cell epitopes in antibody:protein complexes," Mal. Immunol. 53:24-34 (2013).
Krishnan et al., "A novel approach to evaluate the immunogenicity of viral antigens of clinical importance in HLA transgenic murine models," Immunol Lett; 120(1-2):108-16 (2008).
La Rosa et al., "Enhanced immune activity of cytotoxic T-lymphocyte epitope analogs derived from positional scanning synthetic combinatorial libraries," Blood 97:1776-86 (2001).
La Rosa et al., "In vitro expansion of polyclonal T-cell subsets for adoptive immunotherapy by recombinant modified vaccinia Ankara," Exp Hematol 34:497-507 (2006).
La Rosa et al., "Longitudinal assessment of cytomegalovirus (CMV)-specific immune responses in liver transplant recipients at high risk for late CMV disease," J. Infect. Dis. 195:633-644 (2007).
La Rosa et al., "Preclinical development of an adjuvant-free peptide vaccine with activity against CMV pp65 in HLA transgenic mice," Blood; 100(10):3681-9 (2002).
La Rosa, C., et al., "The immune response to human CMV," Future Viral. 7(3):279-293 (2012).
La Torre et al., Placental enlargement in women with primary maternal cytomegalovirus infection is associated with fetal and neonatal disease. Clin Infect Dis. (43):994-1000 (2006).
Lacey et al., "Functional comparison of T cells recognizing cytomegalovirus pp65 and intermediate-early antigen polypeptides in hematopoietic stem-cell transplant and solid organ transplant recipients," J. Infect. Dis. 194:1410-1421 (2006).
Lai et al., "A rapid method for screening vaccinia virus recombinants," Biotechniques 10:564-5 (1991).
Lazzarotto, T., et al., "Diagnosis and prognosis of congenital CMV infection: A case report and review of the literature," Scand. J. Clin. Lab. Invest. 74(Suppl. 244):34-40 (2014).
Lemonnier, "The utility of H-2 class I knockout mice," Virus Res. 82:87-90 (2002).
Li, G., et al., "A viral regulator of glycoprotein complexes contributes to human cytomegalovirus cell tropism," PNAS 112(14):4471-4476 (2015).
Li, Z.,et al., "The generation of antibody diversity through somatic hypermutation and class switch recombination," Genes Devel. 18: 1-11 (2004).
Li, Z., et al., "The generation of antibody diversity through somatic hypermutation and class switch recombination," Genes Dev. 18: 1-11 (2004).
Lilja et al., Efficient replication of rhesus cytomegalovirus variants in multiple rhesus and human cell types. Proc.Natl.Acad.Sci.U.S.A (105):19950-19955 (2008).
Lilleri et al., Development of Human Cytomegalovirus-Specific T Cell Immunity during Primary Infection of Pregnant Women and Its Correlation with Virus Transmission to the Fetus. J Infect Dis. (195):1062-1070 (2007).
Limaye et al., "Impact of cytomegalovirus in organ transplant recipients in the era of antiviral prophylaxis," Transplantation 81(12):1645-1652 (2006).

(56) References Cited

OTHER PUBLICATIONS

Liu et al., "The N-terminal 513 amino acids of the envelope glycoprotein gB of human cytomegalovirus stimulates both B- and T-cell immune responses in humans." J Virol. (65):1644-1648 (1991).

Ljungman et al., "Risk factors for development of cytomegalovirus disease after allogeneic stem cell transplantation," Haematolgica 91:78-83 (2006).

Longmate et al., "Population coverage by HLA class-I restricted cytotoxic T-lymphocyte epitopes," Immunogenetics 52:165-173 (2001).

Lubaki et al., "A novel method for detection and ex vivo expansion of HIV type 1-specific cytolytic T lymphocytes. AIDS Res Hum Retroviruses." (10):1427-1431 (1994).

Ludwig, A., et al., "Epidemiological impact and disease burden of congenital cytomegalovirus infection in Europe," Eurosurveillance 14(9): 1-7 (2009).

Macagno et al., Isolation of human monoclonal antibodies that potently neutralize human cytomegalovirus infection by targeting different epitopes on the gH/gL/UL128-131A complex. J.Virol. (84):1005-1013 (2010).

Macagno, A., et al., "Isolation of human monoclonal antibodies that potently neutralize human cytomegalovirus infection by targeting different epitopes on the gH/gL/UL 128-131A complex," J. Viral. 84(2):1005-1013 (2010).

Maecker et al., "Impact of cryopreservation on tetramer, cytokine flow cytometry, and ELISPOT," BMC Immunol. 6:17 (2005).

Maidji et al., "Maternal antibodies enhance or prevent cytomegalovirus infection in the placenta by neonatal Fc receptormediated transcytosis." Am J Pathol. (168):1210-1226 (2006).

Maidji et al., "Transmission of human cytomegalovirus from infected uterine microvascular endothelial cells to differentiating/invasive placental cytotrophoblasts." Virology. (304):53-69 (2002).

Maldonado-Estrada, J., et al., "Evaluation of cytokeratin 7 as an accurate intracellular marker with which to assess the purity of human placental villous trophoblast cells by flow cytometry," J. Immunol. Meth. 286:21-34 (2004).

Manicklal, S., et al., "The "silent" global burden of congenital cytomegalovirus," Clin. Microbial. Rev. 26(1):86-102 (2013).

Manley et al., "Immune evasion proteins of human cytomegalovirus do not prevent a diverse CD8+ cytotoxic T-cell response in natural infection," Blood 104:1075-1082 (2004).

Mansat et al., Cytomegalovirus detection in cryopreserved semen samples collected for therapeutic donor insemination. Hum Reprod. (12):1663-1666 (1997).

Manuel et al., Intergenic region 3 of modified vaccinia ankara is a functional site for insert gene expression and allows for potent antigen-specific immune responses. Virology. (403):155-162 (2010).

Manoussaka, M. S., et al., "Flow cytometric characterisation of cells of differing densities isolated from human term placentae and enrichment of villous trophoblast cells," Placenta 26:308-318 (2005).

Marshall et al., Ontogeny of glycoprotein gB-specific antibody and neutralizing activity during natural cytomegalovirus infection. J.Med. Virol. (43):77-83 (1994).

Mateu MG et al., "Non-additive effects of multiple amino aicd substitutions on antigen-antibody recognition." Eur J Immunol. Jun. 22, 1992 (6): 1385-9.

Mayr et al., "Attenuation of virulent fowl pox virus in tissue culture and characteristics of the attenuated virus." Zentralbl. Veterinarmed.B (13):1-13 (1966).

Mayr et al., "Vaccination against pox diseases under immunosuppressive conditions." Dev. Biol. Stand, 41:225-34, 225-234 (1978).

McDonagh, S., et al., "Patterns of human cytomegalovirus infection in term placentas: A preliminary analysis," J. Clin. Viral. 35:210-215 (2006).

Meyer et al., "Mapping of deletions in the genome of the highly attenuated vaccinia virusMVA and their influence on virulence," J.Gen.Virol. 72(5):1031-1038 (1991).

Mohr et al., Engineering of cytomegalovirus genomes for recombinant live herpesvirus vaccines. Int. J. Med. Microbiol. 298(1-2):115-125 (2008).

Moorthy et al., "Safety and immunogenicity of DNA/modified vaccinia virus Ankara malaria vaccination in African adults," J. Infect. Dis. 188:1239-1244 (2003).

Morello et al., "Suppression of murine cytomegalovirus (MCMV) replication with a DNA vaccine encoding MCMV M84 (a homolog of human cytomegalovirus pp65)," J. Virol. 74:3696-3708 (2000).

Moss, "Genetically engineered poxviruses for recombinant gene expression, vaccination, and safety," Proc Natl Acad Sci USA; 93(21):11341-8 (1996).

Moss et al., "Host range restricted, non-replicating vaccinia virus vectors as vaccine candidates," Adv Exp Med Biol 397:7-13 (1996).

Murphy et al., Coding potential of laboratory and clinical strains of human cytomegalovirus. Proc.Natl.Acad.Sci.U.S.A (100):14976-14981 (2003).

Navarro et al., Glycoprotein B of human cytomegalovirus promotes virion penetration into cells, transmission of infection from cell to cell, and fusion of infected cells. Virology. (197):143-158 (1993).

Nigro et al., Regression of fetal cerebral abnormalities by primary cytomegalovirus infection following hyperimmunoglobulin therapy. Prenat Diagn. (28):512-517 (2008).

Nigro et al., Passive immunization during pregnancy for congenital cytomegalovirus infection. N.Engl.J.Med. (353):1350-1362 (2005).

Non-Final Office Action dated Jul. 9, 2018 in U.S. Appl. No. 15/917,502 for Diamond, Don J., filed Mar. 9, 2018.

Ornoy, A, et al., "Fetal effects of primary and secondary cytomegalovirus infection in pregnancy," Reprod. Toxicol. 21 :399-409 (2006).

Oxford et al., Open reading frames carried on UL/b' are implicated in shedding and horizontal transmission of rhesus cytomegalovirus in rhesus monkeys. J.Virol. (85):5105-5114 (2011).

Oxford et al., Protein coding content of the UL)b' region of wild-type rhesus cytomegalovirus. Virology (373):181-188 (2008).

Pascolo et al., "HLAA2.1-restricted education and cytolytic activity of CD8(+) T lymphocytes from beta2 microglobulin (beta2m) HLA-A2.1 monochain transgenic H-2Db beta2m double knockout mice," J. Exp. Med. 185:2043-2051 (1997).

Pass et al., "A subunit cytomegalovirus vaccine based on recombinant envelope glycoprotein B and a new adjuvant." J.Infect.Dis. (180):970-975 (1999).

Pass et al., "Congenital cytomegalovirus infection following first trimester maternal infection: symptoms at birth and outcome," J. Clin.Virol. 35:216-220 (2006).

Pass, R. F., "Development and evidence for efficacy of CMV glycoprotein B vaccine with MF59 adjuvant," J. Clin. Viral. 46(Suppl 4):S73-S76 (2009).

Pass et al., "Vaccine prevention of maternal cytomegalovirus infection." N.Engl.J.Med. (360):1191-1199 (2009).

Pass, R. F., et al., "Mother-to-child transmission of cytomegalovirus and prevention of congenital infection," J. Ped. Infect. Dis. Soc. 3(Suppl 1 ):S2-S6 (2014).

Patrone et al., Human cytomegalovirus UL130 protein promotes endothelial cell infection through a producer cell modification of the virion. J Virol. (79):8361-8373 (2005).

Pereira, L., et al., "Insights into viral transmission at the uterineplacental interface," Trends in Microbial. 13(4):164-174 (2005).

Pereira, L., et al., "Cytomegalovirus infection in the human placenta: Maternal immunity and developmentally regulated receptors on trophoblasts converge," Curr. Topics in Microbial. Immunol. 325:383-395 (2008).

Pereira, L., et al., "Intrauterine growth restriction caused by underlying congenital cytomegalovirus infection," J. Infect. Dis. 209: 1573-1584 (2014).

Peters, "Integrating epitope data into the emerging web of biomedical knowledge resources," Nat. Rev. Immunol. 7:485-490 (2007).

Peters et al., "Studies of a prophylactic HIV-1 vaccine candidate based on modified vaccinia virus Ankara (MVA) with and without DNA priming: effects of dosage and route on safety and immunogenicity," Vaccine 25:2120-7 (2007).

Plachter et al., "Analysis of proteins encoded by IE regions 1 and 2 of human cytomegalovirus using monoclonal antibodies generated against recombinant antigens," Virology 193:642-52 (1993).

Platcher et al., Cell types involved in replication and distribution of human cytomegalovirus. Adv Virus Res. (46):195-261 (1996).

(56) References Cited

OTHER PUBLICATIONS

Plotkin et al., Candidate cytomegalovirus strain for human vaccination. Infect Immun. (12):521-527 (1975).
Plotkin et al., Effect of Towne live virus vaccine on cytomegalovirus disease after renal transplant. Ann Intern Med. (114):525-531 (1991).
Plotkin et al., Protective effects of Towne cytomegalovirus vaccine against low-passage cytomegalovirus administered as a challenge. J Infect Dis. (159):860-865 (1989).
Potgens, A J. G., et al., "Characterization of trophoblast cell isolations by a modified flow cytometry assay," Placenta 22:251-255 (2001).
Ramirez et al., "Biology of attenuated modified vaccinia virus Ankara recombinant vector in mice: Virus fate and activation of B- and T-cell immune responses in comparison with the Western Reserve strain and advantages as a vaccine," J Virol 74:923-33 (2000).
Rasmussen et al., Antibody response to human cytomegalovirus glycoproteins gB and gH after natural infection in humans. J.Infect. Dis. (164):835-842 (1991).
Rauwel, B., et al., "Activation of peroxisome proliferator-activated receptor gamma by human cytomegalovirus for de nova replication impairs migration and invasiveness of cytotrophoblasts from early placentas," J. Viral. 84(6):2946-2954 (2010).
Reap et al., "Cellular and humoral immune responses to alphavirus replicon vaccines expressing cytomegalovirus pp65, 1E1, and gB proteins," Clinical Vaccine Immunology 14(6):748-755 (2007).
Reddehase et al., "CD8-positive T lymphoctyes specific for murine cytomegalovirus immediate-early antigens mediate protective immunity," J. Virol. 61:3102-3108 (1987).
Revello et al., "Human cytomegalovirus tropism for endothelial/epithelial cells: scientific background and clinical implications." Rev.Med.Virol. (20):136-155 (2010).
Rivailler et al., Genomic sequence of rhesus cytomegalovirus 180.92: insights into the coding potential of rhesus cytomegalovirus. J.Virol. (80):4179-4182 (2006).
Rochlitz et al., "Phase I immunotherapy with a modified vaccinia virus (MVA) expressing human MUC1 as antigen-specific immunotherapy in patients with MUC1-positive advanced cancer," J Gene Med 5:690-9 (2003).
Rohrlich et al., "HLA-B☐0702 transgenic, H-2KbDb double-knockout mice: phenotypical and functional characterization in response to influenza virus," Int. Immunol. 15:765-772 (2003).
Ryckman et al., Human cytomegalovirus entry into epithelial and endothelial cells depends on genes UL128 to UL150 and occurs by endocytosis and low-pH fusion. J Virol. (80):710-722 (2006).
Ryckman et al., Characterization of the human cytomegalovirus gH/gL/UL128-131 complex that mediates entry into epithelial and endothelial cells. J.Virol. (82):60-70 (2008).
Ryckman et al., HCMV gH/gL/UL128-131interferes with virus entry into epithelial cells: evidence for cell type-specific receptors. Proc.Natl.Acad.Sci.U.S.A (105):14118-14123 (2008).
Ryckman et al., Human cytomegalovirus TR strain glycoprotein O acts as a chaperone promoting gH/gL incorporation into virions but is not present in virions. J.Virol. (84):2597-2609 (2010).
Saccoccio et al., "Peptides from cytomegalovirus UL130 and UL131 proteins induce high titer antibodies that block viral entry into mucosal epithelial cells." Vaccine. (29):2705-2711 (2011).
Sandstrom et al., "Broad immunogenicity of a multigene. Multiclade HIV-1 DNA vaccine boosted with heterologous HIV-1 recombinant modified vaccinia virus Ankara," J Infect Dis; 198(10):1482-90 (2008).
Schleiss et al., Role of breast milk in acquisition of cytomegalovirus infection: recent advances. Curr Opin Pediatr. (18):48-52 (2006).
Schleiss et al., Nonprimate models of congenital cytomegalovirus (CMV) infection: gaining insight into pathogenesis and prevention of disease in newborns. ILAR.J. (47):65-72 (2006).

Schleiss et al., "Preconceptual administration of an alphavirus replicon UL83 (pp65 homolog) vaccine induces humoral and cellular immunity and improves pregnancy outcome in the guinea pig model of congenital cytomegalovirus infection," J. Infect. Dis. 195:789-798 (2007).
Schleiss et al., Analysis of the nucleotide sequence of the guinea pig cytomegalovirus (GPCMV) genome. Virol.J. (5):139 (2008).
Schleiss et al., Cytomegalovirus vaccines and methods of production (WO20009049138): the emerging recognition of the importance of virus neutralization at the epithelial/endothelial interface. Expert.Opin.Ther.Pat (20):597-602 (2010).
Schmelz et al., "Assembly of vaccinia virus: the second wrapping cisterna is derived from the trans Golgi network," J Virol 1994; 68(1):130-47 (1994).
Scrivano, L., et al., "HCMV spread and cell tropism are determined by distinct virus populations," PLoS Pathog. 7(1):e1001256 (2011).
Sequar et al., Experimental coinfection of rhesus macaques with rhesus cytomegalovirus and simian immunodeficiency virus: pathogenesis. J.Virol. (76):7661-7671 (2002).
Shimamura et al., Human cytomegalovirus infection elicits a glycoprotein M (gM)/gN-specific virus-neutralizing antibody response. J.Virol. (80):4591-4600 (2006).
Sinclair et al., "CMV antigen-specific CD4+ and CD8+ T Cell IFNgamma expression and proliferation responses in healthy CMV-seropositive individuals," Viral Immunol. 17:445-454 (2004).
Sinclair et al., "Protective immunity to cytomegalovirus (CMV) retinitis in AIDS is associated with CMV-specific T cells that express interferon-gamma and interleukin-2 and have a CD8+ cell early maturational phenotype," J. Infect. Dis. 194:1537-1546 (2006).
Singh, H., et al., "Improved method for linear B-cell epitope prediction using antigen's primary sequence," PLoS One 8(5):e62216 (2013).
Sinzger et al., "Cytomegalovirus cell tropism." Curr.Top.Microbiol. Immunol. (325):63-83 (2008).
Sinzger, C., et al., "Cloning and sequencing of a highly productive, endotheliotropic virus strain derived from human cytomegalovirus TB40/E," J. Gen. Viral. 89:359-368 (2008).
Song et al., "An MVA vaccine overcomes tolerance to human p53 in mice and humans," Canc. Immunol. Immunother. 56(8):1193-205 (2007).
Stagno et al., Cervical cytomegalovirus excretion in pregnant and nonpregnant women: suppression in early gestation. J Infect Dis. (131):522-527 (1975).
Stickl et al., "MVA vaccination against smallpox: clinical tests with an attenuated live vaccinia virus strain (MVA) (author's translation)," Dtsch. Med. Wochenschr 99:2386-2392 (1974).
Stittelaar et al., "Protective immunity in macaques vaccinated with a modified vaccinia virus Ankara-based measles virus vaccine in the presence of passively acquired antibodies." J Virol; 74(9):4236-43 (2000).
Stittelaar et al., "Safety of modified vaccinia virus Ankara (MVA) in immune-suppressed macaques," Vaccine 19:3700-9 (2001).
Stratton et al., "Vaccines for the 21st Century: A tool for decision making." Bethesda: National Academy Press. (2001).
Sung et al., Update of the current status of cytomegalovirus vaccines. Expert Rev Vaccines. (11):1303-1314 (2010).
Sutter, "Vaccinia vectors as candidate vaccines: the development of modified vaccinia virus Ankara for antigen delivery," Curr Drug Targets Infect Disord.; 3(3):263-71 (2003).
Sylwester et al., "Broadly targeted human cytomegalovirus-specific CD4+ and CD8+ T cells dominate the memorycompartments of exposed subjects," J. Exp. Med. 202:673-685 (2005).
Tabata, T., et al., "Cytotrophoblasts infected with a pathogenic human cytomegalovirus strain dysregulate celleMatrix and cell-cell adhesion molecules: A quantitative analysis," Placenta 28:527-537 (2007).
Tang, Z., et al., "Isolation of Hofbauer cells from human term placentas with high yield and purity," Am. J. Reprod. Immunol. 66(4):336-348 (2011).
Timm et al., Genetic stability of recombinant MVA-BN. Vaccine. (24):4618-4621 (2006).

(56) References Cited

OTHER PUBLICATIONS

Tischer et al., Two-step red-mediated recombination for versatile high-efficiency markerless DNA manipulation in *Escherichia coli*. Biotechniques (40):191-197 (2006).
Tischer et al., "En passant mutagenesis: a two step markerless red recombination system," Methods Mol.Biol. (634):421-430 (2010).
Tobery et al., "Targeting of HIV-1 antigens for rapid intracellular degradation enhances cytotoxic T lymphocyte (CTL) recognition and the induction of de novo CTL responses in vivo after immunization," J Exp Med; 185(5):909-20 (1997).
Trincado, D. E., et al., "Highly sensitive detection and localization of maternally acquired human cytomegalovirus in placental tissue by in situ polymerase chain reaction," J. Infect. Dis. 192:650-657 (2005).
Uhde-Holzem et al., "Genetic stability of recombinant potato virus×virus vectors presenting foreign epitopes," Arch Virol; 152(4):805-11 (2007).
United States Patent and Trademark Office, International Search Report and Written Opinion dated Mar. 7, 2017 for PCT/US16/51167.
Urban et al., "Glycoprotein H of human cytomegalovirus is a major antigen for the neutralizing humoral immune response," J.Gen. Virol. 77 ( Pt 7):1537-1547 (1996).
Urban, M., et al., "The dominant linear neutralizing antibody-binding site of glycoprotein gp86 of human cytomegalovirus is strain specific," J. Viral. 66(3):1303-1311 (1992).
Van Regenmortel, M. H. V., "Immunoinformatics may lead to a reappraisal of the nature of B cell epitopes and of the feasibility of synthetic peptide vaccines," J. Mal. Recog. 19:183-187 (2006).
Van Kooten et al., "CD40-CD40 ligand," J.Leukoc.Biol. (67):2-17 (2000).
Vanarsdall et al., "Human cytomegalovirus entry into cells," Curr. Opin.Virol. (2):37-42 (2012).
Vanarsdall, A L., et al., "Human cytomegalovirus glycoprotein gO complexes with gH/gL, promoting interference with viral entry into human fibroblasts but not entry into epithelial cells," J. Viral. 85(22): 11638-11645 (2011 ).
Vanarsdall et al., "Human cytomegalovirus glycoproteins gB and gH/gL mediate epithelial cell-cell fusion when expressed either in cis or in trans," J.Virol. (82):11837-11850 (2008).
Verheust et al., "Biosafety aspects of modified vaccinia virus Ankara (MVA)-based vectors used for gene therapy or vaccination," Vaccine 30(16):2623-2632 (2012).
Walter et al., "Reconstitution of cellular immunity against cytomegalovirus in recipients of allogeneic bone marrow by transfer of T-cell clones from the donor," N. Engl. J. Med. 333:1038-1044 (1995).
Wang et al., "Attenuated Poxviruses Generate Clinically Relevant Frequencies of CMV-Specific T cells," Blood. (104):847-856 (2004).
Wang et al., "Recombinant modified vaccinia virus Ankara expressing a soluble form of glycoprotein B causes durable immunity and neutralizing antibodies against multiple strains of human cytomegalovirus," J.Virol. (78):3965-3976 (2004).
Wang et al., "Human cytomegalovirus UL131 open reading frame is required for epithelial cell tropism," J.Virol. (79):10330-10338 (2005).
Wang et al., "Human cytomegalovirus virion protein complex required for epithelial and endothelial cell tropism," Proc.Natl.Acad. Sci.U.S.A (102):18153-18158 (2005).
Wang et al., "Attenuated poxvirus expressing three immunodominant CMV antigens as a vaccine strategy for CMV infection," J Clin Virol. (35):324-331 (2006).
Wang, D., et al., "Human cytomegalovirus uses two distinct pathways to enter retinal pigmented epithelial cells," PNAS 104(50):20037-20042 (2007).
Wang et al., "Vaccine properties of a novel marker gene-free recombinant modified vaccinia Ankara expressing immunodominant CMV antigens pp65 and IE1," Vaccine (25):1132-1141 (2007).

Wang et al., "A fusion protein of HCMV IE1 exon4 and IE2 exon5 stimulates potent cellular immunity in an MVA vaccine vector," Virology (377):379-390 (2008).
Wang et al., "Modified H5 promoter improves stability of insert genes while maintaining immunogenicity during extended passage of genetically engineered MVA vaccines," Vaccine (28):1547-1557 (2010).
Wang et al., "Quantitative analysis of neutralizing antibody response to human cytomegalovirus in natural infection," Vaccine. (29):9075-9080 (2011).
Wen, Y., et al., "Human cytomegalovirus gH/gL/UL 128/UL 130/UL 131A complex elicits potently neutralizing antibodies in mice," Vaccine 32:3796-3804 (2014).
Werner et al., "Studies on poxvirus infection in irradiated animals," Arch Virol 64:247-56 (1980).
White et al., "The IE2 60-kilodalton and 40-kilodalton proteins are dispensable for human cytomegalovirus replication but are required for efficient delayed early and late gene expression and production of infectious virus," J. Virol. 81:2573-2583 (2007).
Wilck et al., "Interim Analysis of a Phase 2 Trial of TransVax™, aTherapeutic DNA Vaccine for Control of Cytomegalovirus in Transplant Recipients," [abstract]. ICAAC (2010).
Wille et al., "A human cytomegalovirus gO-null mutant fails to incorporate gH/gL into the virion envelope and is unable to enter fibroblasts and epithelial and endothelial cells," J.Virol. (84):2585-2596 (2010).
Wills et al., "The human CTL response to cytomegalovirus is dominated by structural protein pp65: frequency, specificity, and T cell receptor usage of pp65-specific CTL," J. Virol. 70:7560-7579 (1996).
Wloch et al., "Safety and immunogenicity of a bivalent cytomegalovirus DNA vaccine in healthy adult subjects," J Infect Dis.(197):1634-1642 (2008).
Wussow et al., "A vaccine based on the rhesus cytomegalovirus UL128 complex induces broadly neutralizing antibodies in rhesus macaques," J Virol. 87(3):1322-1332 (2013).
Wussow, F., et al., "Human cytomegalovirus vaccine based on the envelope gH/gL pentamer complex," PLoS Pathog. 10(11):e1004524 (2014).
Wyatt et al., "Correlation of immunogenicities and in vitro expression levels of recombinant modified vaccinia virus Ankara HIV vaccines," Vaccine 26:486-93 (2008).
Wyatt et al., "Elucidating and minimizing the loss by recombinant vaccinia virus of human immunodeficiency virus gene expression resulting from spontaneous mutations and positive selection," J.Virol. (83):7176-7184 (2009).
Wyatt et al., "Development of a replication-deficient recombinant vaccinia virus vaccine effective against parainfluenza virus 3 infection in an animal model," Vaccine 14:!451-58 (1996).
Wyatt et al., "Enhanced cell surface expression, immunogenicity and genetic stability resulting from a spontaneous truncation of HIV Env expressed by a recombinant MVA," Virology 372(2):260-72 (Epub Nov. 28, 2007) (2007).
Wyatt et al., "Multiprotein HIV type 1 clade B DNA and MVA vaccines: construction, expression, and immunogenicity in rodents of the MVA component," AIDS Res. Hum. Retrovi. 20:645-653 (2004).
Yamada et al., "Characterization of the guinea pig cytomegalovirus genome locus that encodes homologs of human cytomegalovirus major immediate-early genes, UL128, and UL130," Virology (391):99-106 (2009).
Yamamoto-Tabata, T., et al., "Human cytomegalovirus interlukin-10 downregulates metalloproteinase activity and impairs endothelial cell migration and placental cytotrophoblast invasiveness in vitro," J. Viral. 78(6):2831-2840 (2004).
Yu et al., "Functional map of human cytomegalovirus AD169 defined by global mutational analysis," Proc Natl Acad Sci U S A. (100):12396-12401 (2003).

(56) References Cited

OTHER PUBLICATIONS

Yue et al., "Antibody responses to rhesus cytomegalovirus glycoprotein B in naturally infected rhesus macaques," J.Gen.Virol. (84):3371-3379 (2003).
Yue et al., "Immunogenicity and protective efficacy of DNA vaccines expressing rhesus cytomegalovirus glycoprotein B, phosphoprotein 65-2, and viral interleukin-10 in rhesus macaques," J. Virol. 81:1095-1109 (2007).
Yue et al., "Rhesus cytomegalovirus a nonhuman primate model for the study of human cytomegalovirus," Adv.Virus Res. (72):207-226 (2008).
Yue et al., "Evaluation of recombinant modified vaccinia Ankara virus-based rhesus cytomegalovirus vaccines in rhesus macaques," Med. Microbiol. Immunol. (197):117-123 (2008).
Zaia, "Status of cytomegalovirus prevention and treatment in 2000," Hematology 2000:339-355 (2001).
Zaia et al., "Prevention and management of CMV-related problems after hematopoietic stem cell transplantation," Bone Marrow Transplant. 29:633-638 (2002).
Zhang et al., "Detection of cytomegalovirus infection during clinical trials of glycoprotein B vaccine," Vaccine (23):507-510 (2004).
Zhang, C., "Hybridoma technology for the generation of monoclonal antibodies," Meth. Mal. Biol. 901:117-135 (2012).
Zhang et al., "Detection of cytomegalovirus infection during a vaccine clinical trial in healthy young women: seroconversion and viral shedding," J.Clin.Virol. (35):338-342 (2006).
Zhang et al., "Direct comparison of antigen production and induction of apoptosis by canarypox virus- and modified vaccinia virus Ankara human immunodeficiency virus vaccine vectors," J. Virol. 81:7022-7033 (2007).
Zhou, M., et al., "Human cytomegalovirus gH/gL/gO promotes the fusion step of entry into all cell types, whereas gH/gL/UL 128-131 broadens virus tropism through a distinct mechanism," J. Viral. 89(17):8999-9009 (2015).
Zydek, M., et al., "HCMV infection of human trophoblast progenitor cells of the placenta is neutralized by a human monoclonal antibody to glycoprotein B and not by antibodies to the pentamer complex," Viruses 6:1346-1364 (2014).
United States Patent and Trademark Office, International Search Report and Written Opinion dated Aug. 30, 2013 for PCT/US2013/032554.
Japanese Patent Office, Office Action dated Dec. 5, 2017 for Japanese patent application No. J015-524249 with English translations, 8 pages.
Schleiss, M. R., et al., "Could Therapeutic Vaccination of Cytomegalovirus-Seropositive Persons Prevent Reinfection and Congenitla Virus Transmission?" J. Infect. Dis. 203:1513-1516 (2011).

FIG. 2A
FIG. 2B
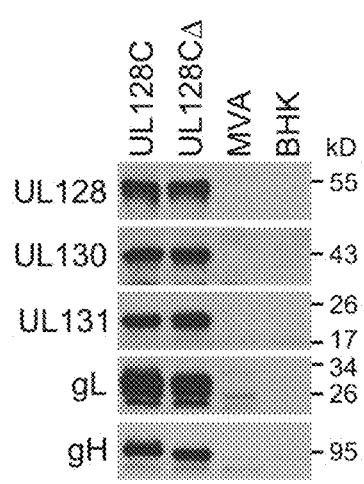
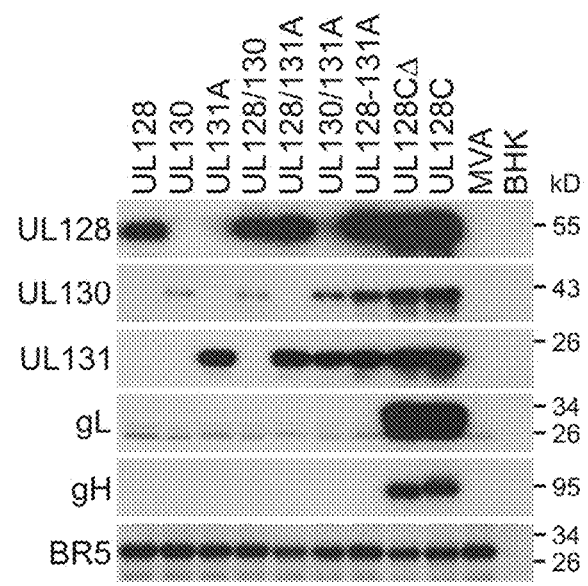

FIG. 11A
FIG. 11B
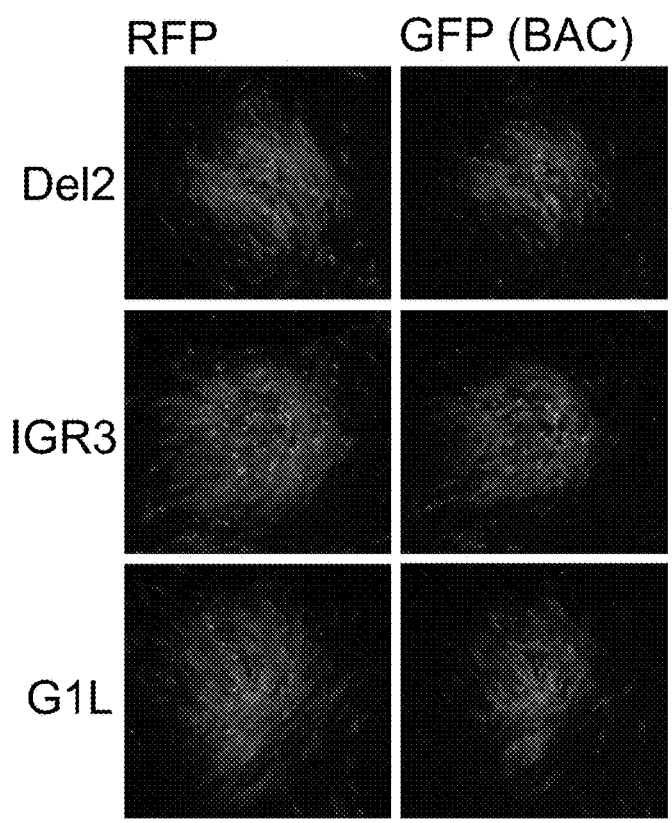

MVA VACCINE FOR DELIVERY OF A UL128 COMPLEX AND PREVENTING CMV INFECTION

PRIORITY CLAIM

This application is a continuation of U.S. patent application Ser. No. 14/606,973, filed Jan. 27, 2015, issuing as U.S. Pat. No. 9,913,897 on Mar. 13, 2018, which is a continuation of International Application No. PCT/US2013/032554, filed Mar. 15, 2013, which claims the benefit of U.S. Provisional Patent Application No. 61/676,846, filed Jul. 27, 2012, which is incorporated herein by reference in its entirety.

STATEMENT OF GOVERNMENT INTEREST

The present invention was made with government support under Grant No. AI063356, awarded by the National Institute of Allergy and Infectious Diseases; and Grant No. CA030206, awarded by the National Cancer Institute. The Government has certain rights in the invention.

BACKGROUND

Cytomelgalovirus (CMV) genomes are large (>200 kbp), and human CMV (HCMV) encodes ≥165 open reading frames (ORF) that encode proteins that enable it to infect multiple cell types, establish and reactivate from latency, and maintain a lifelong persistence in immune competent hosts (Murphy et al. 2003; Barry & Chang 2007; Hansen et al. 2003; Jarvis & Nelson 2007; Rivailler et al. 2006; Schleiss et al. 2008; Oxford et al. 2008). More than 60% of ORFs are non-essential for HCMV replication in fibroblasts (Dunn et al. 2003; Yu et al. 2003), suggesting that the function of most HCMV ORFs are only observed in cells other than fibroblasts and/or in vivo. A broader understanding of HCMV should include studies involving ORFs and their relevant cell types other than fibroblasts, the role these cells play in HCMV transmission, and the use of the appropriate animal models.

Endothelial and epithelial cells (together, "Epi/EC") are important cell types for HCMV infection and transmission. Following hematogenous spread from the primary infection site, HCMV infects Epi/EC cells of tissues that are important for horizontal transmission such as kidney, salivary, and mammary glands (Sinzger et al. 2008). Multiple studies have documented that virus can be excreted in saliva and urine long after resolution of a primary infection and in breast milk during successive pregnancies and lactations (Schleiss 2006a; Britt 2008; Wang et al. 2008; Mansat et al. 1997; Stagno et al. 1975). During vertical transmission, HCMV transits from uterine blood vessels to cytotrophoblast progenitor cells, and Epi/EC of the chorionic villus of the placenta are the first fetal cells infected by HCMV (Maidji et al. 2006; Maidji et al. 2002). Because Epi/EC play an important role in both horizontal and vertical transmission, protective efficacy of an HCMV vaccine will likely depend on success generating high titer neutralizing antibodies (NAb) against antigenic HCMV proteins that prevent infection of this cell type.

HCMV is a significant source of morbidity and mortality in individuals without a functional immune system, such as transplant recipients, those coinfected with HIV, or congenitally infected fetuses/neonates. Currently, there is no approved vaccine to prevent HCMV infection and/or disease, however, the Institute of Medicine of the National Academy of Sciences issued a report in the year 2000 placing the development of a HCMV vaccine in the highest priority category because of the improvements to human health such a vaccine would bring. Therefore, it would be beneficial to develop a vaccine that targets viral antigens (Ags) that mediate infection of Epi/EC and fibroblast cells.

SUMMARY

In one embodiment, an expression system for expressing a UL128 complex (UL128C; which includes UL128, UL130, UL131A, glycoprotein H, glycoprotein L) is provided herein. The expression system may include a bacterial artificial chromosome (BAC) construct, wherein the BAC construct comprises a viral vector inserted with a set of DNA sequences that encode a UL128C.

In another embodiment, a vaccine composition for preventing HCMV infection is provided. The vaccine composition may include a viral vector capable of expressing a UL128C and a pharmaceutically acceptable carrier, adjuvant, additive or combination thereof.

In another embodiment, a method of preventing HCMV entry into a cell is provided. Such a method may include contacting the cell with an effective amount of a viral vector, the viral vector comprising a set of DNA sequences that encode a UL128C.

In another embodiment, a method for treating a HCMV infection in a subject is provided. Such a method may include administering a therapeutically effective amount of a HCMV vaccine to the subject, wherein the HCMV vaccine comprises a viral vector capable of expressing UL128C, and a pharmaceutically acceptable carrier, adjuvant, additive (e.g. CD40L) or combination thereof.

According to some of the embodiments described above, the viral vector is a modified vaccinia Ankara (MVA) and the UL128C includes a set of five HCMV proteins or antigenic fragments thereof: UL128, UL130, UL131A, glycoprotein L (gL), and glycoprotein H (gH). In some embodiments, the viral vector is further inserted with one or more additional DNA sequences that encode one or more additional HCMV proteins or antigenic fragments thereof such as pp65, gB. These additional proteins could be either the dominant targets of cell-mediated immunity such as pp65 and IE1 or other important entry mediators that stimulate NAb such as glycoproteins gB, gM, gN, or gO.

BRIEF DESCRIPTION OF THE DRAWINGS

FIG. 1A shows a scheme for the insertion of a pox virus gene expression cassette into the MVA-BAC by En passant mutagenesis. First, a transfer construct is generated that comprises the gene sequence with upstream vaccinia virus mH5 promoter, downstream transcription terminal signal (TS), and a gene internal I-Scel restriction site and Kanamycin resistance ($Kan^R$) marker, both flanked by 50 bp gene duplication (stippled boxes). The construct is then amplified via PCR and inserted by Red recombination into the MVA-BAC utilizing homologous 50 bp primer extensions. Subsequently, the $Kan^R$ selection marker is seamlessly removed by I-Scel-expression-mediated introduction of a double-strand break at the I-Scel site and a subsequent second Red recombination of the 50 bp gene duplication. FIG. 1B shows the insertion sites (Del2, IGR3, G1L/I8R, BAC (B) vector ends in Del3) and the orientations of the RhCMV genes UL128, UL130, UL131A, gL and gH or gHΔTM in the MVA-BAC. The insertion order is indicated by numbers 1-5.

FIGS. 2A-B show Western blots (WBs) that detect co-expression of RhUL128C subunits expressed from MVA using rabbit polyclonal antisera. FIG. 2A shows WB analysis of total cell lysates of BHK cells infected with MVA-RhUL128C or MVA-RhUL128CΔ. FIG. 2B shows WB analysis of total cell lysates of CEF cells infected with MVA expressing different combinations of the RhUL128-UL131A subunits or with MVA-RhUL128C or MVA-RhUL128CΔ. Uninfected or MVA-infected cells were used as negative controls. For loading control, lysates were analyzed with monoclonal antibody 19C2 specific for vaccinia virus BR5 protein. Markers for protein sizes are given in kilo Dalton (kD).

FIGS. 6A and 6B) Shown are the NT50 titers measured on monkey kidney epithelial cells (MKE) two (6A) and six (6B) weeks post vaccination (Vx) for the indicated vaccine groups. FIGS. 6C and 6D) Shown are the NT50 titers measured two (6C) and six (6D) weeks post Vx on fibroblast (Telo-RF). The given values for MVA-RhgB- or MVA-venus-vaccinated RM measured on Telo-RF have already been published earlier (1) (asterisks). Medians are given by bars. The normative NT50 range measured on MKE or Telo-RF for naturally infected monkeys is indicated by dashed lines. Arrows indicate the detection limit of the assay. P-values comparing the MVA-RhUL128C vaccine group to the MVA-RhUL128CΔ vaccine group or to one of the other vaccine groups (RhUL128, RhUL130, RhUL128/UL130/UL131, RhgB, venus) were calculated by one-sided rank sum test. The p-values in C comparing either the MVA-RhUL128C or MVA-RhUL128CΔ vaccine group with the MVA-RhgB vaccine group were calculated by two-sided rank sum test.

FIGS. 11A-B illustrate the expression of HCMV inserts from MVA reconstituted from a 1974-MVA-BAC. In FIG. 11A, the expression of red fluorescent protein (RFP) is shown by fluorescence microscopy of single viral plaques of BHK-21 cells infected with MVA containing mRFP expression cassettes in Del2, IGR3, or G1L insertion sites. MVA also expresses GFP due to BAC vector construction (right side of Figure). In FIG. 11B, Western Blot analysis of CEF infected with MVA expressing human UL128 expressed from Del2, human UL131A expressed from IGR3, or human full length gH expressed from G1L. CEF infected with non-recombinant MVA were analyzed as a non-specific control. Proteins were detected with rabbit polyclonal antibody (UL131A) or mouse monoclonal antibody (UL128, gH).

FIGS. 12A and 12B) Shows the NAb titer (NT50) of Balb/C mice at different time points after immunization with the indicated MVA vaccines. Balb/C mice were immunized twice, 4 weeks apart and serum NAb titers were measured three weeks after each immunization at weeks 3 and 7 and additionally at week 20 after the first immunization. NAb titers were determined on human ARPE-19 epithelial cells (12A) and human foreskin fibroblasts (HFF-1) (12B) using HCMV strain VHL-1 for infection. FIG. 12C) Shows the neutralization activity 20 weeks after the first immunization against HCMV strains VHL-1, TB40/E, and TR on ARPE- 19 cells. Arrows adjacent to the y-axis in 12A, 12B, and 12C indicate the detection limit of the assay. The upper dotted line in 12A and 12C indicate the neutralization activity in pooled sera from HCMV-positive individuals against HCMV strain VHL-1 measured on ARPE-19 cells. The upper dotted line in 12B shows the neutralization activity in sera of HCMV-positive donors against the laboratory strain AD169 determined on fibroblasts

DETAILED DESCRIPTION

Figure 1A:
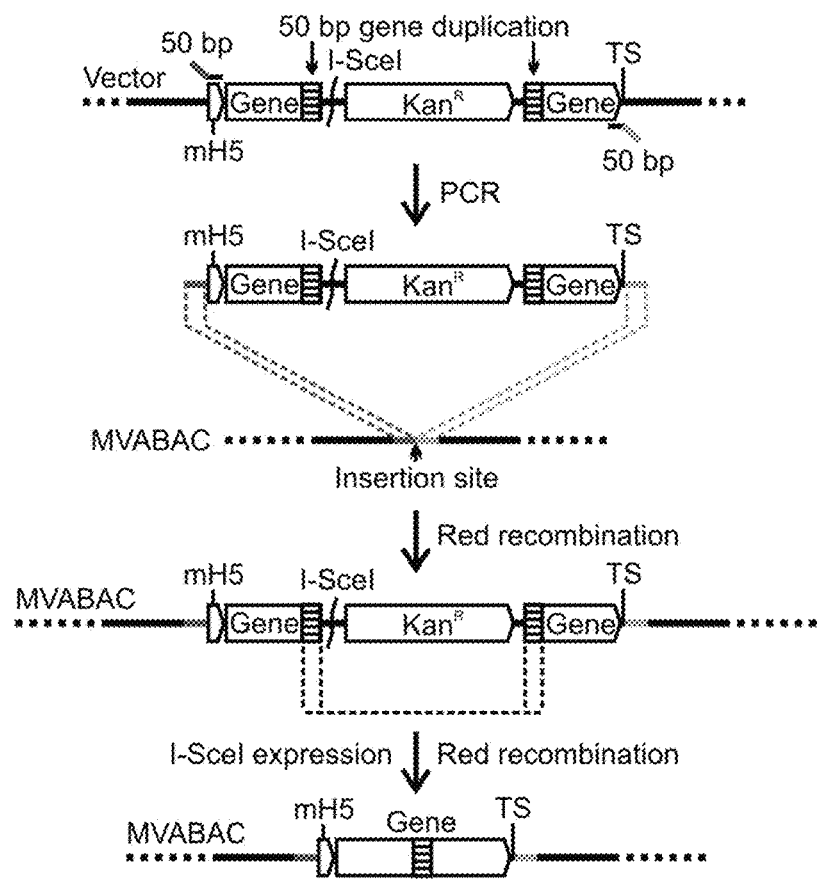
FIGS. 1A-B are a pair of schematics illustrating insertion of a gene expression cassette (FIG. 1A) and the insertion sites of the RhCMV genes (FIG. 1B) in the MVA-BAC according to some embodiments.

Expression systems and vaccines for use in preventing or treating HCMV infection are provided herein. The expression systems and vaccines, which are described in detail below, generate neutralizing antibodies (NAb) against HCMV antigenic proteins or fragments to block entry of the virus to its host cells, thereby preventing horizontal and vertical virus transmission.

Despite several decades of effort, HCMV vaccine development has remained an unsolved public health priority (Arvin et al. 2004; Stratton et al. 2001). Some progress has been made with a subunit vaccine based on glycoprotein B (gB) (Zhang et al. 2006; Zhang & Pass 2004). Pregnant women who develop high avidity anti-gB NAb during primary infection are less likely to have a congenitally infected child than women who do not generate high avidity gB antibodies (Boppana & Britt 1995). While the results highlight the importance of gB-NAb in limiting congenital infection, there are undefined factors associated with transplacental transmission. Some women who developed high avidity gB antibodies had fetuses with congenital infection, while there was no congenital transmission in women with low avidity antibodies (Boppana & Britt 1995).

Passive immunotherapy has been shown to protect a fetus from the devastating consequences of intrauterine infection. This suggests that a hyperimmune globulin can decrease the frequency of congenital infection, reduce placental thickening, and resolve signs of central nervous system disease (Adler & Nigro 2006; Adler et al. 2007; La Torre et al. 2006; Nigro et al. 2005; Nigro et al. 2008). Recent findigs have demonstrated that the majority of CMV hyperimmune globulin NAb are directed against UL128C (Fouts et al. 2012).

Attenuated HCMV Towne vaccine ("Towne"), derived after repeated passage on human fibroblasts (Plotkin et al. 1975), elicits NAb to prevent HCMV fibroblast-entry and cellular immune responses to viral antigens (Gonczol & Plotkin 2001). Immunization with Towne protects against low dose HCMV (Plotkin et al. 1989) challenge and partially protects HCMV-negative renal transplant recipients from severe post-transplant HCMV disease (Plotkin et al. 1991). Although Towne stimulated lymphoproliferative responses comparable to exposure to wild-type virus, NAb titers were 10 to 20-fold lower than observed after natural infection measured in Fibroblasts. The Towne strain suffered genomic changes during propagation on human fibroblasts, including mutation of the UL130 protein that destabilizes cell-surface expression of UL128C (Patrone et al. 2005) (see below). Similar to the potential limitations of gB vaccine (Sinzger et al. 2008; Cui et al. 2008), absence of NAb to CMV antigens specific to Epi/EC may limit Towne's protective efficacy. Therefore, it is likely that Towne is too attenuated to stimulate robust immunity, attributable to minimal in vivo replication and lack of persistence or evidence of latency. Accordingly, chimeric vaccine strains between Towne and a natural isolate (Toledo) were used in Phase I studies to boost replication while maintaining virulence (Heineman et al. 2006).

HCMV-based vaccines may also be limited by immune evasion leading to super-infection of HCMV-positive women by an unrelated HCMV strain resulting in congenital infection (Boppana et al. 2001). A DNA vaccine strategy comprised of pp65 and gB Antigen has been tested in a transplant setting, yet gB-specific antibody levels were minimally stimulated and levels were not considered high enough to be protective against progressive infection (Wilck et al. 2010; Wloch et al. 2008; Kharfan-Dabaja et al. 2012).

A phase II trial evaluating recombinant gB admixed in the adjuvant MF59 (gB/MF59) showed 50% efficacy to prevent primary HCMV infection of seronegative women who had given birth within the previous year (Pass et al. 1999; Pass et al. 2009). In contrast, live-attenuated HCMV Towne strain ("Towne") failed in an earlier trial to protect seronegative mothers with at least one HCMV-shedding child from acquiring primary HCMV infection (Adler et al. 1995). These results offer encouragement that vaccines directed at neutralizing epitopes can significantly decrease the rate of primary infection in HCMV-negative women. Nevertheless, the absence of complete protection in both trials suggests that additional non-gB-encoded neutralizing epitopes should be targeted to eliminate the risk of primary infection in the mother and congenital infection in the fetus. In particular, epitopes that would induce NAb to block HCMV infection of the Epi/EC cell lineages should be included in CMV vaccines as described below.

Following a primary infection of a cell or a population of cells at a mucosal surface, HCMV spreads via the blood to multiple body organs. HCMV has broad cell tropism for infection, including Epi/EC, fibroblasts, macrophages (Sinzger et al. 2007; Plachter et al. 1996), and cytotrophoblasts (Maidji et al. 2006; Maidji et al. 2002). Viral entry into different cell types requires different gH and gL envelope glycoprotein complexes (gH/gL) (Sinzger & Jahn 2008; Vanarsdall & Johnson 2012). Nevertheless, because of their ease of use, culture of HCMV and quantification of NAb titers has typically been investigated using fibroblasts.

Studies based on neutralization of fibroblast infection using tissue culture-adapted HCMV strains (e.g. AD169 or Towne) have identified glycoprotein B (gB), glycoprotein H (gH) and glycoprotein M (gM) and glycoprotein N (gN) complexes (gM/gN) as major NAb targets (Adler et al. 1998; Britt et al. 1990; Marshall et al. 1994; Rasmussen et al. 1991; Shimamura et al. 2006). gB elicits the majority of antibodies found in immune individuals that neutralize fibroblast infection by blocking gB-mediated fusion between the virion and the cell membrane (Kinzler & Compton 2005; Navarro et al. 1993; Britt 1984; Britt et al. 1988; Gonczol et al. 1990; Liu et al. 1991). However, like the vaccination studies described above, fibroblast-based neutralization studies incompletely define NAb responses to HCMV infection. This is likely due to a failure to prevent infection of Epi/EC, as the neutralization studies have not detected NAb that block infection of Epi/EC.

The genomes of human CMV (HCMV) and Rhesus CMV (RhCMV) are largely colinear (Hansen et al. 2003; Rivailler et al. 2006), and like HCMV, the UL/b' virulence region of RhCMV has been shown to undergo rearrangements following culture passage leading to deletion of multiple open reading frames (ORFs) (Oxford et al. 2008). While HCMV entry into fibroblasts depends on gB, gM/gN and complexes formed from glycoprotein H, glycoprotein L and glycoprotein O (gH/gL/gO), three ORFs in the UL/b' region, UL128, UL130, and UL131A, are required for entry into Epi/EC. UL128, UL130, and UL131A form a pentameric virion protein complex with gH/gL, called UL128C, which mediates low pH-dependent endocytic entry into Epi/EC, which is distinct from viral fusion with fibroblasts described above (Hahn et al. 2004; Isaacson & Compton 2009; Ryckman et al. 2010; Ryckman et al. 2008a, b; Vanarsdall et al. 2008; Wang & Shenk 2005b; Wille et al. 2010).

The AD169 and Towne CMV strains have lost the ability to infect Epi/EC due to mutations in the UL128-UL131A locus (Murphy et al. 2003; Wang & Shenk 2005a). Consequently, their restricted cell tropism makes these viruses unsuitable for quantifying NAb that inhibit Epi/EC infection. Use of HCMV clinical strains with intact cell tropism has shown that HCMV-infected individuals develop NAb to UL128C that potently block infection of Epi/EC (Genini et al. 2011; Macagno et al. 2010). In addition, studies with AD169 repaired for UL128, UL130 and UL131A have shown that gB/MF59 and Towne fail to induce Epi/EC-specific NAb titer comparable to those observed during natural infection (Cui et al. 2008). These results provide strong evidence that UL128C is an important determinant of NAb activity specific for Epi/EC (Cui et al. 2008; Gerna et al. 2008). Thus, one approach to minimizing the dissemination of challenge virus beyond mucosal surfaces is to target these proteins by vaccination to prevent the spread of primary infection (see Wussow et al, 2013, shows NAb blocking of Epi/EC and fibroblast infection by UL128C vaccination).

Clinical translation of a CMV vaccine is facilitated by studies in rhesus macaques (RM) which is considered as the model that is most directly relevant to humans. It was previously demonstrated that immunization of RhCMV-negative RM with MVA expressing RhgB induces fibroblast-specific NAb and reduces RhCMV challenge virus in plasma (Abel et al. 2011; Yue et al. 2008; Yue et al. 2003). In addition, a trivalent MVA vaccine composed of RhgB and the two dominant targets of cell-mediated immunity, phosphoprotein 65 (Rhpp65) and immediate-early 1 (RhIE1) reduced shedding in 50% of the vaccinated animals (Abel et al. 2011). Building on studies that the HCMV UL128C pentamer is needed for Epi/EC entry and is an important target of NAb, the studies described in the Examples below show that vaccination of RM with MVA-expressing RhCMV UL128C (RhUL128C) elicits NAb inhibiting RhCMV infection of rhesus Epi/EC as well as rhesus fibroblasts. This approach is supported by a study that showed that restoration of UL128, UL130 and UL131A in RhCMV variants lacking these ORFs restores epithelial tropism (Lilja & Shenk 2008). In addition, immunization of RM or rabbits using AD169 with repaired UL130 gene and restored UL128C pentamer formation leads to significantly increased neutralization activity that inhibits HCMV infection of ARPE-19 epithelial cells when compared to immunization with parental AD169 (Fu et al., 2012). The studies described below in RhCMV-negative RM using RhCMV UL128C as a prophylactic vaccine to elicit NAb justified construction of an HCMV equivalent that could prevent multiple entry routes of CMV infection. Analogous HCMV UL128C and gB-based vaccines may also be constructed and assessed to elicit NAb that prevents in vitro infection by virulent clinical HCMV isolates. Such a vaccine may be even more effective at neutralizing HCMV infection in both endocytic and fibroblast pathways of infection.

Figure 12A:
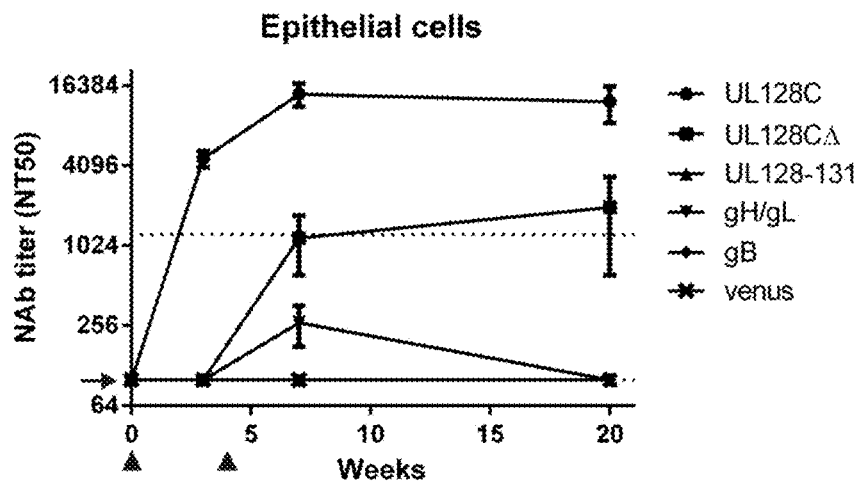
FIGS. 12A-C show NAb titers in vaccinated Balb/C mice.

Assembled forms of the HCMV UL128C pentamer along with sub-species representing individual components were expressed in MVA as described herein, and at least in paragraphs [0005], [0010], [0017], and [0018]. These combinations of antigens include gH and gL; UL128, UL130, and UL131; UL128C with full length gH; and UL128CΔ with transmembrane-deleted gH. In addition, gB and venus were inserted into MVA separately and evaluated similarly to UL128C subunits in Balb/C mice. Briefly, these experiments consisted of two rounds of immunization separated by 4 weeks and blood draws obtained at baseline 3, 7, and 20 weeks. Remarkably, in mice immunized with UL128C the NT50 NAb titers measured on ARPE-19 epithelial cells against the HCMV strain VHL-1 catapulted to 4096 after one immunization, and increased ~3-fold after the second immunization while maintaining activity only slightly below the highest level at a 20-week time point (FIG. 12A). A parallel, but far lower amount was found after the second immunization when the UL128CΔ strain was used while only a very transitory and relatively low level of NAb were found using the gH/gL-MVA and only background recognition when using either the gB-MVA or the Venus-MVA (FIG. 12A). The route of infection was intraperitoneal, which may have influenced the level of NAb, since it has been described that subcutaneous or intramuscular injection of MVA can lead to increased NAb titer. Nonetheless, there is a distinct difference between all the other constructs and UL128C possessing full-length gH regarding induction of neutralization activity in Balb/C mice.

Figure 12B:
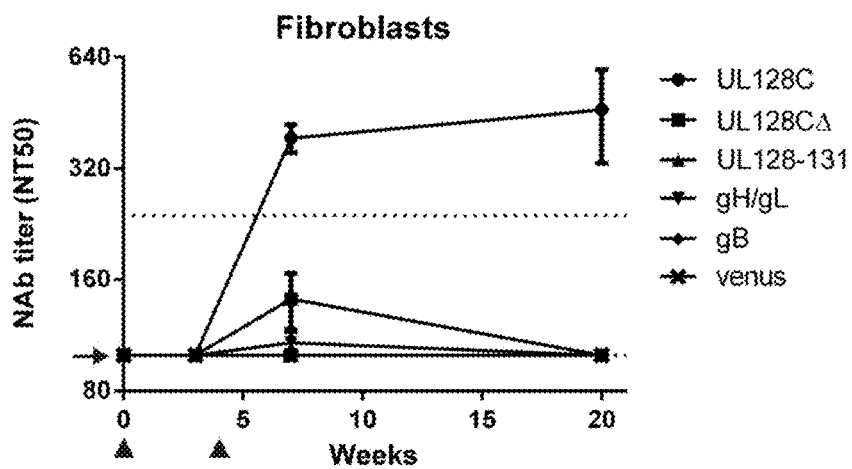

Surprisingly, NAb titer measured on HFF-1 fibroblast cells in sera derived from MVA-UL128C-vaccinated mice were also significantly higher than that determined for all other groups (FIG. 12B). These results were unexpected since the UL128C has never previously been described in the literature as a target of NAb which prevent HCMV infection of fibroblasts. While there was no neutralization activity detectable in the MVA-UL128C vaccine group after the first immunization, the NAb titer increased to 387 after the second immunization, and increased even slightly at week 20. Low NAb titer was also determined in mice immunized with MVA-UL128CΔ or MVA expressing gH/gL after the second immunization, though at week 20 the NAb titer dropped under the detection limit of the assay for both vaccines. Furthermore, the neutralization activity induced in mice vaccinated with MVA co-expressing UL128-UL131, MVA-gB680 or venus remained undetectable throughout the 20 weeks. Again, the immunization route may have been sub-optimal for the induction NAb. However, these results provide strong evidence that the UL128C pentamer is superior to gB or any combination of less than all 5 UL128C subunits for the induction of neutralization activity that inhibits both Epi/EC and fibroblast infection.

Figure 12C:
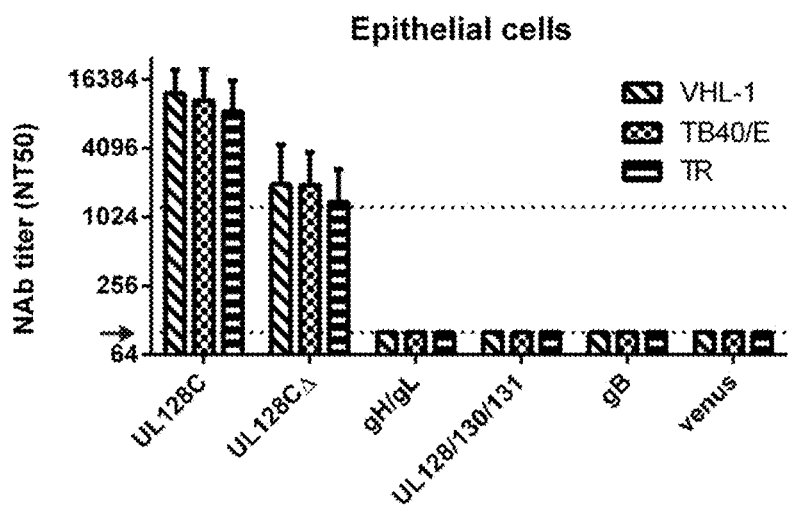

In addition, the potent neutralization activity measured on ARPE-19 cells in sera from MVA-UL128C-vaccinated Balb/c of week 20 was not only effective against VHL-1 virus, it was equally effective against the HCMV strains TB40/E and TR (FIG. 12C). The determined titers for the individual viruses were comparable to each other. NAb titer in sera from mice vaccinated with MVA-UL128CΔ determined for the three different viruses on ARPE-19 cells were also comparable to each other, but significantly lower than that measured in sera from MVA-UL128C vaccinated mice. No neutralization activity was confirmed in mice immunized with MVA expressing gH/gL, UL128-UL131A, gB, or venus. These data provide strong evidence that vaccination with the UL128C pentamer induces broadly neutralization activity.

Based on the studies described above, expression systems, viral vectors and vaccines that may be used in methods for inhibiting of HCMV entry into Epi/EC, fibroblasts, or both, have been developed and described herein.

CMV Antigenic Expression Systems and Vaccines

According to the embodiments described herein, an HCMV antigenic protein expression system (or "antigen expression system") is provided herein. In one embodiment, the antigen expression system may include a cloning vector to clone an expression vector that is able to express one or more HCMV antigenic proteins or antigenic fragments thereof.

In one embodiment, the cloning vector is a BAC, which is a DNA construct that may be used to clone one or more target HCMV genes by transformation in bacteria (e.g., *E. coli*). The use of BAC as a cloning vector allows for stable cloning of very large DNA sequences, and can be easily manipulated using genetic techniques established for *E. coli*. In some embodiments, the BAC cloning vector is used to clone an expression vector. The expression vector may be a plasmid, a BAC, a viral vector (e.g., adenoviral vectors, adeno-associated viral vectors, RNA viral vectors, lentiviral vectors or retroviral vectors), a viral vector constructed as a BAC, or any other suitable vector that is able to express a recombinant protein, a viral vector or both.

In some embodiments, the expression vector (e.g., the viral vector) is capable of expressing one or more immunogenic or antigenic HCMV proteins or functional fragments thereof. An immunogenic protein is a protein that, when introduced to a subject, is recognized by the subject's immune cells, thereby stimulating an immune reaction. The immune reaction may result in antibody production (e.g., neutralizing antibody production) against that protein. A functional or antigenic fragment of an immunogenic protein is any portion of the protein that contains an antigenic portion of the protein or is an antigenic portion of the protein which may contain at least one epitope. In some embodiments, the one or more immunogenic proteins or functional fragments thereof may be an immunogenic protein complex, which includes a set of immunogenic protein subunits or functional fragments thereof.

In one embodiment, the BAC cloning vector is used to clone a viral expression vector. In such embodiments, the genome of the viral expression vector is inserted into a BAC construct to generate a virus-BAC construct or plasmid. A bacterial host (e.g., *E. coli*) is then transfected with the virus-BAC plasmid to clone the viral vector. Transfection of the virus-BAC clones into eukaryotic cells susceptible to infection by the viral vector results in reconstitution of the recombinant virus. The resulting reconstituted viral vectors may then be used to infect target tissues or cells in a host.

In some embodiments, the viral vector may be derived from any suitable poxvirus including, but not limited to, Avipoxvirus (e.g., canarypox virus and related strains such as ALVAC; fowlpox virus), Orthopoxvirus (e.g., vaccinia virus strains such as the Western Reserve or Lister strain, Copenhagen strain (NYVAC), Dryvax strain, modified vaccinia Ankara (MVA) strain, ACAM1000, and ACAM2000 strain), Parapoxvirus (e.g., Orf virus), In one embodiment, the viral vector is a modified vaccinia Ankara (MVA), which is cloned into the BAC cloning vector ("MVA-BAC") and is able to express one or more immunogenic HCMV proteins or antigenic fragments thereof. Any suitable MVA strain may be cloned by a BAC in accordance with the embodiments described herein, including, but not limited to the 1974-MVA strain, VR strain or ACAM 3000 strain.

In one embodiment, one or more immunogenic HCMV proteins or antigenic fragments thereof is a set of immunogenic protein subunits or functional fragments thereof that are part of a UL128 complex (UL128C). The UL128 complex is a HCMV protein complex that includes the following five immunogenic protein subunits or functional fragments thereof: UL128, UL130, UL131A, gL, and gH. Co-expression of all five of the UL128C subunits is required in single cells to obtain functional expression (Patrone et al. 2005; Macagno et al. 2009). Therefore, a single delivery vector is needed (e.g. MVA see below), since there is no current generally acceptable approach to guide >1 individual DNA or viral vectors to assemble a protein complex in vivo by co-expression of all 5 UL128C components.

Expression of the UL128 complex that includes the UL128, UL130, UL131A, gL, and gH proteins or antigenic fragments thereof by the expression systems and viral vectors described herein results in stimulation of neutralizing antibodies (NAb) by a host's immune system that block HCMV infection in susceptible cells such as epithelial and endothelial cells.

In other embodiments, the expression vector may include additional HCMV proteins including, but not limited to, pp65, gB, IE1 gM, gN, gO, and other suitable antigenic HCMV proteins known in the art. These additional genes may be inserted into a first expression vector with the UL128C subunits, or alternatively, may be inserted into a second expression vector to be administered in combination with the first expression vector.

According to the embodiments described herein, an immunization regimen is provided. The immunization regimen may include administering one or more priming vectors or vaccines, followed by administering one or more boosting vectors or vaccines. A priming vector may be any suitable expression vector that includes the HCMV or RhCMV UL128C subunits described in the MVA vector above. In one embodiment, the priming vector may be a vector which includes naked plasmid DNA which incorporates the same HCMV or RhCMV UL128C subunits as the MVA vector described herein. Additional priming vectors or vaccinations may include viral vectors, bacterial vectors, or other delivery vehicles, either live or synthetic, administered prior to MVA immunization. The priming immunization may be administered once, or may be administered as a multi-dose (e.g., one, two, three, four, or more) priming immunization regimen which may include a series of priming immunizations, administered in a schedule that may vary from 1 to 4 weeks between inoculations. For example, the priming immunizations may be administered either once, twice, or three times in a regimen or schedule that can vary from 1 to 4 weeks between inoculations.

In other embodiments, the MVA vector described above may be a priming immunization. In such a case, the aforementioned primes can also be used as booster vectors after one or more (e.g., one, two, three, four, or more) consecutive MVA immunizations. Alternatively, priming and boosting vectors can alternate such that the heterologous immunization will include an MVA or alternate vector as a prime followed by MVA or an alternate vector as a boost from 1 to 4 times as an example. Other suitable immunization schedules or regimens that are known in the art may be used according to the embodiments described herein by those skilled in the art.

According to some embodiments, the alternate vectors, such as the naked plasmid DNA described above, may be assembled such that all UL128C subunits are assembled into a single vector. Alternately, the UL128C subunits may be assembled into several distinct copies of a base expression vector, which may be a plasmid, viral, or bacterial vector. In addition, UL128C subunits may be inserted in separate locations or linked through linkers known as internal ribosome entry sites (IRES), derived from a number of different RNA viruses that are well known in the art to link all or a portion of the subunits in one insertion site or multiple insertion sites. One such linker is referred to as 2A or a similar linker from a related virus called T2A that may be used to link the UL128C subunit together into one polycistronic messenger RNA that can be translated and processed into multiple distinct proteins.

A recombinant vector, such as the MVA viral vector described above; or any other suitable alternative vector including suitable primer or booster vectors described above, may be part of a HCMV vaccine composition that may be used in methods to treat or prevent HCMV infection. A HCMV vaccine composition as described herein may comprise a therapeutically effective amount of a recombinant viral vector as described herein, and further comprising a pharmaceutically acceptable carrier according to a standard method. Examples of acceptable carriers include physiologically acceptable solutions, such as sterile saline and sterile buffered saline.

In some embodiments, the vaccine or pharmaceutical composition may be used in combination with a pharmaceutically effective amount of an adjuvant to enhance the anti-CMV effects. Any immunologic adjuvant that may stimulate the immune system and increase the response to a vaccine, without having any specific antigenic effect itself may be used as the adjuvant. Many immunologic adjuvants mimic evolutionarily conserved molecules known as pathogen-associated molecular patterns (PAMPs) and are recognized by a set of immune receptors known as Toll-like Receptors (TLRs). Examples of adjuvants that may be used in accordance with the embodiments described herein include Freund's complete adjuvant, Freund's incomplete adjuvant, double stranded RNA (a TLR3 ligand), LPS, LPS analogs such as monophosphoryl lipid A (MPL) (a TLR4 ligand), flagellin (a TLR5 ligand), lipoproteins, lipopeptides, single stranded RNA, single stranded DNA, imidazoquinolin analogs (TLR7 and TLR8 ligands), CpG DNA (a TLR9 ligand), Ribi's adjuvant (monophosphoryl-lipid A/trehalose dicorynoycolate), glycolipids (α-GalCer analogs), unmethylated CpG islands, oil emulsion, liposomes, virosomes, saponins (active fractions of saponin such as QS21), muramyl dipeptide, alum, aluminum hydroxide, squalene, BCG, cytokines such as GM-CSF and IL-12, chemokines such as MIP 1-α and RANTES, activating cell surface ligands such as CD40L, N-acetylmuramine-L-alanyl-D-isoglutamine (MDP), and thymosin al. The amount of adjuvant used can be suitably selected according to the degree of symptoms, such as softening of the skin, pain, erythema, fever, headache, and muscular pain, which might be expressed as part of the immune response in humans or animals after the administration of this type of vaccine.

In further embodiments, use of various other adjuvants, drugs or additives with the vaccine of the invention, as discussed above, may enhance the therapeutic effect achieved by the administration of the vaccine or pharmaceutical composition. The pharmaceutically acceptable carrier may contain a trace amount of additives, such as substances that enhance the isotonicity and chemical stability. Such additives should be non-toxic to a human or other mammalian subject in the dosage and concentration used, and examples thereof include buffers such as phosphoric acid, citric acid, succinic acid, acetic acid, and other organic acids, and salts thereof; antioxidants such as ascorbic acid; low molecular weight (e.g., less than about 10 residues) polypeptides (e.g., polyarginine and tripeptide) proteins (e.g., serum albumin, gelatin, and immunoglobulin); amino acids (e.g., glycine, glutamic acid, aspartic acid, and arginine); monosaccharides, disaccharides, and other carbohydrates (e.g., cellulose and derivatives thereof, glucose, mannose, and dextrin), chelating agents (e.g., EDTA); sugar alcohols (e.g., mannitol and sorbitol); counterions (e.g., sodium); nonionic surfactants (e.g., polysorbate and poloxamer); antibiotics; and PEG.

The vaccine or pharmaceutical composition containing a recombinant viral vector described herein may be stored as an aqueous solution or a lyophilized product in a unit or multiple dose container such as a sealed ampoule or a vial.

Preventing HCMV Entry into a Cell, Treating HCMV, and Preventing HCMV Infection

The antigen expression system described above may be used in in vitro, in vivo or ex vivo methods of preventing HCMV entry into a cell or a population of cells. In some embodiments, methods for preventing HCMV entry into a cell or a population of cells include steps of contacting the cell or population of cells with an effective amount of a viral vector capable of expressing a UL128 complex or antigenic fragments thereof.

In other embodiments, methods for treating or preventing a HCMV infection in a subject are provided. Such methods may include administering a therapeutically effective amount of a HCMV vaccine to the subject. The HCMV vaccine may include at least one active ingredient, wherein the at least one active ingredient includes a viral vector that is capable of expressing a UL128 complex or antigenic fragments thereof, such as those described herein.

The expression systems and vaccines described herein may be used to treat or prevent any HCMV infection that infects epithelial cells, endothelial cells, fibroblasts or a combination thereof. Examples of HCMV infections that may be treated or prevented using the methods described herein may include, but is not limited to, congenital HCMV infection, opportunistic HCMV infections in subjects with compromised immune system (e.g., organ and bone marrow transplant recipients, cancer patients and chemotherapy recipients, patients receiving immunosuppressive drugs and HIV-infected patients) and silent HCMV infections in otherwise healthy subjects.

The term "effective amount" as used herein refers to an amount of a compound that produces a desired effect. For example, a population of cells may be contacted with an effective amount of a compound to study its effect in vitro (e.g., cell culture) or to produce a desired therapeutic effect ex vivo or in vitro. An effective amount of a compound may be used to produce a therapeutic effect in a subject, such as preventing or treating a target condition, alleviating symptoms associated with the condition, or producing a desired physiological effect. In such a case, the effective amount of a compound is a "therapeutically effective amount," "therapeutically effective concentration" or "therapeutically effective dose." The precise effective amount or therapeutically effective amount is an amount of the composition that will yield the most effective results in terms of efficacy of treatment in a given subject or population of cells. This amount will vary depending upon a variety of factors, including but not limited to the characteristics of the compound (including activity, pharmacokinetics, pharmacodynamics, and bioavailability), the physiological condition of the subject (including age, sex, disease type and stage, general physical condition, responsiveness to a given dosage, and type of medication) or cells, the nature of the pharmaceutically acceptable carrier or carriers in the formulation, and the route of administration. Further an effective or therapeutically effective amount may vary depending on whether the compound is administered alone or in combination with another compound, drug, therapy or other therapeutic method or modality. One skilled in the clinical and pharmacological arts will be able to determine an effective amount or therapeutically effective amount through routine experimentation, namely by monitoring a cell's or subject's response to administration of a compound and adjusting the dosage accordingly. For additional guidance, see Remington: The Science and Practice of Pharmacy, $21^{st}$ Edition, Univ. of Sciences in Philadelphia (USIP), Lippincott Williams & Wilkins, Philadelphia, Pa., 2005, which is hereby incorporated by reference as if fully set forth herein.

"Treating" or "treatment" of a condition may refer to preventing the condition, slowing the onset or rate of development of the condition, reducing the risk of developing the condition, preventing or delaying the development of symptoms associated with the condition, reducing or ending symptoms associated with the condition, generating a complete or partial regression of the condition, or some combination thereof. Treatment may also mean a prophylactic or preventative treatment of a condition.

In some embodiments, the vaccine or pharmaceutical composition described herein may be used in combination with other known pharmaceutical products, such as immune response-promoting peptides and antibacterial agents (synthetic antibacterial agents). The vaccine or pharmaceutical composition may further comprise other drugs and additives. Examples of drugs or additives that may be used in conjunction with a vaccine or pharmaceutical composition described herein include drugs that aid intracellular uptake of the recombinant virus or MVA or recombinant transgenic protein of the present invention, liposome and other drugs and/or additives that facilitate transfection, (e.g., fluorocarbon emulsifiers, cochleates, tubules, golden particles, biodegradable microspheres, and cationic polymers).

In some embodiments, the amount of the active ingredient contained in the vaccine or pharmaceutical composition described herein may be selected from a wide range of concentrations, Virus Particle Unit (VPU), Plaque Forming Unit (PFU), weight to volume percent (w/v %) or other quantitative measure of active ingredient amount, as long as it is a therapeutically or pharmaceutically effective amount. The dosage of the vaccine or pharmaceutical composition may be appropriately selected from a wide range according to the desired therapeutic effect, the administration method (administration route), the therapeutic period, the patient's age, gender, and other conditions, etc.

In some aspects, when a recombinant viral vector is administered to a human subject as an active ingredient of the vaccine or pharmaceutical composition, the dosage of the recombinant virus or MVA may be administered in an amount approximately corresponding to $10^2$ to $10^{14}$ PFU, preferably $10^5$ to $10^{12}$ PFU, and more preferably $10^6$ to $10^{10}$ PFU per patient, calculated as the PFU of the recombinant virus.

In further aspects, when a recombinant viral vector is administered to a subject as an active ingredient of the vaccine or pharmaceutical composition, the dosage may be selected from a wide range in terms of the amount of expressible DNA introduced into the vaccine host or the amount of transcribed RNA. The dosage also depends on the strength of the transcription and translation promoters used in any transfer vectors used.

In some embodiments, the vaccine composition or pharmaceutical composition described herein may be administered by directly injecting a recombinant viral vector suspension prepared by suspending the recombinant virus or MVA in PBS (phosphate buffered saline) or saline into a local site (e.g., into the lung tissue, liver, muscle or brain), by nasal or respiratory inhalation, or by intravascular (i.v.) (e.g., intra-arterial, intravenous, and portal venous), subcutaneous (s.c.), intracutaneous (i.c.), intradermal (i.d.), or intraperitoneal (i.p.) administration. The vaccine or pharmaceutical composition of the present invention may be administered more than once. More specifically, after the initial administration, one or more additional vaccinations may be given as a booster. One or more booster administrations can enhance the desired effect. After the administration of the vaccine or pharmaceutical composition, booster immunization with a pharmaceutical composition containing the recombinant virus or MVA as described herein may be performed.

Evaluations of HCMV vaccine trials, in vitro studies, and work in the RhCMV model described herein converge on the premise that the UL128 complex of proteins (UL128C; UL128, UL130, UL131A, gH, and gL) must be included in a vaccine formulation to interfere with an important portal of HCMV infection—endothelial and epithelial cells. The function of this protein complex is neutralized through immunization to block both dissemination from an infection site to distal sites and transmission of infectious virus from an infected host. UL128C alone or together with other vaccine candidate antigens, such a strategy provides a rational basis to significantly inhibit vertical and horizontal transmission of HCMV. Small animal models of HCMV (i.e., mouse, guinea pig [gp], and rat) will continue to play a vital translational role in modeling vaccine modalities. Of rodent models, only guinea pig CMV (gpCMV) encodes sequence homologues of UL128 and UL130 (Schleiss et al. 2008; Yamada et al. 2009) while the functional importance of UL128C proteins to cell tropism is restricted to primate CMVs (Hansen et al. 2003; Rivailler et al. 2006; Oxford et al. 2008). Data described in Example 1 below has demonstrated the applicability and translatability of HCMV vaccine approaches in a highly relevant primate host.

The Examples below show that through manipulation of a BAC derived MVA, each of the 5 subunit proteins constituting the UL128C have been serially cloned in separate insertion sites of MVA maintained as a BAC plasmid (MVA-BAC). The function of UL128C after vaccination of RhCMV-negative Rhesus macaques (RM) with UL128C-MVA and demonstrating the production of high titer NAb that inhibit virulent RhCMV natural isolates from infecting Epi/EC cells and fibroblasts. Based on these results in RM, it is likely that a HCMV counterpart to the Rhesus UL128C can be assembled in MVA-BAC and used to vaccinate RM to elicit NAb that prevent in vitro HCMV infection of multiple permissive cell types.

In one embodiment described in Example 2, an UL128 complex may be constructed using MVA-BAC molecular technology. Using viral DNA prepared from the 1974-MVA strain currently being used in clinical trials, a self-excisable MVA-BAC will be generated using methods described herein. Subsequently, five human subunits of the UL128C (UL131A, UL130, UL128, gL, and gH) may be serially cloned into MVA-BAC. In some embodiments, equal expression of all five subunits in a single rMVA may be analyzed for stability by serial passage in an FDA-acceptable human vaccine cell substrate, chicken embryo fibroblasts. Mouse immunization further substantiates the functional capacity of HCMV UL128C-MVA vaccine to elicit NAb which inhibit virulent HCMV natural isolate infection of susceptible Hu Epi/EC cells. Using an intraperitoneal (i.p.) route of immunization, Balb/C mice in groups of four animals were vaccinated with MVA strains that include UL128C, UL128CΔ, UL128-UL130-131, gH/gL, gB, and Venus. The cells that were used for the in vitro neutralization were the human ARPE-19 (retinal pigment epithelial cells) that are standard in the field. The construct that gave superior neutralization of the VHL-1, TR, and TB40/E HCMV strains was the UL128C-MVA construct which has the full-length gH as one of the inserts.

In another embodiment described in Example 2, immunization of RhCMV-uninfected RM with 1974-MVA-UL128C and characterization of NAb responses may be evaluated. rMVA generated in this example may be used to intradermally inoculate RM. Two doses of UL128C-MVA separated by 6 weeks will be given to each of 6 RM, followed by an additional 6 weeks prior to harvesting sera and saliva for in vitro studies. Sera and saliva obtained from immunized RM will be used to block infection by HCMV isolates containing the ULb' virulence region, and expressing the UL128C pentamer. Assessment of the function of NAb produced in control and vaccinated RM to interfere with HCMV infection of ARPE-19 (retinal pigment epithelial) cells and primary human fibroblasts will be conducted. HCMV laboratory and virulent strains will be used as an infectious challenge of ARPE-19 cells co-incubated with sera or saliva from immunized RM and controls.

In another embodiment described in Example 3, HCMV proteins, pp65, and gB may be inserted into MVA-BAC and the expression, stability and immunogenicity of this construct may be studied in a similar manner as for UL128C-MVA. pp65-gB-MVA and UL128C may be given to RM every 6 weeks as a mixture or separately. HCMV-specific NAb will be measured using in vitro methods using either ARPE-19 cells or primary fibroblasts. Titers that prevent HCMV infection may be measured with the goal of finding that both Epi/EC and fibroblast routes of HCMV infection are inhibited by vaccine-stimulated NAb. An alternative vaccine in which all UL128C subunits and pp65/gB are inserted in a single MVA-BAC, may be evaluated for equal subunit expression and genetic stability. This vaccine will be given to RM, and in vitro neutralization of HCMV will be conducted in ARPE-19 cells and primary human fibroblasts.

The following examples are intended to illustrate various embodiments of the invention. As such, the specific embodiments discussed are not to be construed as limitations on the scope of the invention. It will be apparent to one skilled in the art that various equivalents, changes, and modifications may be made without departing from the scope of invention, and it is understood that such equivalent embodiments are to be included herein. Further, all references cited in the disclosure are hereby incorporated by reference in their entirety, as if fully set forth herein.

EXAMPLES

The following examples illustrate that all 5-members of the HCMV UL128C can be simultaneously expressed in a BAC-derived version of a clinically relevant MVA vector to stimulate NAb that prevent Epi/EC cell infection. These examples include at least the following observations: (1) BAC technology can be applied to rapidly engineer MVA to efficiently express RhCMV UL128C in a single cell; (2) immunization of RM with MVA-RhCMV-UL128C elicits biologically relevant titers of NAb that neutralize RhCMV epitheliotropic strains; (3) BAC technology is effective for expressing a functional 5-member HCMV UL128C in a single cell; (4) the clinically approved 1974-MVA strain can be cloned into a BAC; and (5) use of RhCMV-negative RM to analyze the development of NAb that block infection of human Epi/EC cells with HCMV, (6) challenge results in RM. (7) HCMV UL128C in MVA elicits NAb in mice that neutralize different HCMV Epi/EC-tropic strains (TB40/E, VHL-1, TR, others) on ARPE cells.

MVA-BAC is superior to past strategies, because its use eliminates serial derivations of progressively modified viruses and plaque purification in eukaryotic cells for 5-10 passages, requiring months or even years to stably express multiple genes. In contrast, the BAC system permits modification of large genomes in an easy-to-apply bacterial system in which months of work can be consolidated into weeks. This approach may be the only manageable strategy to co-express 5 or more genes from a single vector, each under the same or different promoter sequence (mH5). HCMV subunit gB may also be inserted into MVA to induce NAb that interfere with fibroblast entry as was demonstrated recently (Wang et al. 2004; Abel et al. 2010). Whether the final vector contains solely members of the UL128C or combined with pp65 and gB, this approach of genetic manipulation of MVA in the BAC system represents a significant change from traditional approaches and expands the applicability of MVA to be optimal for multi-component complexes required for production of NAb that recognize conformational epitopes exemplified by UL128C. Since it has been shown that RM are capable of generating a functional NAb response to RhCMV pp65 and gB (Abel et al. 2010) and RhUL128C (Wussow et al, 2013), generating NAb in response to HCMV UL128C-+gB-MVA vaccination that will neutralize HCMV isolates in an in vitro analysis system should also be successful.

Example 1: A Vaccine that Induces Broadly Neutralizing Antibodies in CMV-Naive Rhesus Macaques which Inhibit Major Portals of Rhesus CMV Infection Viruses and Cells.

The propagation of MVA in baby hamster kidney (BHK) cells, and the preparation and storage of viral stocks were performed according to previously reported protocols (Wang et al. 2010). Chicken embryo fibroblasts (CEF) for MVA propagation were maintained in virus production serum free medium (VP-SFM; Invitrogen).

MVA expressing the full-length 5-subunit pentamer of RhUL128, RhUL130, RhUL131, RhgL and RhgH (MVA-RhUL128C), MVA expressing the 5-subunit pentamer with an alternative transmembrane (TM) domain deleted version of gH (MVA-RhUL128CΔ), or MVA expressing the RhUL128, RhUL130 and UL131A subunits were generated by the BAC technology as described below. MVA expressing either RhUL128 or RhUL130 alone were generated by the conventional manipulation strategy in eukaryotic cells as described previously (Wang et al. 2007). The construction of MVA-RhgB having a deleted TM domain has been previously described (Yue et al. 2008). The epithelial cell-tropic UCD59 strain of RhCMV, which contains a full-length UL/b' region, including intact RhUL128-UL131A locus (GenBank accession number EU130540: originally annotated as strain 22659) (Oxford et al. 2008), was serially passaged four times on MKE cells for these studies. RhCMV strain 68.1 (ATCC) was propagated on telomerized rhesus fibroblasts (Telo-RF) (Oxford et al. 2011). MKE cells were maintained in Dulbecco's modified Eagle's medium F12 (DMEM:F12; Invitrogen) supplemented with Epithelial Cell Growth Supplement (ScienCell), 1 mM Sodium Pyruvate, 25 mM HEPES, 100 U/ml Penicillin, 100 µg/ml Streptomycin, 2 mM L-glutamine (Invitrogen), and 2% Fetal bovine serum/SuperSerum (Gemini Bio-Products). Telo-RF cells were maintained as described Abel et al. 2011). All cells were grown at 37° C., 5% $CO_2$, and 95% humidity.

Transfer Plasmids.

Transfer plasmids to insert gene expression cassettes for the individual RhCMV genes into MVA-BAC by En Passant mutagenesis were generated as follows. First, synthetic intron-free coding sequences for RhUL128, RhUL130, or RhUL131A (GenScript), as well as PCR-amplified coding sequences for RhgL and RhgH of RhCMV strain UCD59 (Genbank accession numbers EU130540.1, HQ667932.1, and HQ667933.1) were individually inserted via PmlI and AscI restriction sites between the vaccinia virus modified H5 (mH5) promoter and Poly-T (STAT) transcription termination signal of plasmid pZero2-mH5 (Wang et al. 2010). The coding sequence for RhUL130 was synthesized with two C to T nucleotide changes at positions 99 and 102 of the ORF in comparison to the published sequence. For the generation of RhgHΔTM, the first 690 codons of RhgH were amplified via PCR with a reverse primer providing a 3'-terminal coding sequence (GAG CAG AAA CTG ATA TCT GAA GAG GAC CTC TGA; SEQ ID NO:1) for the myc-tag epitope EQK LIS EED L (SEQ ID NO:2).

In contrast to RhUL128, the RhUL130, RhUL131A, RhgL, and RHgH ORFs were inserted with 5'-terminal Kozak sequences (GCC ACC ACC (RhUL130 and RhUL131A; SEQ ID NO:3), GCC GCC GCC (gL; SEQ ID NO:4), or GCC GCC ACC (gH; SEQ ID NO:5)) preceding the ATG start codons. In the next cloning step, the Kanamycin resistance ($Kan^R$) marker aphAI and the homing endonuclease restriction site I-SceI of plasmid pEPkan-S2 (Tischer et al. 2006), were PCR amplified with primers providing 50 bp gene duplications, and inserted into unique restriction sites of the cloned genes. The primer sequences used to amplify the aphAI-I-SceI cassette and the restriction site used to clone the PCR product are given in Table 1 below. In the resulting constructs, the aphAI-I-SceI cassettes within the genes were flanked by 50 bp gene duplications (FIG. 1A). All cloned inserts were confirmed by sequencing. The complete sequences of all transfer plasmids are available upon request.

TABLE 1

Cloning primers.
Primer for cloning of aphAl-I-SceI and gene duplication into RhCMV genes

| Gene[A] | Primer sequences (5' to 3')[B] | Site[C] |
|---|---|---|
| UL128 | GTACAATTGGTTCCTTAAGAAGCTCCTAGAATATGAAAAAATGATACTTATCTAGGGATAACAGGGTAATCGATTT (SEQ ID NO: 6) GCCCAATTGGCCAGTGTTACAACCAATTAACC (SEQ ID NO: 7) | MfeI |
| UL130 | CGGTACCCTCTAGCGTCACGATATAGTTCCGCCTGGCTGTTTAGGCGGCATTAGGGATAACAGGGTAATCGATTT (SEQ ID NO: 8) CGGTACCGCCAGTGTTACAACCAATTAACC (SEQ ID NO: 9) | KpnI |
| UL131 | GTACAATTGTTGGAAAAAATAATTAATGCGTCAGTCTCGTATCATTACGCTACTAGGGATAACAGGGTAATCGATT T (SEQ ID NO: 10) GCCCAATTGGCCAGTGTTACAACCAATTAACC (SEQ ID NO: 11) | MfeI |
| gH | GTACTGCAGAAAGAAGAGCCATATTTGCATTTGAAACAGGACTGTGCTCTCTATAGGGATAACAGGGTAATCGATT T (SEQ ID NO: 12) GCCCTGCAGGCCAGTGTTACAACCAATTAACC (SEQ ID NO: 13) | PstI |
| gL | GTACACGTGTGTAGATAATGTGTGCCGCGCGTACGACCTTCGATATCTCACATTAGGGATAACAGGGTAATCGATT T (SEQ ID NO: 14) GCCCACGTGGCCAGTGTTACAACCAATTAACC (SEQ ID NO: 15) | PmlI |

[A]Target gene cloned into pZero2-mH5.
[B]Primer to amplify aphAl-I-SceI from pEPkanS2. Underlined sequences provided 50 bp gene duplication.
[C]Restriction site used to insert the aphAl-I-SceI cassette into the respective RhCMV gene.

En Passant Mutagenesis.

The cloned RhCMV genes were inserted into the MVA-BAC by two-step Red recombination-based En passant mutagenesis in *E. coli* strain GS1783 according to the published protocol (Tischer et al 2010). Briefly, the gene sequences with the upstream mH5 promoter, the downstream vaccinia virus termination signal, and the introduced aphAI-I-Scel cassette flanked by a 50 bp gene duplication, were amplified via PCR from the pZero2-mH5 transfer plasmids with primers containing 50 bp extensions for homologous recombination, and introduced into the viral genome by a first Red recombination (FIG. 1A). Following that, the $Kan^R$ selection marker was seamlessly excised from the inserted genes by the introduction of a DNA double-strand break at the I-Scel site via expression of the homing enzyme and a subsequent second Red recombination of the 50 bp gene duplications (FIG. 1A). By serial application of these reactions, the five RhCMV genes were successively inserted into four traditional MVA insertion sites as given in FIG. 1B. Primer sequences used to amplify the expression cassettes as well as the gene insertion sites are given in Table 2 below.

TABLE 2

Primer for Red recombination
Primer for Red recombination of RhCMV gene expression cassettes into MVA-BAC

| Gene[A] | Primer sequences (5' to 3')[B] | Site[C] |
|---|---|---|
| UL128 | AAAAAATATATTATTTTTATGTTATTTTGTTAAAAATAATCATCGAATACTATAAAAATTTTTATGGCGCG (SEQ ID NO: 16) GAAGATACCAAAATAGTAAAGATTTTGCTATTCAGTGGACTGGATGATTCGAAAAATTGAAAATAAATACAAAGG (SEQ ID NO: 17) | Del2 |
| UL131 | TTGTACTTTGTAATATAATGATATATATTTTCACTTTATCTCATTTGATTTTTATGAAAAATTGAAAATAAATACAAAGG (SEQ ID NO: 18) ATTCCGAAATCTGTACATCATGCAGTGGTTAAACAAAAACATTTTTATTCTATAAAAATTTTTATGGCGCG (SEQ ID NO: 19) | IGR3 |
| gH | ATATGAATATGATTTCAGATACTATATTTGTTCCTGTAGATAATAACTAATATAAAAATTTTTATGGCGCG (SEQ ID NO: 20) GTGGAAAATTTTTCATCTCTAAAAAAAGATGTGGTCATTAGAGTTTGATTTTTATGAAAAATTGAAAATAAATACAAAGG (SEQ ID NO: 21) | G1L/I8R |

TABLE 2-continued

Primer for Red recombination
Primer for Red recombination of RhCMV gene
expression cassettes into MVA-BAC

| Gene[A] | Primer sequences (5' to 3')[B] | Site[C] |
|---|---|---|
| UL130 | TTGGGGAAATATGAACCTGACATGATTAAGATTGCTCTT TCGGTGGCTGGTATAAAAATTTTTATGGCGCG (SEQ ID NO: 22) | left BAC vector |
|  | TACGCCAAGCTATTTAGGTGACACTATAGAATACTCAAG CTTGGCCGGCCGAAAAATTGAAAATAAATACAAAGG (SEQ ID NO: 23) | end Del3 |
| gL | CAAAGTGGATGAATTCCCAGATCCGGCCTTGCCGGCCTC GAGGGCCGGCCGAAAAATTGAAAATAAATACAAAGG (SEQ ID NO: 24) | right BAC vector |
|  | ACAAAATTATGTATTTTGTTCTATCAACTACCTATAAAA CTTTCCAAATATATAAAAATTTTTATGGCGCG (SEQ ID NO: 25) | end Del3 |

[A]RhCMV gene cloned into pZero-mH5 and containing an internal aphAI-I-SceI cassette flanked by 50 bp gene duplication.
[B]Primer for amplification of the pZero2-cloned gene expression cassette. Underlined sequences mediated recombination.
[C]MVA insertion site of the expression cassette in the MVA-BAC.

Virus Reconstitution.

Virus reconstitution from the MVA-BACs was performed in BHK cells using Fugene HD transfection reagent according to the manufacturer's instructions (Roche) similar to the procedures previously described (Cottingham et al. 2008; Domi & Moss 2002). First, the BAC DNA was purified from GS1783 E. coli cells with the Plasmid Maxi Kit (QIAGEN). Approximately $1 \times 10^5$ BHK cells were seeded in a six-well format and transfected 16-20 h later with 2 μg of purified BAC DNA via the Fugene HD lipid complexes. The cells were infected 4 hours later with Fowlpox virus HP1.441 (Mayr & Malicki 1966) (kindly provided by Bernard Moss, NIAID) at a multiplicity of infection (MOI) of 0.1. After 2 days of incubation, the cells were diluted in a ratio of 1 to 2, and virus reconstitution was monitored by GFP expression and plaque formation. The dilution step may be repeated until more than 90% of the cell monolayer was infected.

Polyclonal Antisera.

Rabbit polyclonal antisera to the RhCMV proteins were generated via the Express Complete Peptide Polyclonal Antibody Package from GenScript against the following peptide sequences: CID SDS YPY EED IDG (SEQ ID NO:26) was used for the RhUL128 antiserum; CTP RSA PAK QVA PKP (SEQ ID NO:27) for the RhUL130 antiserum; CVR PGE IDE CLY RQQ (SEQ ID NO:28) for the RhUL131 antiserum; CFT GET FSP EDD SW (SEQ ID NO:29) for the RhgL antiserum; and HNS TKC NNN GTR RNC (SEQ ID NO:30) for the generation of the RhgH antiserum.

Western Blot (WB).

WB was accomplished similar to published standard protocols (Wang et al. 2004). Briefly, 80-90% confluent BHK cells seeded in 6-well plates were infected with MVA at an MOI 0.1. After 36-40 h, the cells were harvested and centrifuged at 300×g, and total cell lysates were prepared in 200 μl of SDS sample buffer (2% SDS, 100 mM Dithiothreitol (DTT) or 10% β-mercaptoethanol, and 125 mM Tris-HCl/pH 8.8). To detect secreted proteins in the medium, confluent monolayers of CEF cells in 6-well plates were infected at an MOI of 0.1 and grown for 36-40 h in 2 ml of virus production serum-free medium (VP-SFM; GIBCO). The medium was harvested, cleared by centrifugation at 300×g, and concentrated ~20-fold using Amicon® Ultra centrifugal filter devices (10 MWCO, Millipore). The concentrated medium was then prepared for WB by mixing with 5-fold concentrated SDS sample buffer. Lysates of infected CEF cells were prepared as described for BHK cells. Samples were boiled and 10-20 μl portions of the denatured proteins were electrophoretically separated on 10% SDS-polyacrylamide gels, then transferred onto a polyvinylidene fluoride (PVDF) membrane. Rabbit polyclonal antisera were applied in a dilution of 1/5,000. Mouse monoclonal anti-c-myc antibody was used in a dilution of 1/1,000. Secondary anti-rabbit or anti-mouse antibody coupled to horseradish peroxidase (HRP) was employed in a dilution of 1/50,000. Protein bands were finally visualized via chemiluminescent detection (Pierce).

Co-Immunoprecipitation (Co-IP).

BHK cells (80-90% confluent) in a 100 cm² tissue culture dish were infected with MVA-RhUL128CΔ at MOI 5 and incubated for 16-22 h. The cells were harvested in ice-cold PBS and resuspended in 1 ml of ice-cold cell lysis buffer containing 1% (w/v) Triton X-100, 50 mM Tris-HCl (pH 7.4) 300 mM NaCl, 4 mM ethylenediaminetetraacetate (EDTA), 0.02% (w/v) sodium azide, 1 mM phenylmethylsulfonyl fluoride (PMSF), and Complete Mini protease inhibitor cocktail tablets (Roche). After incubation for 30 min on ice, the cell debris was removed by centrifugation at ~10000×g for 10 min at 4° C. The cell lysate was pre-cleared for 30 min at 4° C. with Protein A/G PLUS-Agarose beads and mouse IgG (Santa Cruz Biotechnology). In parallel, Protein A/G PLUS-Agarose beads and 1-2 μg of mouse anti c-myc tag antibody clone 4A6 (Millipore) or mouse IgG irrelevant control antibody were incubated for 2 h in ice-cold PBS, washed 2 times in PBS, and then combined with 500 μl of pre-cleared cell lysate. The mixture was incubated for 2 h or overnight at 4° C. Following that, the agarose beads were washed 3 times in PBS, and boiled in 50 μl of SDS sample buffer. The samples (10-20 μl) were analyzed via WB as described above.

Animals.

Genetically outbred rhesus macaques (Macaca mulatta) from the California National Primate Research Center (CNPRC), repeatedly confirmed to be RhCMV seronegative, were used for these studies. Their age was ~1-2 years at the time of RhCMV inoculation. The animals were co-housed in pairs at least two weeks before immunization, and remained co-housed towards the end of the study 7 weeks after challenge. The Institutional Animal Care and Use Committee of the University of California, Davis (UC Davis), which is fully accredited by the Association for Assessment and Accreditation of Laboratory Animal Care, approved all animal protocols in advance of any procedures.

Immunization and Challenge.

Groups of 4 RM (3 RM for MVA-RhUL130) were immunized by intramuscular injection with ~$5 \times 10^8$ plaque forming units (PFU) of purified MVA 6 weeks apart, as previously described (Yue et al. 2008). Eight weeks after the second immunization, the animals were challenged via subcutaneous injection with $1 \times 10^3$ PFU of RhCMV UCD59 according to previously reported protocols (Yue et al. 2008). Blood, oral swabs and, urine samples for determination of NAb titers and viral loads were prepared as previously described (Yue et al. 2008).

Real-Time PCR.

DNA was extracted from plasma and oral swabs using the QIASymphony automated DNA processor (Qiagen) according to the manufacturer's instructions and published protocols (Huff et al. 2003). The final elution volume was 300 μl. Extracted DNA was stored at −80° C. until real-time PCR analysis was performed. RhCMV UCD59 DNA copies in plasma and oral swabs were detected by a previously described real-time PCR assay (Sequar et al. 2002).

Neutralization Assays.

NAb titers of monkey plasma (EDTA anticoagulant) on fibroblasts were assayed by the use of Telo-RF cells and RhCMV strain 68.1 for infection as described previously (Abel et al. 2011; Abel et al. 2008). NAb on MKE cells were determined as follows. Briefly, 25 PFU of UCD59 were incubated with serial half-log dilutions (1:31 to 1:100) of heat-inactivated (56° C., 30 min) plasma in a final volume of 500 µl of DMEM:F12 with 10% fetal bovine serum. A pooled mixture of plasma from eight RhCMV-uninfected rhesus monkeys was included as a negative control. The virus/plasma mixture was incubated for 2 h at 37° C. and then added in triplicate to monolayers of MKE cells in 24 well plates (500 µl/well), which had been seeded the day before at a density of $6 \times 10^4$ cells/well. Cells in three wells were incubated in growth medium only. After 4 hours of incubation, the virus/plasma mixture was removed, and the cells were washed twice with DMEM:F12, then overlaid with 0.5% agarose and 2 ml of growth medium. After 10-12 days, the plaques were counted. The percent neutralization titer (NT) for each dilution was calculated as follows: NT=(1−(plaque number with immune plasma)/(plaque number with negative control plasma))×100. The titer that gave 50% plaque reduction (NT50 titer) was calculated by determining the linear slope of the graph plotting NT versus plasma dilution.

Data Analysis.

Viral load copy numbers were summarized for each animal as the total area under the curve (AUC) for 16 weeks postchallenge. The AUC between two successive time points (T1 and T2, in weeks) was calculated as the area of the trapezoid formed by the viral loads (VL) at those two time points, according to the following formula: AUC (between T1 and T2)=½($VL_{T1}$+$VL_{T2}$)×(T2−T1). The sum of individual AUC measurements represented the total AUC for each animal.

Statistical Analysis.

One- and two-sided rank sum tests for statistical differences between groups were calculated according to Wilcoxon.

Assembly of RhgH/gL/UL128-UL131A in a Single MVA Vector.

Figure 1B:
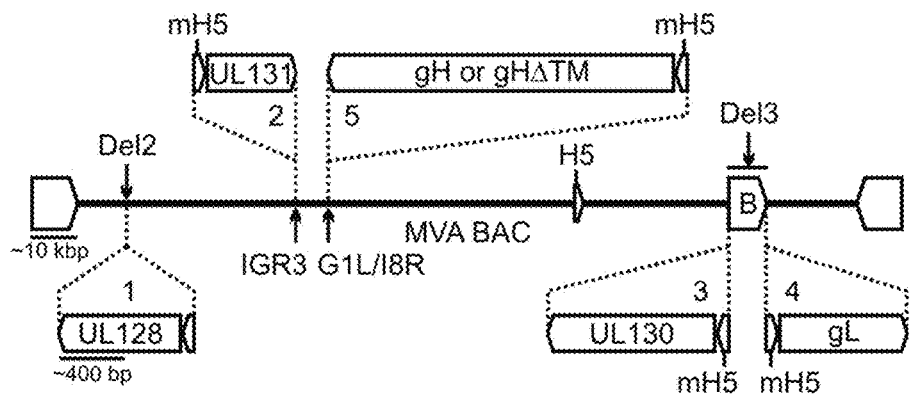

To assemble expression cassettes for all five RhCMV genes within a single MVA genome, an MVA-BAC was used in combination with markerless sequence insertion by En passant mutagenesis (Cottingham et al. 2008; Tischer et al. 2010; Tischer et al. 2006). The MVA-BAC was constructed by insertion of pBeloBAC11 vector sequences together with a GFP expression cassette into the MVA deletion 3 (Del3) site (Cottingham et al. 2008). Using corresponding transfer constructs, the five RhCMV genes including an upstream vaccinia virus mH5 promoter and a downstream transcription termination signal were serially introduced into 4 known MVA insertion sites by En passant mutagenesis in *E. coli* strain GS1783 without bacterial selection markers (FIG. 1A). Expression cassettes for RhUL128, RhUL131A, or RhgH, either as a full-length (FL) or TM-deleted form (RhgHΔTM), were inserted into the Deletion II site (Del2), intergenic region 3 (IGR3) (Manuel et al. 2010), and the insertion site between the essential ORFs G1L and I8R (Wyatt et el. 2009), respectively (FIG. 1B). Further, expression cassettes for RhUL130 and RhgL were introduced into the Del3 site at both ends of the BAC vector (FIG. 1B). The TM-deleted construct was generated with the rationale that expression of a soluble RhUL128C would enhance immunogenicity (Endresz et al. 2001; Wang et al. 200415,61). To facilitate the analysis of RhUL128C, the deleted C-terminal TM of RhgH was replaced by an in-frame coding sequence for a c-myc epitope tag. All other subunits including full-length RhgH were unmodified to prevent disruption of RhUL128C formation (Lilja & Shenk 2008). The individual genes juxtaposed to individual mH5 promoter cassettes were inserted into separate insertion sites in opposite transcription orientations to allow comparable transgene expression while reducing the risk of inter- and intramolecular homologous recombination between the promoter elements (FIG. 1B). The RhgH sequences were inserted into the G1L/I8R site because this site has been described to support stable propagation of large or toxic sequences, such as transmembrane-containing proteins or glycoproteins (Wyatt et el. 2009). The integrity of the cloned MVA genome, as well as markerless insertion of the RhCMV genes, was confirmed by restriction fragment analysis, PCR, and sequencing (data not shown). These results demonstrated that En passant mutagenesis allowed rapid and precise insertion of all five RhUL128C subunits into a single MVA genome cloned as a BAC.

Recovery of MVA Expressing RhgH/gL/UL128-UL131A.

To recover MVA virions co-expressing RhgL/gH/UL128-UL131A, either with or without the TM of gH, termed MVA-RhUL128C and MVA-RhUL128CΔ, the MVA-BAC DNA was transfected into BHK cells to reconstitute virus in the presence of Fowlpox (FPV) helper virus (Cottingham et al. 2008; Domi & Moss 2002). FPV is needed to initiate the transcription machinery from the "naked" MVA DNA, but does not undergo recombination with the MVA genome nor establish a productive infection in BHK cells (Cottingham et al. 2008; Domi & Moss 2002). Recovery of MVA was confirmed after 4-5 days of cell cultivation by observation of cytopathic effect (CPE) and plaque formation of cells expressing the GFP gene originating in the BAC construct (data not shown) (Cottingham et al. 2008). BHK cells infected with the reconstituted viruses were then analyzed via Western Blot (WB). Using rabbit polyclonal antisera that were raised against peptide sequences of individual RhUL128C subunits, the expression of all 5 inserted RhCMV genes was confirmed for both MVA vectors (FIG. 2A). The detected protein sizes were ~55 kD for RhUL128, ~43 kD for RhUL130, ~23 kD for RhUL131, ~32 kD for RhgL, and ~95 kD for RhgH. All protein sizes were larger than the theoretically calculated protein sizes based on amino acid composition, suggesting that all RhCMV UL128C subunits are posttranslationally modified in BHK cells (Lilja & Shenk 2008). The two faster migrating forms of RhgL can likely be explained by unprocessed proteins that require O-glycosylation as a late posttranslational maturation process, as has been shown for HSV (FIG. 2A) (Johnson & Spear 1983). As expected, deletion of the TM resulted in expression of RhgH with a lower molecular weight in comparison to full-length RhgH (FIGS. 2A-B). MVA expressing only one, two or all three of the RhUL128-UL131A subunit proteins were also generated with assistance of BAC technology (FIG. 2B). Co-expression of all RhUL128C protein subunits resulted in an increase of cytoplasmic amounts of UL128-UL131A, which could be explained by either increased stability or expression (FIG. 2B). MVA with single gene insertions were generated within 2-3 weeks, and MVA-RhUL128C and MVA-RhUL128CΔ were generated in 4-5 months. In conclusion, BAC technology was successfully used to rapidly generate MVA vaccines expressing only subsets or all of the five RhUL128C genes.

Stable Co-Expression of RhgH/gL/UL128-UL131A in MVA.

Figure 3:
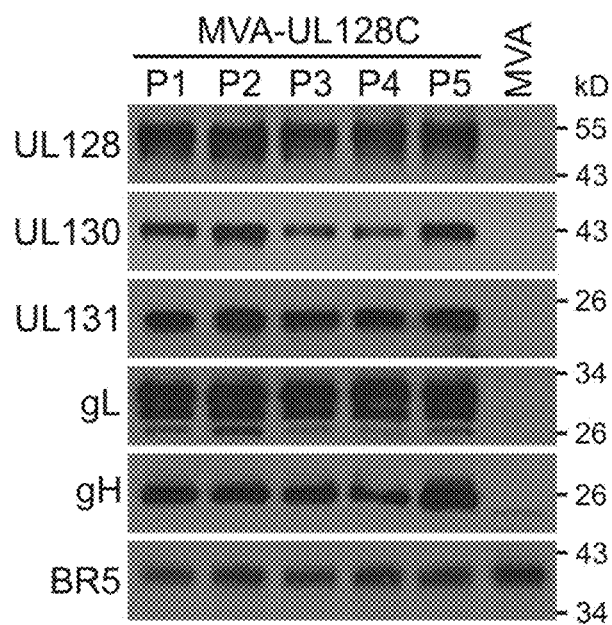
FIG. 3 shows WBs that detect expression of RhUL128, RhUL130, RhUL131A, RhgL, and RhgH during propagation of MVA-RhUL128C on BHK cells (5 virus passages). Total cell lysates of the 5 different virus passages (P1-P5) were analyzed with peptide-specific rabbit polyclonal antisera corresponding to each RhCMV gene. For loading control, lysates were analyzed with monoclonal antibody 19C2 specific for vaccinia virus BR5 protein. MVA-infected and uninfected BHK cells were used as controls.

As a next step the genetic and protein expression stability of MVA-RhUL128C upon virus propagation was investigated. MVA-RhUL128C was passaged 5 times on BHK cells and relative expression levels of all 5 inserted RhCMV genes were determined after each virus passages by WB. Constant amounts of all five RhCMV proteins were confirmed during the 5 virus passages of MVA-RhUL128C (FIG. 3). Stable expression of the inserted RhCMV genes was also confirmed during 5 virus passages of MVA co-expressing RhUL128, RhUL130, and RhUL131A (data not shown). In addition, expression of the solitary RhUL128 gene from a vaccine vector generated by BAC technology or from a vaccine vector derived by the conventional MVA transfection/infection strategy showed comparable expression levels over 10 virus passages (data not shown) (Earl et al. 2001). These results demonstrated that MVA-RhUL128C stably co-expressed all RhCMV genes during serial virus passage and that BAC-derived MVA provided insert stability comparable to conventional derived recombinants. Accordingly, the pentamer and other RhCMV subunit MVA recombinants were judged suitable for large-scale expansion to prepare stocks for immunization studies.

Interaction of RhUL128C Subunits.

Figure 4:
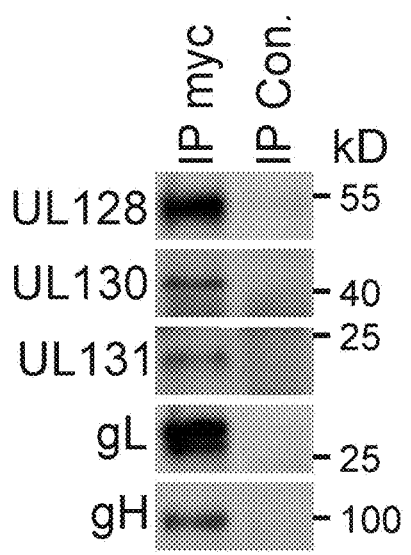
FIG. 4 shows WBs that detect co-immunoprecipitation of RhgHΔTM with RhUL128C subunits after immunoprecipitation of RhgHΔTM expressed from MVA-RhUL128Δ. Lysates of BHK cells infected with MVA-RhUL128CΔ were used for immunoprecipitation with Protein A/G agarose and mouse monoclonal anti-c-myc tag antibody or irrelevant IgG control antibody. The immunoprecipitated samples were then analyzed via WB with rabbit polyclonal antisera specific for each individual subunit. MVA infected BHK cells were analyzed as a control.

To demonstrate formation of the RhUL128C pentamer, protein interactions of RhgH/gL/UL128-UL131A proteins expressed from MVA by co-immunoprecipitation (co-IP) were analyzed. BHK cells infected with MVA-RhUL128CΔ were harvested and processed for IP of RhgHΔTM by detection with anti-c-myc tag monoclonal antibody. The immunoprecipitated proteins were analyzed by WB using polyclonal antisera for the detection of the individual RhUL128C subunits. IP of RhgHΔTM resulted in the co-IP of all other RhUL128C subunits (RhgL, RhUL128, UL130, and UL131A) (FIG. 4). (See Wussow et al. 2013) These results demonstrate that RhgHΔTM interacts with RhgL and RhUL128 when co-expressed from MVA-RhUL128CΔ, which provides evidence of key interactions leading to the formation of a pentameric RhUL128C.

Enhanced Secretion of RhgHΔTM Upon Co-Expression with RhgL and RhUL128-UL131A.

Figure 5:
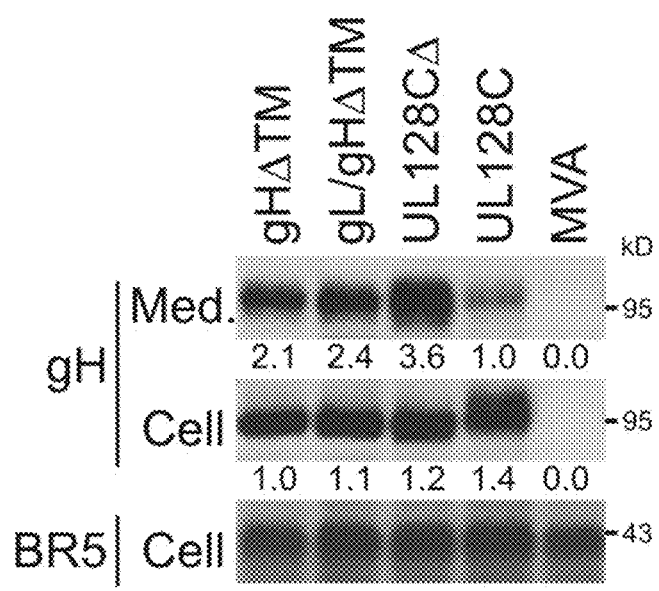
FIG. 5 illustrates secretion of RhgHΔTM upon expression of RhUL128C subunits expressed from MVA. WBs for cellular or secreted RhgHΔTM and RhgH upon single expression, co-expression with RhgL, or RhgL and RhUL128-UL131A. CEF cells were infected at MOI of 0.1 and grown for 36-48 hours in serum-free medium (VP-SFM), and cell lysates and concentrated medium were analyzed with polyclonal antisera. Non-recombinant MVA was analyzed for control. The vaccinia virus BR5 protein was analyzed as a loading control. Relative band intensities are given by numbers below each lane.

Ryckman et al. demonstrated using adenovirus-based expression vectors that secretion of a TM-deleted gH (gHΔTM) is enhanced by co-expression of all UL128C pentamer subunits (Ryckman et al. 2008b). The interaction of subunits forming the RhUL128C pentamer complex of RhCMV was similarly characterized, by comparing the secretion efficacy of RhgHΔTM expressed from MVA alone or in combination with RhgL, or with RhgL and UL128-UL131A (MVA-RhUL128CΔ). The approach was to analyze concentrated serum-free medium and cell lysates of CEF cells infected with MVA constructs by WB using polyclonal anti-gH antiserum. As expected, co-expression of all RhUL128C subunits (MVA-RhUL128CΔ) lead to the highest secretion levels of RhgHΔTM when compared to its expression alone or in combination with gL (FIG. 5). In addition, secreted amounts of RhgHΔTM expressed alone, or in combination with RhgL, or in combination with all other RhUL128C subunits were higher than those of full-length RhgH co-expressed together with all other RhUL128C subunits (MVA-RhUL128C) (FIG. 5), suggesting that the presence of the TM of RhgH tethered the complexes to the cell surface. Interestingly, the size of RhgHΔTM or RhgH detectable in the medium was slightly larger than that observed in cell lysates (relative to the 95 kD size marker), suggesting that secreted forms of RhgH (with or without TM) are differently posttranslational modified compared to cellular counterparts. Coupled with preceding co-IP data, these results further confirm that co-expression of RhgHΔTM with RhgL and RhUL128-UL131A lead to a pentamer complex that promotes enhanced secretion of RhgHΔTM, which is consistent with studies of a soluble form of HCMV gH (Ryckman et al. 2008b).

Induction of Epi/EC-Specific NAb in RM Vaccinated with MVA-RhUL128C.

Figure 6A:
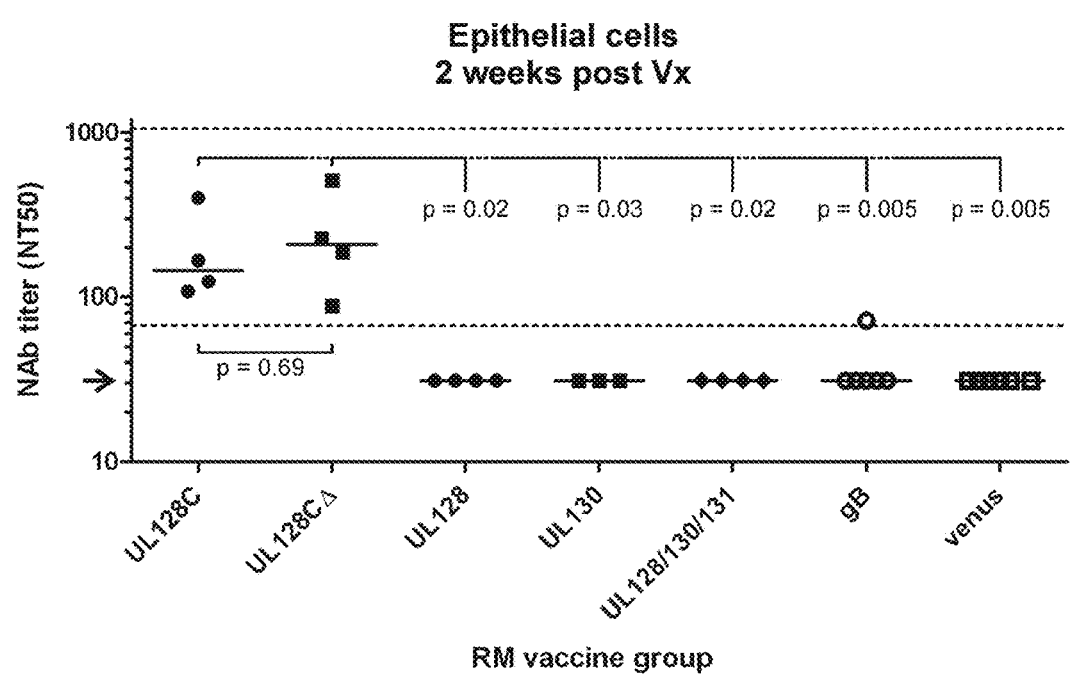
FIGS. 6A-D show in vitro measurements of NAb in vaccinated RM prior to RhCMV challenge.
Figure 6B:
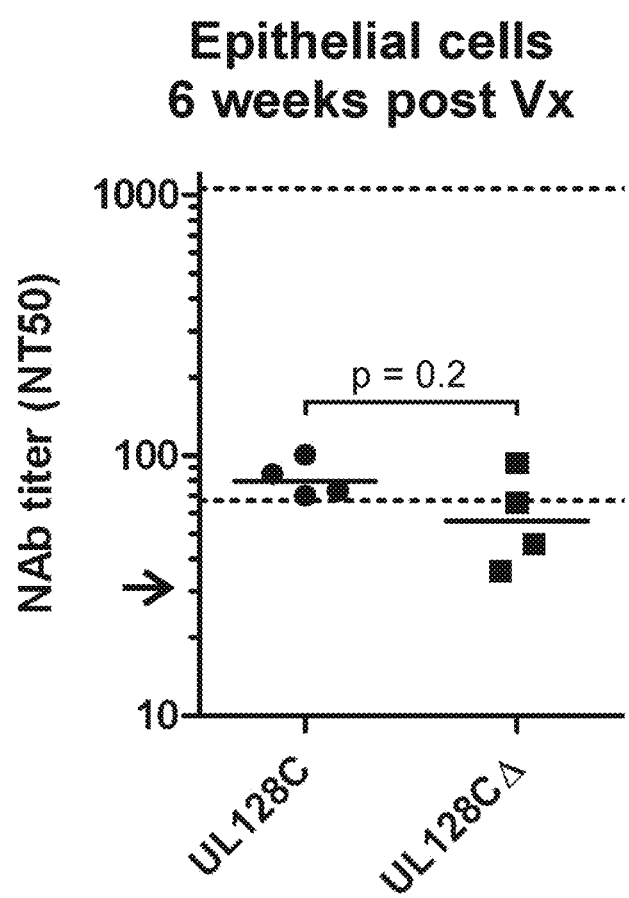

To achieve the central goal of the vaccine program, the capacity of MVA-RhUL128C or MVA-RhUL128CΔ to generate NAb in RM was investigated. Two groups of four RhCMV-negative monkeys were each twice immunized, 6 weeks apart with either MVA-RhUL128C or MVA-RhUL128CΔ (N=4 RM/vaccine). MVA expressing either RhUL128 or RhUL130 (N=3 RM) alone, or MVA co-expressing RhUL128-UL131A were also used for immunization. NAb titers that gave 50% neutralization (NT50) were determined on monkey kidney epithelial (MKE) cells using RhCMV strain UCD59 for infection. Plasma samples of monkeys immunized with RhgB or the bacterial marker gus in a DNA prime/double MVA boost procedure from a previous study were analyzed as additional controls (Abel et al. 2011). NT50 titers of MVA-RhUL128C- or MVA-RhUL128CΔ-vaccinated RM at two weeks post vaccination were comparable to the normative NT50 range of naturally infected RM and ranged from 108 to 402 (median 146) or 88 to 513 (median 209), respectively (FIG. 6A). The normative range of NT50 to UCD59 measured on MKE cells for 3-4 year old corral-housed monkeys is 67-1060 (median 662) (Yue et al, unpublished). In contrast, NT50 titers of RM vaccinated with MVA expressing only RhUL128C subunits or RhgB remained under the detection limit of the assay (FIG. 6A). Only one animal of the MVA-RhgB group had an NT50 titer of 72 (FIG. 6A). Consequently, NAb titers measured on MKE cells of RM either vaccinated with MVA-RhUL128C or MVA-RhUL128CΔ were significantly higher than that of the MVA-venus control group as well as all other vaccine groups (FIG. 6A). At 6 weeks post second immunization, NT50 titers dropped and ranged from 70 to 101 (median 79) for monkeys immunized with MVA-RhUL128C and from 36 to 94 (median 56) for MVA-RhUL128CΔ-vaccinated animals. These NAb titers were still at the lower end of or slightly below the normative NT50 range determined on MKE cells. NAb titers determined for the MVA-RhUL128C and MVA-RhUL128CΔ vaccine groups were not significantly different (p=0.69 at 2 weeks and 0.2 at 6 weeks) (FIG. 6B). These results indicate that co-expression of all 5 RhUL128C subunits, either expressed with a transmembrane anchored or soluble form of gH, are all needed to elicit epithelial cell-specific NAb.

Generation of Fibroblast-Specific NAb in RM Vaccinated with MVA-RhUL128C.

Figure 6C:
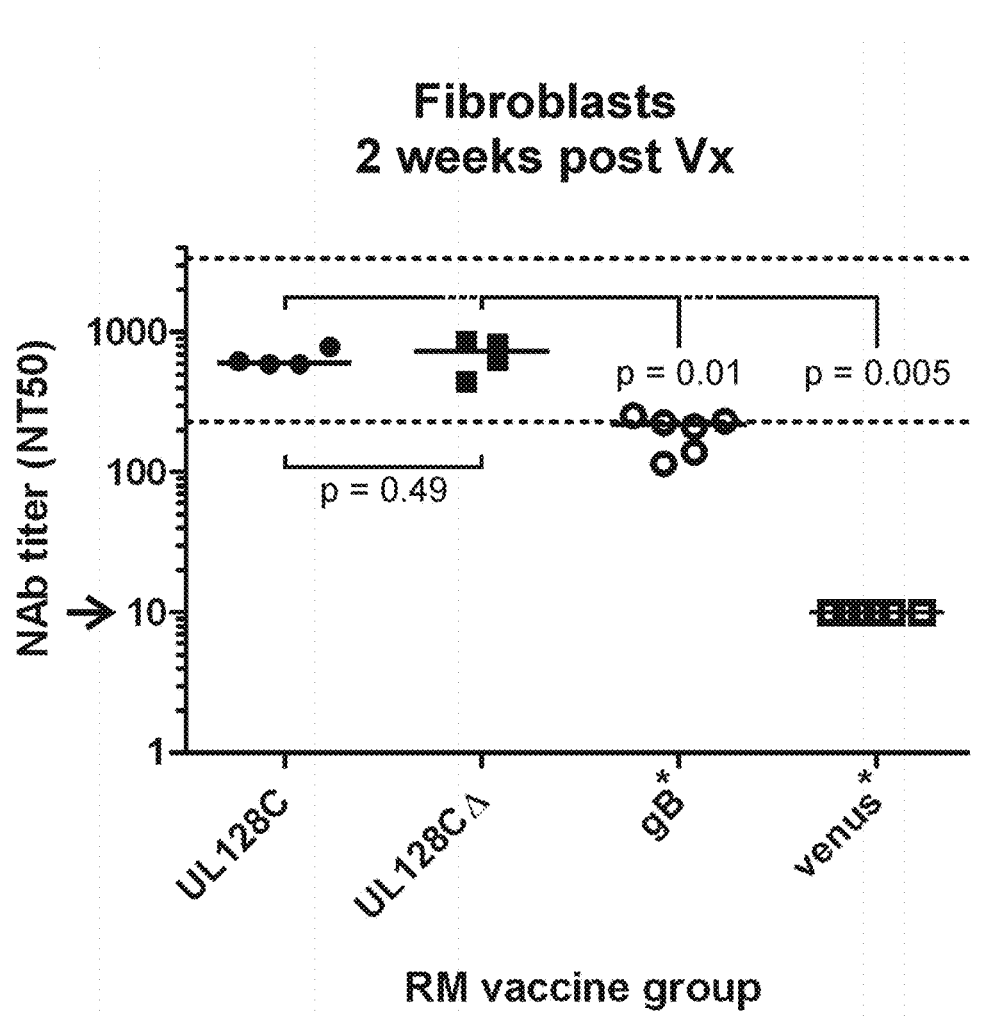
Figure 6D:
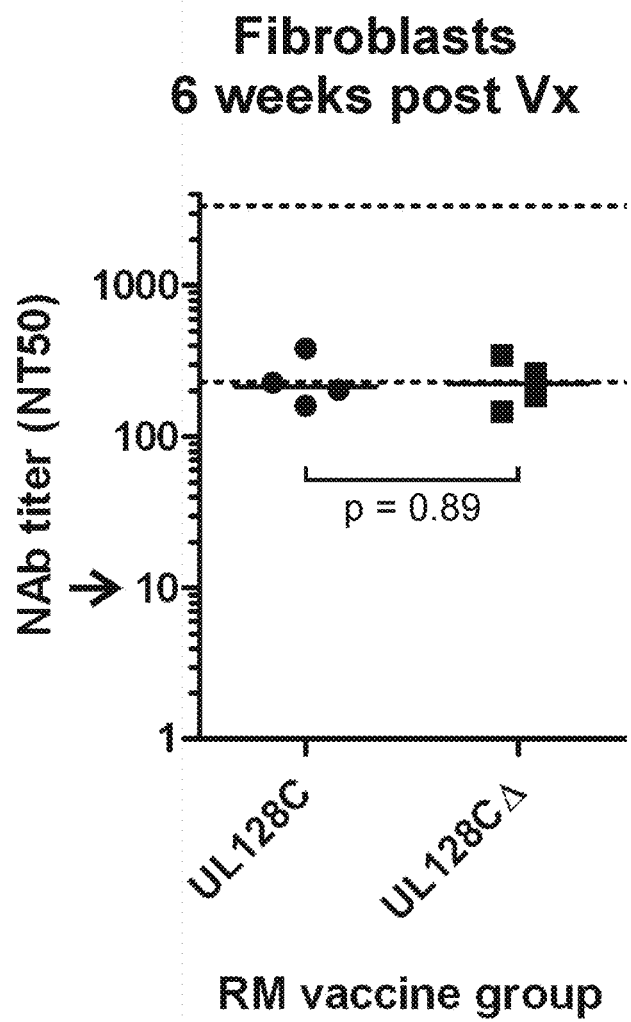

Plasma from RM immunized with MVA-RhUL128C or MVA-RhUL128CΔ vaccines were analyzed for their capacity to inhibit infection of telomerized rhesus fibroblasts (Telo-RF) with RhCMV strain 68-1. Surprisingly, both vaccine constructs induced strong NAb activity preventing RhCMV infection of Telo-RF cells (FIG. 6C). At two weeks post second immunization, plasma of RM immunized with MVA-RhUL128C showed NT50 titers ranging from 590 to 785 (median 608), and sera from animals vaccinated with MVA-RhUL128CΔ had NT50s titer of greater magnitude ranging from 450 to 864 (median 732). These NT50 titer were in the normative NT50 range of naturally infected RM measured on Telo-RF, which ranges from 231 to 3348 for long-term infected animals (Abel et al. 2011). Notably, NAb measured on Telo-RF of MVA-RhUL128C- or MVA-RhUL128CΔ-vaccinated RM at week 2 post vaccination were significantly higher than those of RM vaccinated with MVA-RhgB (3-fold, p=0.01) or control-vaccinated animals (p=0.005) of a previous study (FIG. 6C) Six weeks post second immunization, NAb titers declined, but still ranged from 160 to 383 (median 216) for MVA-RhUL128C vaccinated RM and from 148 to 350 (median 226) for animals of the MVA-RhUL128CΔ vaccine group. NAb at week six were still maintained at the lower end of or slightly below the normative range of NT50 values measured on fibroblasts (FIG. 6D). As with the NAb titer measured on MKE cells, NAb titers determined on Telo-RF from the MVA-RhUL128C and MVA-RhUL128CΔ vaccine groups were not significantly different (p=0.49 and 0.89) (FIGS. 6A-D). In comparison to RhUL128C with full-length gH, deletion of the TM of gH to generate soluble complexes did not improve NAb titers for MKE cells and rhesus fibroblasts. These unexpected results demonstrate that MVA expressing RhCMV gH/gL/UL128-UL131A induce NAb activity that not only inhibits entry into Epi/EC, but impressively also blocks RhCMV infection of fibroblasts.

Reduced Viral Load in MVA-RhUL128C Vaccinated RM Following RhCMV Challenge.

Figure 7:
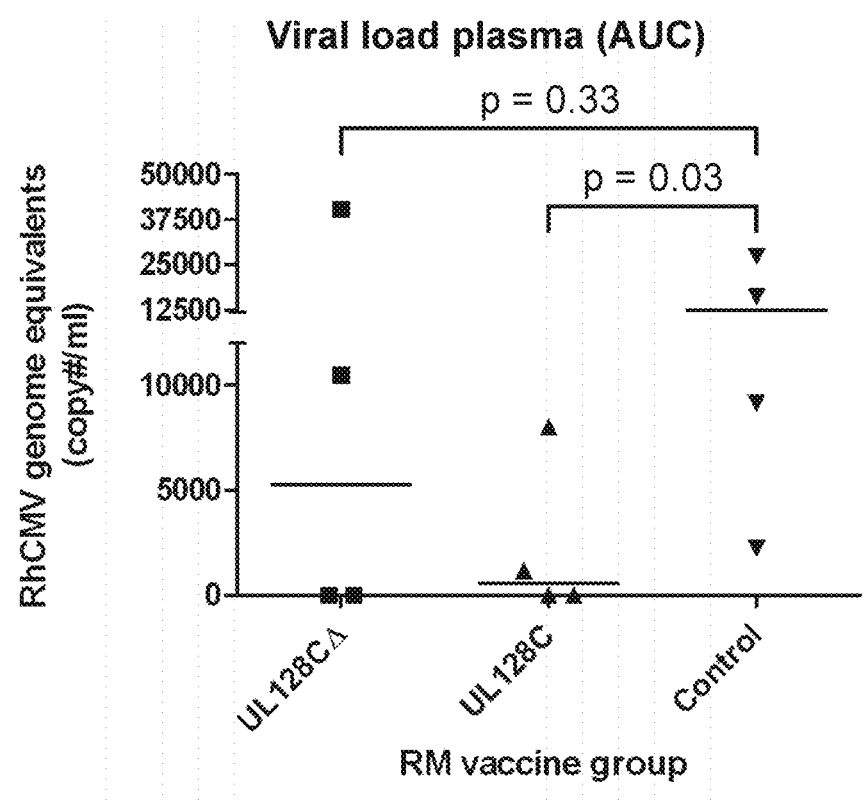
FIG. 7 shows viral load of RhCMV challenge virus in plasma of vaccinated RM. Shown is the area under the curve of detectable genome copy numbers in plasma of RM vaccinated with MVA-RhUL128CΔ, MVA-RhUL128C, and unvaccinated control animals 16 weeks postchallenge. The median AUC of each group is indicated by a solid line. P-values between the vaccine groups and unvaccinated control group were calculated by one-sided rank sum test.

The 2 MVA vaccine groups expressing different forms of RhUL128C that developed NAb activity were next evaluated for protective efficacy against challenge with RhCMV. RM immunized with MVA-RhUL128CΔ or MVA-RhUL128C were subcutaneously inoculated 2 weeks after the booster immunization (at week 6) with the epitheliotropic RhCMV strain UCD59 (Oxford et al. 2011). To serve as a control, unvaccinated animals were also challenged. The number of RhCMV genome copies was then measured by qPCR in plasma and oral swab samples collected every 1 to 2 weeks. FIG. 7 presents the cumulative plasma viral load of UCD59 challenge virus determined by computing the area under the curve (AUC) over a 16-week time interval beginning at the time of challenge. Whereas the plasma viral load of animals immunized with MVA-RhUL128C (median AUC of genome copy numbers=584) was 21-fold lower than control RM (median AUC of genome copy numbers=12, 652), viral load of animals vaccinated with MVA-RhUL128CΔ (median AUC of genome copy numbers=5247) was only 2.4-fold lower than control-unvaccinated animals. Viral load of the majority of RM vaccinated with MVA-RhUL128C was lower than for non-vaccinated RM (p=0.03). Three of four animals vaccinated with MVA-RhUL128C had no or only very few detectable RhCMV copy numbers in plasma (FIG. 7). In contrast, two RM of the MVA-RhUL128CΔ vaccine group showed no viral load, but the other two had high viral load (FIG. 7). Consequently, we cannot infer any improvement in viral load of MVA-RhUL128CΔ-vaccinated RM compared to controls (p=0.33), nor any difference to the MVA-RhUL128C group (p=0.64). However, pooling the two vaccine groups and comparing viral loads to control non-vaccinated animals yields a significance probability of p=0.07, very close to unequivocal statistical significance. These data indicate that vaccination of RhCMV-naïve RM with MVA-RhUL128C reduced plasma viral load in the majority of RM given a virulent challenge virus. The NAb and challenge results are strong indicators that the UL128C pentamer will be a required component of a successful prophylactic vaccine for monkeys and more importantly for humans.

Epi/EC play a pivotal role for HCMV entry, dissemination, persistence, and host-to-host transmission (Sinzger et al. 2008). A vaccine strategy for effective prevention of HCMV infection will likely depend on the ability to induce potent NAb that inhibit virus entry into these cell types (Revello & Gerna 2010; Schleiss 2010). Previous vaccine strategies based on recombinant gB or Towne failed to elicit high titer NAb that inhibit HCMV infection of Epi/EC (Cui et al. 2008). Since the UL128-UL131A proteins that form a pentameric virion complex with gH/gL are required for entry into Epi/EC and serve as targets of potent NAb in HCMV-seropositive individuals, these proteins have been proposed as prime vaccine targets (Gerna et al. 2008; Hahn et al. 2004; Macagno et al. 2010; Wang & Shenk 2005b). The studies described above show that MVA co-expressing all five RhCMV counterparts of HCMV UL128C induce NAb potently blocking virus infection of MKE cells and rhesus fibroblasts. A vaccine expressing these proteins may be an effective candidate to inhibit multiple HCMV entry routes.

By combining BAC technology with markerless sequence insertion by En passant mutagenesis (Cottingham et al. 2008; Tischer et al. 2010), expression cassettes for all 5 RhCMV genes could be rapidly inserted into separate insertion sites of a single MVA genome (FIGS. 1A-B). A commonly used approach based on homologous recombination in eukaryotic cells with subsequent laborious screening procedures would have taken considerably more time to generate these recombinants (Earl et al. 2001). This is the first description of MVA with gene expression cassettes in 5 separate insertion sites, propelling MVA into a new category for multi-antigenic vaccine design. MVA-RhUL128C maintained stable expression of all five RhCMV genes over 5 virus passages (FIG. 3), indicating that this vector construct is a feasible candidate for vaccine development. While each of the individual UL128C subunits could be expressed from separate vectors, simultaneous delivery into a single cell to enable assembly of the functional pentamer will be difficult to achieve in vivo rather than in an in vitro laboratory setting. An optimal approach was identified for pentamer assembly and function that has profound translational consequences as a building block for an HCMV vaccine.

HCMV vaccine evaluation in animal models may be limited because of the strict-species specificity of CMVs, but rodent CMVs and their respective hosts continue to serve as vital animal models to develop HCMV vaccine candidates. Since guinea pig CMV (gpCMV) infects the fetus transplacentally, the gpCMV/guinea pig model is particularly useful to design vaccine strategies for congenital infection (Schleiss 2010). In addition, RhCMV vaccine evaluation in RM represents a nonhuman primate model to develop vaccine strategies analogous to those targeting HCMV (Barry et al. 2006; Yue et al. 2003). From an evolutionary perspective, RM are the closest animals to humans that can be experimentally investigated (Barry et al. 2006). In addition, the genome content and the patterns of viral persistence and host pathogenesis of RhCMV strongly resemble those of HCMV, with the caveat that transplacental transmission of RhCMV has not been verified (Barry et al. 2006; Schleiss 2010). However, in contrast to rodent CMVs, RhCMV encodes a full set of orthologs to HCMV UL128, UL130, and UL131A (Hansen et al. 2003; Lilja & Shenk 2008; Oxford et al. 2008; Rivailler et al. 2006; Schleiss et al. 2008; Yamada et al. 2009).

Some investigators have demonstrated that tagged fusion proteins or derivative peptides of UL128, UL130, or UL131A induce Epi/EC-specific NAb for HCMV in mice or rabbits (Adler et al. 2006; Saccoccio et al. 2011; Wang & Shenk 2005b), suggesting that these UL128C subunits might be sufficient to generate NAb activity in humans. However, generating immunity in small animals against a xeno-antigen may only reflect an immunologic property rather than targeted immunity against host-restricted CMV. This conclusion is based on the fact that the UL130 and UL131A peptides sequences used to generate NAb in rabbits did not bind serum antibodies from HCMV-seropositives (Saccoccio et al. 2011), strongly suggesting that these single linear epitopes would not be immunogenic in humans. In addition, with the exception of only one characterized antibody to UL128, all other characterized human monoclonal NAb that exclusively inhibit HCMV entry into Epi/EC, target conformational epitopes formed by two or more subunits of UL128C (Genini et al. 2011; Macagno et al. 2010). The results described herein are consistent with the aforementioned dependence on co-expression of multiple UL128C subunits to produce functional NAb to induce Epi/EC-specific RhCMV neutralization activity in RM comparable to that induced following naturally infection (FIGS. 6A-D). Addition of RhgH/gL is likely important to tether the remaining RhUL128C subunits to stabilize the formation of conformational epitopes (Ryckman et al. 2008a; Ryckman et al. 2008b). Consequently, the observations in the RhCMV system are analogous to HCMV studies, and strongly suggest the similarity of function of the UL128C of both species and the requirement to form a pentamer to generate effective NAb. The data discussed above support that UL128C pentamers should be a part of a comprehensive prophylactic HCMV vaccine that may be used alone or with one or more additional neutralizing determinants (e.g., RhgB, RhgM/gN, RhgO) and/or one or more major targets of cell-mediated immunity (e.g., Rhpp65 or RhIE1). In addition, a comprehensive prophylactic HCMV vaccine may be administered in combination with additional co-factors, B-cell stimulatory molecules (e.g., CD40L).

RhUL128C vaccinated CMV-naïve RM should elicit NAb that inhibited RhCMV infection of MKE cells, because the pentamer RhUL128C is analogous to the human version of UL128C. However, an additional and unexpected finding was the discovery that NAb could be raised in RhUL128C vaccinated RM that inhibited RhCMV infection of rhesus fibroblasts. These observations suggest that the vaccine construct described herein is capable of stimulating NAb simultaneously against both UL128C and gH/gL complexes. Equally remarkable is that the titers of NAb measured on either MKE or fibroblasts were comparable to those observed in RhCMV-seropositive monkeys (Fouts et al. 2012; Macagno et al. 2010; Urban et al. 1996). Significantly, NAb raised in MVA-RhUL128C vaccinated RM that inhibited RhCMV infection of rhesus fibroblasts had 3-fold greater titers than NAb raised in MVA-RhgB-vaccinated animals as previously described (Abel et al. 2011) (FIG. 6C). It was also confirmed that MVA-RhgB vaccinated RM developed only minimal levels of NAb that inhibited RhCMV infection of MKE cells (FIG. 6A), which strongly supports that MVA-RhUL128C is superior to MVA-RhgB for the induction of NAb inhibiting RhCMV entry into both fibroblasts and Epi/EC. These results amplify the recent analysis of CMV hyperimmune globulin showing that NAb inhibiting entry into Epi/EC or fibroblasts target mainly epitopes of UL128C or gH/gL complexes, and that NAb to gB play only a minor role in the inhibition of HCMV entry into both cell types (Fouts et al. 2012). This data supports HCMV vaccine strategies based on UL128C and/or gH/gL as being more effective than strategies solely relying on gB to generate NAb blocking infection of multiple cell types. However, a combination of the two approaches may even provide higher and broader NAb activities than strategies based only on one of these important neutralizing determinants.

In summary, MVA-BAC technology was examined in combination with markerless sequence insertion by En passant mutagenesis to generate MVA stably co-expressing all five RhCMV counterparts of HCMV UL128C, which is required for virus entry into Epi/EC. It was found that RhCMV-negative RM immunized with these vaccines not only developed strong neutralization activity preventing RhCMV infection of epithelial cells, they also developed strong NAb activity inhibiting infection of fibroblasts. In addition, NAb titer measured on both cell types were comparable to those of naturally infected monkeys. Furthermore, the immunized RM showed reduced viral load in plasma. This study is valuable for at least the following reasons: (1) it was confirmed that all 5 UL128C subunits are sufficient to induce NAb that inhibit RhCMV infection on both Epi/EC and fibroblasts, though single UL128, UL130 or UL131A subunits or combinations are not; (2) NAb titers are equally strong whether the infection substrate is Epi/EC or fibroblasts suggesting that a single vaccine composed of UL128C subunits may bypass the need for a gB subunit vaccine; (3) it was determined that the HCMV vaccines currently being clinically evaluated should incorporate UL128C components to prevent horizontal transmission or they risk being inadequate for the task of preventing CMV infection of both main infection portals, thereby reducing their effectiveness (Bernstein et al. 2009; Griffiths et al. 2011; Kharfan-Dabaja et al. 2012; Pass et at. 2009).

Example 2: Construction and Expression of HCMV UL128C Pentamer Expressed from MVA MVA Expression of Human UL128C Subunits.

MVA expressing the full-length 5-subunit pentamer of human UL128, UL130, UL131, gL and gH (H-UL128C-MVA) were generated by the BAC technology similar as described in Example 1.

Figure 8:
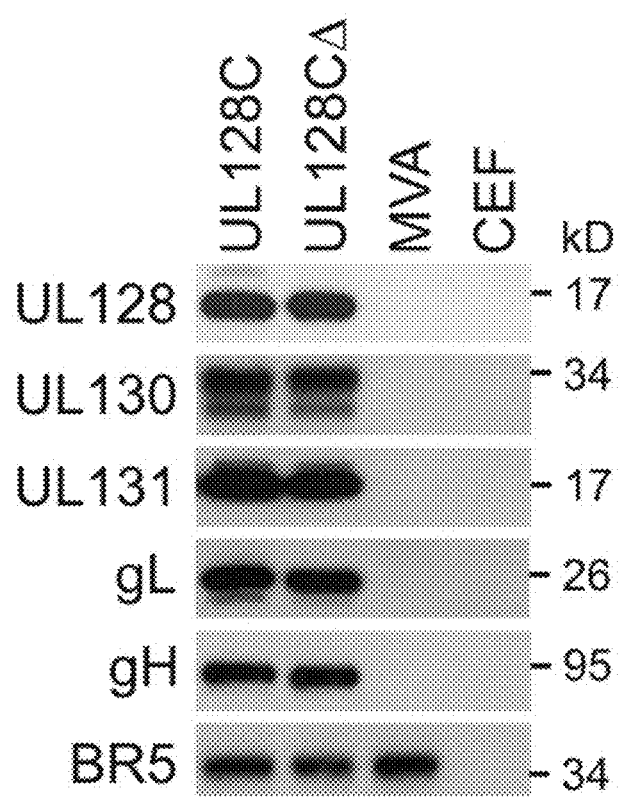
FIG. 8 shows the expression of human UL128C (H-UL128C) subunits from MVA. Shown are results of whole cell extracts in individual lanes of HCMV UL128C subunit antigen expressing MVA. Detection of the proteins on PVDF membranes after SDS-PAGE was accomplished using HCMV-specific mAb (gH, UL128, UL130) and polyclonal sera (UL131A, gL) made in rabbits from H-UL128C-specific peptides. CEF=chicken embryo fibroblasts, BR5=mAb against an MVA endogenous protein used as a loading control.

As shown in FIG. 8, all 5 subunits of the human UL128C (H-UL128C) were successfully expressed, as assessed by either mAb (gH, UL128, UL130) or polyclonal antisera (UL131A, gL) that were used to detect individual subunits. The MW of the individual subunits agrees with published values, providing strong evidence that MVA-based expression is faithful to the structure of these subunits expressed from HCMV. Compositions in which alternative gH structures (e.g., gH with a deleted transmembrane domain, gHΔTM) are co-expressed with the other 4 H-UL128C subunits are also illustrated in FIG. 8 (a composition with the alternative gHΔTM is shown by UL128CΔ, and full length gH (gH-FL) is shown by UL128C). The pentamer complex may be investigated for functional properties assessed in vitro using an approach of inhibition of HCMV infection of an epithelial cell line (Ryckman et al. 2008a). This experiment may be conducted using ARPE-19 and MRC5 cell lines, using two different MVA viruses, H-UL128C-MVA and gB-MVA. This in vitro study should confirm the functional activity of H-UL128C expressed from MVA and should be an effective model for the NAb studies described herein.

Interaction of H-UL128C Subunits.

Figure 9:
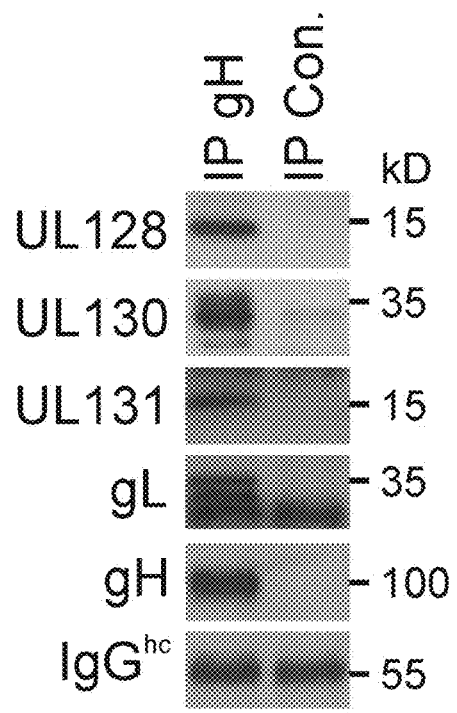
FIG. 9 shows co-immunoprecipitation of HCMV UL128C subunits expressed from MVA. Lysates of BHK cells infected with MVA-UL128C were used for immunoprecipitation of gH with mouse monoclonal antibody anti-HCMV-gH 14-4b or irrelevant control antibody coupled to Protein A/G agarose. Subsequently, the immunoprecipitated proteins were analyzed via WB with mouse monoclonal antibodies to HCMV-gH (clone AP86), UL128, or UL130 and with rabbit polyclonal antisera to gL or UL131 of HCMV (as shown).

To demonstrate formation of the H-UL128C pentamer, protein interactions of human gH, gL, and UL128-UL131A proteins expressed from MVA by co-immunoprecipitation (co-IP) were analyzed (FIG. 9). BHK cells infected with MVA-H-UL128C were harvested and processed for IP of gH with mouse monoclonal antibody anti-gH 14-4b or irrelevant control antibody coupled to Protein A/G agarose. The immunoprecipitated proteins were analyzed by WB using polyclonal antisera for the detection of the individual RhUL128C subunits. The results in FIG. 9 show co-IP of all 5 UL128C subunits after IP of the gH protein. This demonstrates that the individual subunits of H-UL128C interact with each other, forming a functional pentamer when co-expressed from MVA.

Figure 10:
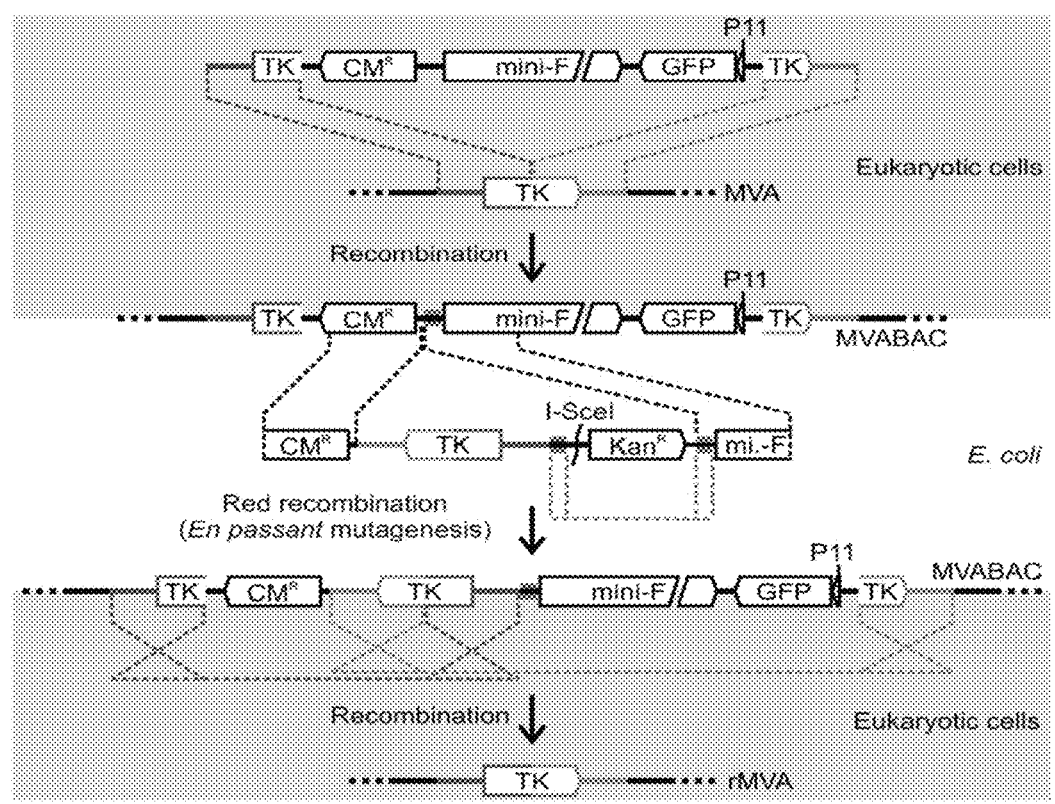
FIG. 10 is a schematic for generating self-excisable MVA-BAC. First, a BAC vector consisting of chloramphenicol resistance marker ($CM^R$), the mini-F replicon, and GFP expression cassette driven by the vaccinia virus P11 promoter is inserted into the MVA Thymidine kinase (TK) locus via recombination in CEF. Thereafter, a recombinant genomic clone is rescued in E. coli and an inverse genomic duplication is inserted via 2-step Red recombination-based En passant mutagenesis into the BAC vector. After transfection of BAC into MVA permissive cells, BAC vector sequences are removed by excision recombination of the genomic duplication.

Example 3: Construction and Evaluation of an MVA-BAC Clinically Acceptable for Human Use Preclinical studies using RhCMV were facilitated by a previously constructed MVA-BAC vector (Cottingham 2008). All vaccines using RhCMV components were assembled using this MVA-BAC. However, because the origins of the MVA are unknown, a different vaccine vector will be used for human use. This MVA BAC will also be constructed in a way that the vector sequences can be deleted after virus reconstitution to avoid the retention of any unwanted functional bacterial sequences, a property that will be likely required for FDA-approval. The vector elements will be inserted into the TK locus to reconstruct insertions sites available for transgene expression. Construction of a MVA-BAC for use with humans was pursued using the 1974-MVA which was provided by Dr. Bernard Moss of the NIAID. The clinical use of this MVA has allowed for the development of multiple vaccines, many of which are now in clinical trial. Therefore, 1974-MVA should be safe to use in humans. A scheme for constructing a self-excisable MVA-BAC based on 1974-MVA (1974-MVA-BAC) is shown in FIG. 10. A restriction map was developed to predict sizes of fragments generated by 6 bp restriction enzymes (RE) that have known profiles in the fully sequenced 1974-MVA genome (data not shown). The RE profile is compatible with the rescue of a full-length genomic clone of MVA. To demonstrate the function of 1974-MVA after BAC cloning, mRFP expression cassettes were inserted into three known MVA insertion sites, and the resulting 1974-MVA-BAC were used to transfect BHK-21 cells. FIG. 11A shows viral plaques displaying red (inserted expression cassette) and green protein expression (GFP expression cassette contained in BAC vector) on CEF monolayers demonstrating functional expression and virus production from the BAC clone after CEF transfection and virus production. Furthermore, the new MVA BAC has been used for the generation of an MVA recombinant expressing CD40L, which will be used in different doses to improve the antibody responses to the UL128C pentamer after mouse immunization.

Three insertion sites of 1974-MVA-BAC were evaluated using 3 different human CMV protein test antigens. All 3 insertion sites express the inserted HCMV gene into protein (FIG. 11B), demonstrating the functional integrity of 1974-MVA-BAC and its ability to be modified with HCMV UL128C subunits and its application to vaccination studies.

MVA-BAC technology was utilized to assemble a functional RhCMV-UL128C that induces NAb inhibiting epithelial cell infection by a natural RhCMV (UCD59) isolate with a functional UL/b' virulence region. A similar MVA-BAC construct of the counterpart human UL128C pentamer complex may also be developed and this construct may be evaluated in RhCMV-negative RM. Although host range restriction of HCMV prevents an RM challenge study, serum may be harvested from vaccinated RM and its capacity to inhibit HCMV infection of virus permissive ARPE-19 cells may be evaluated as a substitute for clinical evaluation. A fully protective vaccine likely needs to inhibit virus infection simultaneously along both endocytic and fibroblast pathways which may be addressed by developing additional MVA constructs, which express gB alone or combined with UL128C. Infection of RM and evaluation of serum NAb inhibition of in vitro infection of fibroblast and ARPE-19 cells may be investigated. Ultimately, investigations by conducting clinical trials may best establish the capacity of these HCMV constructs to prevent or limit infection or viremia. Individuals who would be candidates for immunization include, but are not limited to, women of child-bearing years, adolescents who either shed HCMV or are naïve and would benefit from immunization by interrupting the potential for carrying the infection back to the home and potentially infecting an uninfected mother of child-bearing potential. All such individuals are candidates for immunization with the vectors described in the embodiments of this application.

Assembly of Hu-UL128C in 1974-MVA-BAC, In Vitro Expression and Function Analysis.

The data described above demonstrates that expression of RhCMV UL128C in MVA is valid using a homologous RhCMV-negative RM model in which it is demonstrated that RhCMV-specific NAb are formed after immunization with UL128C-MVA (Example 1). This provided strong evidence that guided development of the UL128C using HCMV genes and expression in MVA which is demonstrated in FIG. 8 (Example 2). In addition, immunoprecipitation of gH followed by WB analysis with monoclonal antibodies for detection of gH, UL128, and UL130 demonstrated assembly of UL128C subunits expressed from MVA (FIG. 9) (Example 2). To achieve the translational relevance that comes with producing a vaccine for human use, the vector should be associated with an MVA that has been approved by the FDA with respect to its safety in clinical evaluation studies. Consequently, 1974-MVA was inserted into a self-excisable BAC vector (FIG. 10) and its functionality was demonstrated in vitro (FIGS. 11A-B). Next, all five subunits of HCMV UL128C may be inserted into 1974-MVA-BAC, and the expression, function, and stability of the subunits are measured. Successful response to the vaccine accompanied by safety analysis should provide powerful support for FDA approval to conduct clinical studies with the same HCMV-MVA vaccine that is investigated in RM.

Construction and Assembly of HCMV 1974-MVA-BAC.

The 1974-MVA-BAC constructed as described in FIG. 10 may be used to insert five antigens of the UL128C as described for the MVA-BAC shown in FIG. 1A. Other deletion sites or intergenic regions may also be used for assembly of the UL128C pentamer or additional transgenes such as gB, pp65, or IE. MVA-BAC generally requires helper virus to initiate replication that is most conveniently addressed by using a cGMP-grade non-replicating fowlpox virus (FPV, obtained from Dr. Bernard Moss, LVD, NIAID) in MVA replication-permissive CEF. The assembled vector is then evaluated in a similar manner as in FIGS. 2A-B to 5, as each subunit is successfully inserted, then expressed from MVA. A WB for expression profiling may be performed for all co-expressed subunits. Subunits UL128, UL130, UL131A, gL, and gH are inserted in that order into the 1974-MVA-BAC. The final insertion of gH may be accomplished using two forms of the glycoprotein; either ΔTM or FL forms. The final stage of the expression analysis of the pentamer construct may be simultaneous expression of all 5 subunits. The goal is roughly equal levels of expression for each subunit, since the working hypothesis suggests an equal proportion of subunits in the final pentamer complex.

Expression levels of all subunits may be normalized against the BR5 antigen, which should have no difference in expression levels regardless of the antigen composition of the MVA vaccine (FIGS. 2A-B). Both pentamer constructs (UL128C-1974-MVA and UL128CΔ-1974-MVA) may be individually tested for in vitro function and in vivo to determine which generates better neutralization of HCMV isolates.

UL128C-1974-MVA-BAC may be produced in CEF, a cell substrate acceptable to FDA. This option may require obtaining an FPV isolate that has a traceable provenance without exposure to the agent for mad cow disease (BSE). Since CEF cells are permissive for FPV, inactivation of virus using combined psoralen and UV light may be implemented as previously described (Lubaki et al. 1994). Alternatively, BHK-21 cells may be used, which are non-permissive for FPV infection, though requiring an FDA registered master cell bank.

Functional Inhibition of HCMV Infection of Permissive ARPE-19 Cells by UL128C Expression.

It may be demonstrated that H-UL128C-MVA prevents HCMV TB40/E endotheliotropic virus (or other virus strains with intact Epi/EC tropism such as TR, VHL-1 etc.) infection of permissive Epi/EC such as ARPE-19 cells or HUVEC. This functional assay is important in establishing success criteria for eliciting NAb, since it may detect proper assembly of a pentamer complex that interferes with HCMV infection of ARPE-19 cells. This study may be conducted with suitable controls such as gB and individual H-UL128C subunits expressed from MVA followed by infection of the Fibro cells (MRC-5) to establish specificity of the inhibition of HCMV TB40/E infection. This establishes conditions in which a monolayer of ARPE-19 or MRC-5 cells is uniformly expressing GFP from H-UL128C-MVA (1974) or control MVA (vary MOI 1-5), prior to investigating inhibition of HCMV infection. Alternatively, an ARPE-19 cell monolayer with uniform GFP expression may be used if co-expression of H-UL128C subunits inhibits the mCherry version of TB40/E infection of ARPE-19 cells with an MOI range between 1-100 pfu/cell. These assays may be conducted in 96 well plates to conserve virus, and for each condition, plaques may be counted in 6 identical wells by red fluorescence and/or HCMV-IE mAb. The following conditions may be used: H-UL128C-MVA, gH/gL-MVA, UL128/130/131-MVA, gB-MVA or GFP-MVA. Significant inhibition of TB40/E infection should be observed solely with UL128C-MVA, and only minimal or no inhibition should be observed using any other MVA in ARPE-19 cells. In contrast, MRC-5 cells may be permissive for TB40/E infection with moderate (~40%) inhibition by gH/gL-MVA as assessed by Hu-IE mAb staining.

Should prevention of TB40/E infection be successful, inhibition of infection using other heterologous natural HCMV isolates (TR or Toledo) may also be examined to assess capacity to prevent infection from a hetero-subtypic strain.

Stability Analysis of UL128C-MVA Assessed by WB and qPCR.

The stability upon passage of UL128C-MVA may be measured by a method that was previously described (Wang et al. 2010). The stability analysis is important because passages are needed for amplification of sufficient virus for either RM or future human use. Ten serial passages of UL128C-MVA may be performed, along with titration of virus stock, expression analysis and genetic analysis of each passage. Stability is based on evaluation of expression levels of each of the five HCMV inserts and the MVA-BR5 antigen at each passage compared to the founder virus designated as P0. Expression levels of each inserted antigen may be compared at each passage and compared to the BR5 antigen for assessment of extent of stability. Because small changes in stability may occur that reflect common observations with MVA (Wyatt et al. 2009), a signal decline of ≤20% from the founder virus at P0 is defined as acceptable. Any genetic variation that is accumulated after passages may also be measured. Using the same procedures for virus passage described above, a qPCR-based analysis of each antigen as well as the endogenous TK antigen that is part of the assembled UL128C-MVA is conducted at each passage. A qPCR signal that is reduced by ≤20% at P10 compared to P0 may be accepted. Details of the qPCR approach for insert quantitation may be found in a previous study. Primers for each of the 5 inserts and MVA-TK gene may be derived from sequence information and validated using the original MVA-BAC DNA containing all five inserts and the MVA-TK gene. This positive control may also be used to develop a standard curve to estimate copy number for each UL128C-MVA passage.

In addition, the entire UL128C-MVA may be sequenced to demonstrate its unaltered state after passage through MVA-BAC intermediate step establishing its suitability as a candidate human vaccine.

Immunologic Function of HCMV UL128C Pentamer in BALB/c Mice.

Animals and immunization regimen. A total of 200 female BALB/c mice (>2 months of age) may be used to confirm expression and humoral immunogenicity of candidate antigens described in this Example and in the Example below. The approach may be to evaluate serum from immunized mice for NAb that will inhibit in vitro HCMV infection of susceptible human cell lines. Mice may be vaccinated with rMVA and prospective blood draws may be used to assess NAb production.

The mouse immunization studies are essential to perform prior to immunization studies in RM for at least two reasons. The first reason is that MVA vectors with candidate antigens need to be confirmed for authentic expression of the coding region prior to studies in macaques. These studies cannot be performed in tissue culture because testing for the formation of NAb requires an intact immune system. It is estimated that 10 rMVA vectors (expressing HCMV genes may be constructed and used for infection of mice (N=10 mice/ rMVA construct). The number of mice per group is based on prior experience to obtain minimally consistent results that may be amenable to statistical evaluation. Each mouse may be immunized by the intraperitoneal, subcutaneous, or intramuscular route with rMVA separated by a minimum of a 3 week interval and periodically bled over the course of 180 days before humane sacrifice. Blood draws for each mouse may be separated by at least 2 weeks. Blood may be collected from the tail vein, and a maximum of 0.25 ml/mouse (<1% body weight) may be collected at once. The goal is to test which rMVA elicits NAb against HCMV infection as described below.

BALB/c mice were immunized using either intraperitoneal or intramuscular routes twice with HCMV UL128C-MVA or UL128CΔ-MVA having either a full-length gH or a transmembrane deleted gH to examine requirements for induction of NAb. An immunization regimen was employed in which 4 mice/group received 10-50 million PFU of UL128C-MVA, UL128CΔ-MVA, UL128-UL130-UL131A-MVA, gL/gH-MVA, gB-MVA, or control venus-MVA (Wang et al. 2004a). Mice received 2 immunizations separated by 3 weeks, and 1 week after the each immunization as well as 20 weeks after the first immunization, serum was obtained for evaluation of NAb content employing the ARPE-19 epithelial cell line or HFF-1 fibroblasts. Approximately 100 PFU of HCMV strains VHL-1, TB40/E, or TR were incubated with serial half-log diluted sera from immunized mice starting with a dilution of 1:100. The mixture was incubated for 1 h at 37° C. and added in triplicate to 80-90% confluent monolayers of ARPE-19 epithelial cells or HFF-1 fibroblasts cells that have been seeded the day before in a 96-well plate formate. Following 22 hours of incubation, the cells were stained for IE1 expression and positive cells were counted under the microscope. Sera from three unimmunized mice were analyzed as a baseline level to determine the neutralization titer (NT) for each dilution as follows: NT=(1−(number of IE1 positive cells with immune plasma)/(number of IE1 positive cells with negative control plasma))×100. The titer that gave 50% neutralization (NT50 titer) was calculated by determining the linear slope of the graph plotting NT versus plasma dilution (Wussow et al. 2013).

In light of the observations made for RM vaccinated with MVA-RhUL128C, serum from mice immunized with either pentamer vaccine may likely contain NAb that inhibit infection of ARPE-19 as well as MRC-5 fibroblast cells with HCMV strains such as TB40/E, TR, or Toledo. whereas strains deficient in the UL/b' region (AD169 and Towne) will not be infectious to ARPE-19 cells. In comparison, gB-MVA infected mice should have lower neutralization activity on both cell types using identical serum preparations. None of the animals vaccinated with subsets of <5 UL128C subunits should develop NAb. In addition, UL128C-MVA expressing either gH-ΔTM or gH-FL may be compared to determine which stimulates a greater amount of NAb. 2× immunized mice may be immunized a third time, 3-6 months later to investigate boosting existing NAb as was accomplished using gB-MVA in a prior study (Wang et al. 2004a). Finally, an Abs IgG subclass may be characterized using a commercial kit to study the evolution of antibody specificity caused by immunization. IgG2A should be predominant when there is successful stimulation of NAb (Wang et al. 2004a).

The time between immunizations and the period after the second immunization may be increased to obtain serum if the neutralization is too low. In addition, a third immunization prior to the proposed 3-6 months may be added and serum may be obtained afterwards for evaluation of neutralization.

Immunization of RM Using UL128C-MVA (1974) and Characterization of NAb.

Animals and Immunization Regimen.

Animals may be derived from RhCMV-uninfected breeding cohorts in outdoor corrals at the California National Primate Research Center (CNPRC). The animals used in the studies described in below are co-housed for each separate component of this project. This is a non-terminal study with minimal invasive procedures, and animals may be returned to the CNPRC colony at the completion of the study. Approximately equal numbers of male and females may be used, although the sex of the animal is not a determining factor for inclusion in, or exclusion from, these studies.

For this example, 30 RhCMV-uninfected macaques may be immunized with recombinant MVA vectors (N=6 per vector), each of which individually expresses 1 of 3 different UL128C subunit MVA vaccines (UL128C, gL/gH, UL128/130/131A), or a control MVA. MVA expressing other combinations of UL128C subunits may also be used. In addition, a fifth group (N=6) may be immunized with up to 200 µg of formalin-inactivated HCMV TB40/E visions (FI-HCMV) adjuvanted in Montanide ISA 720, an oil-in-water adjuvant, delivered by an intramuscular (IM) injection.

The goal of this study is to investigate the potential of each vector to elicit functional NAb. Animals may be immunized three times intramuscularly (IM) at weeks 0, 6, and 26 with 5×10$^8$ PFU/dose of the recombinant MVA in PBS. Prospective venous blood samples and saliva may be obtained from anesthetized (ketamine) animals using standard protocols at the CNPRC. Blood draws may be collected every 1-4 weeks over the course of 28 weeks (relative to the priming immunization at week 0). Blood draws will not exceed CNPRC guidelines (12/month/kg body weight). The blood may be processed for plasma and PBMC by standard protocols, and aliquots may be used to determine complete blood counts (CBC) and blood chemistry (Chem 20). Briefly, saliva is collected with 2 Dacron swabs placed into the buccal pouch. Each swab saturates with 0.2 ml of saliva, and each swab is placed into a tube containing 1.8 ml of PBS, which represents a 1:10 dilution of saliva. This volume leaves sufficient material for multiple assays. Saliva may be analyzed at serial half-log dilutions starting with the collected 1:10 dilution. The saliva may be processed for evaluation of NAb titers similar to serum samples at COH. Vaccinated animals may be co-housed in a corn-crib.

The in vitro expression and small animal immunization studies regarding UL128C validates the function and capacity to elicit NAb by the UL128C pentamer described herein. However, the best experimental model for assessing capacity to elicit NAb relevant for human disease is primate studies. Therefore, studies use RhCMV-negative RM may be performed to preclude the possibility of cross-reactivity to HCMV by pre-existing NAb to RhCMV. The goal is to conduct traditional intramuscular (i.m.) vaccinations as previously conducted (Abel et al. 2010) and to quantitate NAb levels using in vitro neutralization of HCMV (See FIGS. 6A-D and 12A-C). The durability of serum and mucosal (saliva) NAb, optimal number of vaccinations, dose level, impact of gH antigen structure on NAb frequency, affinity, and vaccine safety in RM that is applicable to humans may be investigated. Not only are the functional properties of the vaccine assessed in these studies, but the safety that is relevant to a future FDA application may be investigated using an identical virus manufactured using GMP methods. Additional studies may also pursue optimal vaccine approach for in vivo inhibition of viral challenge using a homologous RhCMV vaccine in RhCMV-negative RM that includes both UL128C and gB/pp65 RhCMV subunits. Combined, the results from RhCMV and human studies will enable translation of an HCMV vaccine that impacts congenital HCMV infection.

Regimens of MVA Immunization of RhCMV-Negative RM.

Four different UL128C subunit MVA vaccines (UL128C or UL128CΔ, gL/gH, UL128/130/131A) or gB-MVA or a control MVA-venus vaccine may be studied for their properties of eliciting functional serum and mucosal NAb in vaccinated RM. Other combinations of UL128C subunits expressed from MVA may also be included as vaccine vectors. Vaccines using RhCMV-negative RM between 1-2 years old may be used. To obtain statistical significance, 6 animals in each vaccine group are included, and 5×10$^8$ PFU/per dose is administered to each animal twice, separated by a 6 week interval [Wussow et al, 2013]. Blood draws and saliva swabs are obtained at 2 weeks, 6 weeks, 3 months and 6 months post second vaccination for each animal (see Vertebrate Animals for collection technique). At 6 months, a third vaccination may be administered and serum and saliva is obtained 2 weeks afterwards for comparison with serum and saliva NAb post-second vaccination.

Alternatively, a $5.0 \times 10^8$ PFU/dose may be administered twice, separated by a 6-week interval which can be altered to either provide less MVA vaccine ($2.0 \times 10^8$ PFU) or a higher amount ($1.0 \times 10^9$ PFU). These amounts proposed work optimally in RM based on previous results.

Evaluation of Serum and Saliva from Immunized RM.

In vitro neutralization may be the principal test for detecting NAb activity. The purpose of the neutralization measurements are identical as in the mouse studies, and the viruses to be investigated and the cell lines to be infected may be identical. A technical change in the dilution of the monkey serum may be instituted based on the expectation of lower titers than in mouse studies (1:31, 1:100, 1:300). These dilutions are consistent with the observed titers using homologous RhCMV vaccines in RM (FIGS. 6A-D). As positive controls, serum from five anonymous HCMV-positive human blood donors is obtained. In addition, a procedure in which HCMV TB40/E formaldehyde-inactivated virions (Abel et al. 2010) are used to immunize RhCMV-negative RM (N=6) is followed, and serum may be drawn and saliva obtained as additional positive controls as recently described (Wang et al. 2011). Saliva may be analyzed at serial half-log dilutions beyond the starting 1:10 dilution comparable to serum dilution. NAb measurement with associated controls should be the most informative regarding the efficacy of HCMV UL128C-MVA to elicit neutralizing responses to HCMV and a comparison of NAb titers with those found in naturally infected humans.

Example 3: Assembly of UL128C-MVA with gB as One Vaccine or a Combination of 2 MVA Vaccines (UL128C+gB) to Develop NAb in RM to Inhibit Both Fibroblast and Endocytic HCMV Infection Pathways Animals and Immunization Regimen.

The studies described above provided evidence that RhUL128C alone can elicit NAb that inhibit infection of both Epi/EC and fibroblasts (FIGS. 6A-D). Additional studies may be performed to combine UL128C with gB/pp65 to enhance or improve the inhibition of both HCMV entry routes. These studies may be conducted in 3 phases. In the first phase, RhCMV-uninfected macaques (N=18 Total) may be immunized with recombinant MVA vectors (N=6 per vector), each of which individually expresses 1 of 3 different MVA vaccines: #1: 5-Ag UL128C (determined from Example 2)+gB/pp65; #2: 5-Ag UL128C alone; #3: gB/pp65 alone. For Group #1, animals may be vaccinated with a vaccine mixture containing both the 5-Ag MVA vector for UL128C and the gB/p65 MVA construct. In addition, a control group (N=6) may be mock-immunized with a control MVA. Animals may be immunized three times intramuscularly (IM) at weeks 0, 6, and 26 with $5 \times 10^8$ PFU/dose of the recombinant MVA in PBS. In the second phase, animals (N=6) may be immunized IM at weeks 0, 6, and 26 either with a 7-Ag MVA complex expressing all 5 members of UL128C and gB/pp65 within one MVA construct. Or, the animals may be immunized with separate immunizations of the 5-Ag MVA and then with the gB/pp65 MVA. For the latter group, animals may be immunized IM at weeks 0, 12, and 26 with 5-Ag MVA, and immunized with gB/pp65 at weeks 6, 18, and 32. Venous blood samples and saliva may be obtained from anesthetized (ketamine) animals using standard protocols. Samples may be collected every 1-4 weeks over the course of 34 weeks (relative to the priming immunization at week 0). Blood draws will not exceed 12/month/kg body weight. The blood may be processed for plasma and PBMC by standard protocols, and aliquots may be used to determine complete blood counts (CBC) and blood chemistry (Chem 20). The saliva may be obtained by running a dacron swab along the gumlines and buccal pouches, and processed as described above. This is a non-terminal study with minimal invasive procedures.

For the third phase, RhCMV-uninfected RM may be inoculated by a subcutaneous (s.c.) route with either the preferred vaccine formulation at multiple sites (N=6) (determined from Phases 1 and 2 above) or with control MVA (N=3). Skin biopsies, 1 cm in diameter may be removed from all 9 animals at 1 site of injection 3, 12, 26, and 52 weeks after the initial inoculation at week 0. This is a non-terminal study with minimal invasive procedures. The challenge route in which RhCMV will be administered to vaccinated RM under study can be either through a mucosal portal such as intra-nasal or intra-rectal or a s.c. route. Challenge may also be carried out through virus transmission by co-habitation with an infected cage mate.

Rationale.

The first HCMV vaccine to show 50% efficacy in a human trial was the gB protein formulated in MF59 adjuvant (gB/MF59) (Pass et al. 2009). Therefore, a strategy seeking >50% efficacy will likely require inhibition of both Epi/EC and fibroblast HCMV entry pathways. Prior RhCMV studies demonstrated that gB was a necessary component to elicit NAb and contributed to the decline in shedding in 50% of the animals which also were vaccinated with pp65 and IE1 expressed from MVA (Abel et al, 2011). However, there are no assurances that combining both the fibroblast and Epi/EC pathway vaccines will result in separate and effective immunity to inhibit both pathways; or that cross-inhibition may occur. There is no precedent for evaluating vaccines to elicit NAb in which these combinations of Ags specific for UL128C and gB are included in the same formulation. Therefore, the best method for administration of MVA vaccines may be determined by conducting preliminary experiments in mice followed by confirmatory experiments in RM. To this end, two MVA viruses may be combined, one expressing UL128C subunits, and the other expressing gB and pp65, to investigate if both antigen complexes can be simultaneously administered to stimulate NAb equal to levels for each antigen complex administered on its own. Alternatively, it may be determined whether administration of UL128C-MVA and gB/pp65-MVA should be administered as separate injections spaced 6 weeks apart due to interference between the two antigen complexes. Assuming, however, that no interference is found in the development of NAb specific for both endocytic and fibroblast pathways by including all seven antigens in a single formulation, an MVA that expresses UL128C and gB may be produced as a convenient, single vaccine approach, to target both endocytic and fibroblast pathways of HCMV entry. The role of HCMV-pp65 in protection requires a challenge model, because pp65 does not stimulate NAb. Further, insertion of a seventh gene (pp65) into UL128C-MVA while maintaining good stability may be investigated to mirror the important components (pp65/gB) of the antigen complement which gave the highest degree of protection against shedding in prior work (Abel et al. 2010). Formulations and regimens may be evaluated in these studies as described in the Examples above. The most translational approach incorporates all antigens into a single MVA vaccine that may be administered twice as was found to be effective in both of the fibroblast (Abel et al. 2010) and endocytic pathway studies described above (see FIGS. 6A-D).

Construction of UL128C+gB/Pp65 MVA and In Vitro Expression.

MVA expressing HCMV UL128C may be constructed as described in the Examples above. Although MVA constructs that express human pp65 and gB exist, both genes may be inserted into 1974-MVA-BAC for consistency. The methods described herein are the same as those described in the Examples above, and the G1L/I8R site is used for gB-ΔTM insertion and IGR3 for pp65 insertion, both genes controlled using an mH5 promoter as shown in FIG. 1B. Unlike gH, there is some difficulty in expressing gB-FL and experience with gB-ΔTM suggests that the construction should be restricted to a single form of gB: gB-ΔTM (Wang et al. 2004a). However, previous MVA recombinants expressing different forms of gB were generated in eukaryotic cells using a transfer plasmid transfection/MVA infection procedure, which failed to generate stable recombinants expressing full-length gB. With the ease of BAC technology, both forms of gB (full-length gB and TM deleted) can be assembled into a viral vector which will allow investigation of their properties of improving antibody generation. Further, an additional site for insertion of pp65 and/or gB into UL128C-1974-MVA-BAC may be selected from sites that have been recently defined for efficient and stable transgene expression (Timm et al. 2006). Alternatively, two antigens may be inserted into each of two known insertion sites (G1L/I8R, Del3) that have been shown to allow the stable propagation of very large and/or toxic sequences. The ease that new constructs are made in MVA-BAC (FIGS. 1A-B) facilitates a rapid screen for alternative insertion sites or the evaluation of double insertions into one site that maintain genes with stability that are equivalent to UL128C-MVA. The simplicity of adding new genes to BAC without manipulating a multi-Ag MVA during vector construction will make the process far simpler than alternatives in which the insert addition would require a eukaryotic transfection-infection step (Wang et al. 2008; Earl et al. 2007). Construction of the pp65/gB-MVA is not likely to be problematic, and a 10-passage stability study may be conducted as was done for UL128C-MVA to ensure proper expression and genetic stability for the manufacturing phase of the program. To amplify the pp65/gB MVA strain for the purposes of having sufficient virus for monkey studies, ≤5 passages are likely needed. Similarly, the UL128C-MVA virus with added pp65 and/or gB inserts may be studied for stability of expression and genetic stability by methods described in the Examples above. Production of sufficient virus for monkey studies requires ≤5 stable passages, but passages may be extended for approximately 10 rounds to gain insight into the long-term stability of the construct. While problems are not likely with these new constructs, insertion of two glycoprotein genes in one MVA needs to be carefully assessed for co-expression and genetic stability to ensure that both pathways are equally inhibited by induction of equivalent levels of NAb as may be assessed as described herein.

Inhibition of HCMV Infection by MVA-Expressed UL128C.

An important objective is to inhibit both the Epi/EC and Fibro HCMV infection pathways using 6 or 7 Ag vaccine formulations. The inhibition of HCMV infection of Epi ARPE-19 cells may be modeled after in vitro infection using MVA constructs developed for both Epi/EC and Fibro pathways. Any H-UL128C interference with HCMV infection can be discerned by HCMV strains which infect both Epi/EC and Fibro lineages (TB40/E and TR), and by evaluating the effectiveness of H-UL128C-MVA to prevent infection. Table 4 shows likely results of in vitro inhibition experiments. The in vitro test should demonstrate successful assembly of the H-UL128C by its interference with HCMV infection of ARPE-19 cells, and suitable controls such as MRC-5 Fibros that should be infected in the presence of expressed H-UL128C, as others have shown[75]. If co-expression of gB/pp65 and H-UL128C in ARPE-19 cells prevents H-UL128C interference of HCMV infection of (TR and TB/40E) strains, H-UL128C and gB/pp65 vaccines may be alternated to inhibit the Epi/EC infection pathway. There are 3 MVA vaccines that may be evaluated: 1) Single MVA H-UL128C-gB-pp65-MVA [7 Ag], 2) two separate MVAs (H-UL128C-MVA [5 Ag]+gB/pp65-MVA [2 Ag]) introduced as a mixture and 3) gH/gL/gO-MVA that is a simple modification of HCMV gH/gL that can be constructed (data not shown). In vitro outcomes are important for both mouse and RM studies.

TABLE 4

| | MVA Vaccine Strains TB40/E and TR | | Interpretation |
|---|---|---|---|
| ARPE-19 Cells | UL128C + gB/pp65 | No Infection | No interference by gB/pp65 |
| ARPE-19 Cells | UL128C + gB/pp65 | Infection | Interference by gB/pp65 |
| ARPE-19 Cells | UL128C | No Infection | Correct assembly of H-UL128C |
| ARPE-19 Cells | UL128C | Infection | Incorrect assembly of H-UL128C |
| Fibro | UL128C + gB/pp65 | Infection | Expected (Vanarsdall et al, 2011) |
| Fibro | UL128C | Infection | Expected (Vanarsdall et al, 2011) |
| Fibro | gB/pp65 | Infection | Expected (Vanarsdall et al, 2011) |
| Fibro | gH/gL/gO | Partial Inhibition | Expected (Vanarsdall et al, 2011) |

Immunization of Combined UL128C+gB/Pp65 Vaccine in BALB/c Mice.

To determine the capacity to elicit NAb for both endocytic and Fibro portals of HCMV infection, five different UL128C and gB/pp65 vaccine combinations may be investigated in accordance with Table 5 below. Specifics of the immunization procedures will be the same as those described above. NAb that inhibit both Fibro and endocytic HCMV infection portals by immunizing mice with 1 or 2 MVAs accounting for all 7 subunits (Table 5) should be elicited. Both ARPE-19 and Fibros should be resistant to both Epi/EC-tropic and Fibro-tropic HCMV infection after in vitro challenge only if both H-UL128C-MVA and gB/pp65-MVA (Groups A or E) or a single vaccine expressing 7 Ag (Group D) successfully generate NAb to inhibit their respective infection portals. Interference caused by Ags injected together in either 1 or 2 MVA would allow infection in ARPE-19 cells (Table 4). In that case, H-UL128C-MVA may be injected independently of gB/pp65-MVA as shown in Table 5, followed by assessment of NAb that inhibit HCMV infection. If separate injections of each vaccine virus still cause interference, RM studies may also be performed to improve predictive power.

TABLE 5

| MVA Type | Group | Mouse | Monkey |
|---|---|---|---|
| UL128C + gB/pp65 | A | Yes, N = 10 | Yes, N = 6 |
| UL128C | B | No | Yes, N = 6 |
| gB/pp65 | C | Yes, N = 10 | Yes, N = 6 |
| UL128C – gB/pp65 | D | Yes, N = 10 | D or E, N = 6 |
| UL128C, then gB/pp65 | E | Yes, N = 10 | E or D, N = 6 |
| GFP-MVA | F | Yes, N = 10 | Yes, N = 6 |
| Total Vaccines | All Groups | N = 50 | N = 30 |

BALB/c mice studies are proposed using a vaccine regimen as described above. The MVA concentration, time between immunizations, and serum withdrawal may be varied based on observed levels of neutralization.

RM studies using vaccine formulations and dose levels may be performed based on the studies described above. Dose levels, time between immunizations, and time to blood draws may be altered to improve in vitro neutralization results. If there is evidence of interference, then MVA mixture studies in RM may be implemented to confirm mouse studies.

Combined Vaccine Formulations Targeting UL128C and gB/Pp65 in RhCMV-Negative RM.

RM studies may commence after the results of mouse studies are obtained and conclusions reached. While the predictive power of mice may be limited, some narrowing of choices will result to limit the breadth of the RM studies. This may be accomplished by evaluation of strategies using 6 animals per group. Genetically outbred, RhCMV-uninfected animals (N=24; ~1-2 years old) will be randomly assigned to one of 4 groups in the 1$^{st}$ stage of evaluation (Table 5; Groups A-C, F). Animals will be repeatedly tested to confirm being RhCMV-negative. Each animal at the CNPRC is molecularly typed by microsatellite mapping for parentage and MHC Class I haplotype (Mamu A*01, B*01, and B*17). Distribution of animals to each vaccinated group will be based on equalizing genetic diversity. Any siblings or half-siblings will be divided among groups. Success with the mixture approach (Table 5, Group A) would prompt investigation of an MVA expressing all 7 antigens comprising UL128C and gB/pp65 as a second stage of evaluation (Table 5, Group D). However, if combining antigens reduces the ability of the vaccine to develop serum or mucosal NAb to inhibit endocytic and fibroblast portals of infection, this result may suggest interference. An alternative second vaccination stage may be UL128C-MVA and gB/pp65-MVA given alternately in a 6-week pattern such that each vaccine is given twice to ensure a lesser likelihood of potential interference, if both doses of the same vaccine are given repetitively rather than alternately (Table 5, Group E). The analysis of the results of the vaccination by conducting in vitro neutralization will take place similarly to mouse and RM studies described in Examples 8 and above. The objective of these studies is discovery of an HCMV vaccine that develops NAb for both endocytic and fibroblast HCMV infection portals that can form the basis of an FDA registration for human investigations.

In this Example, all vaccines contain pp65, a T cell target that was associated with protection against shedding (Abel et al. 2010). Consequently, PBMC may be stored from each blood draw and evaluated using cytokine flow cytometry after in vitro stimulation using overlapping pp65 and control peptide libraries.

In addition, titers of serum and mucosal (saliva) NAb may be examined using an in vitro assay described in Example 8. A vaccine regimen and formulation may be chosen for second stage evaluation based on serum titers of NAb, since those measurements are more widely used. However, mucosal NAb will be measured, and the vaccine that induces both serum and mucosal NAb will be favored over a candidate that only elicits serum NAb.

RhCMV challenge in RhCMV negative animals after RhCMV-MVA vaccination may be performed via different routes. If vaccines contain RhCMV subunits and are injected into RhCMV-negative macaques, then a formal challenge study may be undertaken using virulent epitheliotropic strains of RhCMV. The route of challenge may be either mucosal (intranasal), subcutaneous as in Wussow et al. 2013, or co-habitation of RhCMV-positive macaques with vaccinated RhCMV-negative animals.

REFERENCES

The references, patents and published patent applications listed below, and all references cited in the specification above are hereby incorporated by reference in their entirety, as if fully set forth herein.

Abel, K., J. Martinez, Y. Yue, S. F. Lacey, Z. Wang, L. Strelow, A. Dasgupta, Z. Li, K. A. Schmidt, K. L. Oxford, B. Assaf, J. A. Longmate, D. J. Diamond, and P. A. Barry. 2011. Vaccine-induced control of viral shedding following rhesus cytomegalovirus challenge in rhesus macaques. J. Virol. 85:2878-2890.

Abel, K., L. Strelow, Y. Yue, M. K. Eberhardt, K. A. Schmidt, and P. A. Barry. 2008. A heterologous DNA prime/protein boost immunization strategy for rhesus cytomegalovirus. Vaccine 26:6013-6025.

Adler S P, Nigro G, Pereira L. Recent advances in the prevention and treatment of congenital cytomegalovirus infections. Semin Perinatol. 2007; 31:10-18.

Adler S P, Nigro G. Interrupting intrauterine transmission of cytomegalovirus. Rev Med Virol. 2006; 16:69-71.

Adler, B., L. Scrivano, Z. Ruzcics, B. Rupp, C. Sinzger, and U. Koszinowski. 2006. Role of human cytomegalovirus UL131A in cell type-specific virus entry and release. J. Gen. Virol. 87:2451-2460.

Adler, S. P., S. E. Starr, S. A. Plotkin, S. H. Hempfling, J. Buis, M. L. Manning, and A. M. Best. 1995. Immunity induced by primary human cytomegalovirus infection protects against secondary infection among women of childbearing age. J. Infect. Dis. 171:26-32.

Adler, S. P., S. H. Hempfling, S. E. Starr, S. A. Plotkin, and S. Riddell. 1998. Safety and immunogenicity of the Towne strain cytomegalovirus vaccine. Pediatr. Infect. Dis. J. 17:200-206.

Arvin, A. M., P. Fast, M. Myers, S. Plotkin, and R. Rabinovich. 2004. Vaccine development to prevent cytomegalovirus disease: report from the National Vaccine Advisory Committee. Clin. Infect. Dis. 39:233-239.

Assaf, B. T., K. G. Mansfield, S. V. Westmoreland, A. Kaur, K. L. Oxford, D. J. Diamond, and P. A. Barry. 2012. Patterns of Acute Rhesus Cytomegalovirus (RhCMV) Infection Predict Long-Term RhCMV Infection. J. Virol. 86:6354-6357.

Barry P A, Chang W-L W. Primate Betaherpesviruses. In: Arvin A, Campadielli G, Moore P, Mocarski E S, Roizman B, Whitley R J et al., eds. Human Herpesviruses: biology, Therapy, and immunoprophylaxis. Cambridge: Cambridge University press; 2007:1051-1075.

Barry P A, Strelow L I. 2012 Development of Breeding Populations of Rhesus Macaques That Are Specific Pathogen Free for Rhesus Cytomegalovirus. Comparative Medicine. 58:43-46.

Barry, P. A., K. M. Lockridge, S. Salamat, S. P. Tinling, Y. Yue, S. S. Zhou, S. M. Gospe, Jr., W. J. Britt, and A. F. Tarantal. 2006. Nonhuman primate models of intrauterine cytomegalovirus infection. ILAR. J. 47:49-64.

Bernstein, D. I., E. A. Reap, K. Katen, A. Watson, K. Smith, P. Norberg, R. A. Olmsted, A. Hoeper, J. Morris, S. Negri, M. F. Maughan, and J. D. Chulay. 2009. Randomized, double-blind, Phase 1 trial of an alphavirus replicon vaccine for cytomegalovirus in CMV seronegative adult volunteers. Vaccine 28:484-493.

Boppana S B, Britt W J. Antiviral antibody responses and intrauterine transmission after primary maternal cytomegalovirus infection. J Infect Dis. 1995; 171:1115-1121.

Boppana S B, Rivera L B, Fowler K B, Mach M, Britt W J. Intrauterine transmission of cytomegalovirus to infants of women with preconceptional immunity. N Engl J Med. 2001; 344:1366-1371.

Britt W. Manifestations of human cytomegalovirus infection: proposed mechanisms of acute and chronic disease. Curr Top Microbiol Immunol. 2008; 325:417-470.

Britt W J, Vugler L, Stephens E B. Induction of complement-dependent and -independent neutralizing antibodies by recombinant-derived human cytomegalovirus gp55-116 (gB). J Virol. 1988; 62:3309-3318.

Britt, W. J., L. Vugler, E. J. Butfiloski, and E. B. Stephens. 1990. Cell surface expression of human cytomegalovirus (HCMV) gp55-116 (gB): use of HCMV-recombinant vaccinia virus-infected cells in analysis of the human neutralizing antibody response. J. Virol. 64:1079-1085.

Britt W J. Neutralizing antibodies detect a disulfide-linked glycoprotein complex within the envelope of human cytomegalovirus. Virology. 1984; 135:369-378.

Cha T A, Tom E, Kemble G W et al. Human cytomegalovirus clinical isolates carry at least 19 genes not found in laboratory strains. J Virol. 1996; 70:78-83.

Cottingham M G, Gilbert S C. Rapid generation of markerless recombinant MVA vaccines by en passant recombineering of a self-excising bacterial artificial chromosome. J Virol Methods. 2010; 168:233-236.

Cottingham, M. G., R. F. Andersen, A. J. Spencer, S. Saurya, J. Furze, A. V. Hill, and S. C. Gilbert. 2008. Recombination-mediated genetic engineering of a bacterial artificial chromosome clone of modified vaccinia virus Ankara (MVA). PLoS. One. 3:e1638.

Cui, X., B. P. Meza, S. P. Adler, and M. A. McVoy. 2008. Cytomegalovirus vaccines fail to induce epithelial entry neutralizing antibodies comparable to natural infection. Vaccine 26:5760-5766.

Domi, A. and B. Moss. 2002. Cloning the vaccinia virus genome as a bacterial artificial chromosome in *Escherichia coli* and recovery of infectious virus in mammalian cells. Proc. Natl. Acad. Sci. U.S.A. 99:12415-12420.

Dunn W, Chou C, Li H et al. Functional profiling of a human cytomegalovirus genome. Proc Natl Acad Sci USA. 2003; 100:14223-14228.

Earl P L, Americo J L, Wyatt L S et al. Recombinant modified vaccinia virus Ankara provides durable protection against disease caused by an immunodeficiency virus as well as long-term immunity to an orthopoxvirus in a non-human primate. Virology. 2007; 366:84-97.

Earl, P. L., B. Moss, L. S. Wyatt, and M. W. Carroll. 2001. Generation of recombinant vaccinia viruses. Curr. Protoc. Mol. Biol. Chapter 16: Unit 16.

Endresz, V., K. Burian, K. Berencsi, Z. Gyulai, L. Kari, H. Horton, D. Virok, C. Meric, S. A. Plotkin, and E. Gonczol. 2001. Optimization of DNA immunization against human cytomegalovirus. Vaccine 19:3972-3980.

Fouts, A. E., P. Chan, J. P. Stephan, R. Vandlen, and B. Feierbach. 2012. Antibodies against the gH/gL/UL128/UL130/UL131 complex comprise the majority of the anti-CMV neutralizing antibody response in CMV-HIG. J. Virol. 86:7444-7447.

Genini, E., E. Percivalle, A. Sarasini, M. G. Revello, F. Baldanti, and G. Gerna. 2011. Serum antibody response to the gH/gL/pUL128-131 five-protein complex of human cytomegalovirus (HCMV) in primary and reactivated HCMV infections. J. Clin. Virol. 52:113-118.

Gerna, G., A. Sarasini, M. Patrone, E. Percivalle, L. Fiorina, G. Campanini, A. Gallina, F. Baldanti, and M. G. Revello. 2008. Human cytomegalovirus serum neutralizing antibodies block virus infection of endothelial/epithelial cells, but not fibroblasts, early during primary infection. J. Gen. Virol. 89:853-865.

Gonczol E, Ianacone J, Ho W Z et al. Isolated gA/gB glycoprotein complex of human cytomegalovirus envelope induces humoral and cellular immune-responses in human volunteers. Vaccine. 1990; 8:130-136.

Gonczol E, Plotkin S. Development of a cytomegalovirus vaccine: lessons from recent clinical trials. Expert Opin Biol Ther. 2001; 1:401-412.

Grazia R M, Baldanti F, Percivalle E et al. In vitro selection of human cytomegalovirus variants unable to transfer virus and virus products from infected cells to polymorphonuclear leukocytes and to grow in endothelial cells. J Gen Virol. 2001; 82:1429-1438.

Griffiths, P. D., A. Stanton, E. McCarrell, C. Smith, M. Osman, M. Harber, A. Davenport, G. Jones, D. C. Wheeler, J. O'Beirne, D. Thorburn, D. Patch, C. E. Atkinson, S. Pichon, P. Sweny, M. Lanzman, E. Woodford, E. Rothwell, N. Old, R. Kinyanjui, T. Haque, S. Atabani, S. Luck, S. Prideaux, R. S. Milne, V. C. Emery, and A. K. Burroughs. 2011. Cytomegalovirus glycoprotein-B vaccine with MF59 adjuvant in transplant recipients: a phase 2 randomised placebo-controlled trial. Lancet 377:1256-1263.

Hahn, G., M. G. Revello, M. Patrone, E. Percivalle, G. Campanini, A. Sarasini, M. Wagner, A. Gallina, G. Milanesi, U. Koszinowski, F. Baldanti, and G. Gerna. 2004. Human cytomegalovirus UL131-128 genes are indispensable for virus growth in endothelial cells and virus transfer to leukocytes. J. Virol. 78:10023-10033.

Hanke T, McMichael A J, Dennis M J et al. Biodistribution and persistence of an MVA-vectored candidate HIV vaccine in SIV-infected rhesus macaques and SCID mice. Vaccine. 2005; 23:1507-1514.

Hansen S G, Powers C J, Richards R et al. Evasion of CD8+ T cells is critical for superinfection by cytomegalovirus. Science. 2010; 328:102-106.

Hansen, S. G., L. I. Strelow, D. C. Franchi, D. G. Anders, and S. W. Wong. 2003. Complete sequence and genomic analysis of rhesus cytomegalovirus. J. Virol. 77:6620-6636.

Heineman T C, Schleiss M, Bernstein D I et al. A phase 1 study of 4 live, recombinant human cytomegalovirus Towne/Toledo chimeric vaccines. J Infect Dis. 2006; 193:1350-1360.

Huff, J. L., R. Eberle, J. Capitanio, S. S. Zhou, and P. A. Barry. 2003. Differential detection of B virus and rhesus cytomegalovirus in rhesus macaques. J. Gen. Virol. 84:83-92.

Isaacson, M. K. and T. Compton. 2009. Human cytomegalovirus glycoprotein B is required for virus entry and cell-to-cell spread but not for virion attachment, assembly, or egress. J. Virol. 83:3891-3903.

Jarvis M A, Nelson J A. Molecular basis of persistence and latency. Human Herpesviruses: Biology, Therapy, and Immunoprophylaxis. Cambridge: Cambridge University Press; 2007.

Johnson, D. C. and P. G. Spear. 1983. O-linked oligosaccharides are acquired by herpes simplex virus glycoproteins in the Golgi apparatus. Cell 32:987-997.

Kharfan-Dabaja, M. A., M. Boeckh, M. B. Wilck, A. A. Langston, A. H. Chu, M. K. Wloch, D. F. Guterwill, L. R. Smith, A. P. Rolland, and R. T. Kenney. 2012. A novel therapeutic cytomegalovirus DNA vaccine in allogeneic haemopoietic stem-cell transplantation: a randomised, double-blind, placebo-controlled, phase 2 trial. Lancet Infect. Dis. 12:290-299.

Kinzler E R, Compton T. Characterization of human cytomegalovirus glycoprotein-induced cell-cell fusion. J Virol. 2005; 79:7827-7837.

La Torre R, Nigro G, Mazzocco M, Best A M, Adler S P. Placental enlargement in women with primary maternal cytomegalovirus infection is associated with fetal and neonatal disease. Clin Infect Dis. 2006; 43:994-1000.

Lanzavecchia et al. U.S. Patent Publication No. 2009/0081230

Lilja, A. E. and T. Shenk. 2008. Efficient replication of rhesus cytomegalovirus variants in multiple rhesus and human cell types. Proc. Natl. Acad. Sci. U.S.A. 105:19950-19955.

Lilleri D, Fornara C, Furione M et al. Development of Human Cytomegalovirus-Specific T Cell Immunity during Primary Infection of Pregnant Women and Its Correlation with Virus Transmission to the Fetus. J Infect Dis. 2007; 195:1062-1070.

Liu Y N, Klaus A, Kari B et al. The N-terminal 513 amino acids of the envelope glycoprotein gB of human cytomegalovirus stimulates both B- and T-cell immune responses in humans. J Virol. 1991; 65:1644-1648.

Lubaki M N, Egan M A, Siliciano R F, Weinhold K J, Bollinger R C. A novel method for detection and ex vivo expansion of HIV type 1-specific cytolytic T lymphocytes. AIDS Res Hum Retroviruses. 1994; 10:1427-1431.

Macagno, A., N. L. Bernasconi, F. Vanzetta, E. Dander, A. Sarasini, M. G. Revello, G. Gerna, F. Sallusto, and A. Lanzavecchia. 2010. Isolation of human monoclonal antibodies that potently neutralize human cytomegalovirus infection by targeting different epitopes on the gH/gL/UL128-131A complex. J. Virol. 84:1005-1013.

Maidji E, McDonagh S, Genbacev O, Tabata T, Pereira L. Maternal antibodies enhance or prevent cytomegalovirus infection in the placenta by neonatal Fc receptor-mediated transcytosis. Am J Pathol. 2006; 168:1210-1226.

Maidji E, Percivalle E, Gerna G, Fisher S, Pereira L. Transmission of human cytomegalovirus from infected uterine microvascular endothelial cells to differentiating/invasive placental cytotrophoblasts. Virology. 2002; 304: 53-69.

Mansat A, Mengelle C, Chalet M et al. Cytomegalovirus detection in cryopreserved semen samples collected for therapeutic donor insemination. Hum Reprod. 1997; 12:1663-1666.

Manuel, E. R., Z. Wang, Z. Li, R. C. La, W. Zhou, and D. J. Diamond. 2010. Intergenic region 3 of modified vaccinia ankara is a functional site for insert gene expression and allows for potent antigen-specific immune responses. Virology 403:155-162.

Marshall, G. S., G. G. Stout, M. E. Knights, G. P. Rabalais, R. Ashley, H. Miller, and E. Rossier. 1994. Ontogeny of glycoprotein gB-specific antibody and neutralizing activity during natural cytomegalovirus infection. J. Med. Virol. 43:77-83.

Mayr, A. and K. Malicki. 1966. [Attenuation of virulent fowl pox virus in tissue culture and characteristics of the attenuated virus]. Zentralbl. Veterinarmed. B 13:1-13.

Murphy, E., D. Yu, J. Grimwood, J. Schmutz, M. Dickson, M. A. Jarvis, G. Hahn, J. A. Nelson, R. M. Myers, and T. E. Shenk. 2003. Coding potential of laboratory and clinical strains of human cytomegalovirus. Proc. Natl. Acad. Sci. U.S.A. 100:14976-14981.

Navarro D, Paz P, Tugizov S et al. Glycoprotein B of human cytomegalovirus promotes virion penetration into cells, transmission of infection from cell to cell, and fusion of infected cells. Virology. 1993; 197:143-158.

Nigro G, Torre R L, Pentimalli H et al. Regression of fetal cerebral abnormalities by primary cytomegalovirus infection following hyperimmunoglobulin therapy. Prenat Diagn. 2008; 28:512-517.

Nigro, G., S. P. Adler, T. R. La, and A. M. Best. 2005. Passive immunization during pregnancy for congenital cytomegalovirus infection. N. Engl. J. Med. 353:1350-1362.

Oxford, K. L., L. Strelow, Y. Yue, W. L. Chang, K. A. Schmidt, D. J. Diamond, and P. A. Barry. 2011. Open reading frames carried on UL/b' are implicated in shedding and horizontal transmission of rhesus cytomegalovirus in rhesus monkeys. J. Virol. 85:5105-5114.

Oxford, K. L., M. K. Eberhardt, K. W. Yang, L. Strelow, S. Kelly, S. S. Zhou, and P. A. Barry. 2008. Protein coding content of the UL)b' region of wild-type rhesus cytomegalovirus. Virology 373:181-188.

Oxford, K. L., M. K. Eberhardt, K. W. Yang, L. Strelow, S. Kelly, S. S. Zhou, and P. A. Barry. 2008. Protein coding content of the UL)b' region of wild-type rhesus cytomegalovirus. Virology 373:181-188.

Pass, R. F., A. M. Duliege, S. Boppana, R. Sekulovich, S. Percell, W. Britt, and R. L. Burke. 1999. A subunit cytomegalovirus vaccine based on recombinant envelope glycoprotein B and a new adjuvant. J. Infect. Dis. 180:970-975.

Pass, R. F., C. Zhang, A. Evans, T. Simpson, W. Andrews, M. L. Huang, L. Corey, J. Hill, E. Davis, C. Flanigan, and G. Cloud. 2009. Vaccine prevention of maternal cytomegalovirus infection. N. Engl. J. Med. 360:1191-1199.

Patrone M, Secchi M, Fiorina L et al. Human cytomegalovirus UL130 protein promotes endothelial cell infection through a producer cell modification of the virion. J Virol. 2005; 79:8361-8373.

Plachter B, Sinzger C, Jahn G. Cell types involved in replication and distribution of human cytomegalovirus. Adv Virus Res. 1996; 46:195-261.

Plotkin S A, Furukawa T, Zygraich N, Huygelen C. Candidate cytomegalovirus strain for human vaccination. Infect Immun. 1975; 12:521-527.

Plotkin S A, Starr S E, Friedman H M et al. Effect of Towne live virus vaccine on cytomegalovirus disease after renal transplant. A controlled trial [see comments]. Ann Intern Med. 1991; 114:525-531.

Plotkin S A, Starr S E, Friedman H M, Gonczol E, Weibel R E. Protective effects of Towne cytomegalovirus vaccine against low-passage cytomegalovirus administered as a challenge. J Infect Dis. 1989; 159:860-865.

Rasmussen, L., C. Matkin, R. Spaete, C. Pachl, and T. C. Merigan. 1991. Antibody response to human cytomegalovirus glycoproteins gB and gH after natural infection in humans. J. Infect. Dis. 164:835-842.

Revello, M. G. and G. Gerna. 2010. Human cytomegalovirus tropism for endothelial/epithelial cells: scientific background and clinical implications. Rev. Med. Virol. 20:136-155.

Rivailler, P., A. Kaur, R. P. Johnson, and F. Wang. 2006. Genomic sequence of rhesus cytomegalovirus 180.92: insights into the coding potential of rhesus cytomegalovirus. J. Virol. 80:4179-4182.

Ryckman B J, Jarvis M A, Drummond D D, Nelson J A, Johnson D C. Human cytomegalovirus entry into epithelial and endothelial cells depends on genes UL128 to UL150 and occurs by endocytosis and low-pH fusion. J Virol. 2006; 80:710-722.

Ryckman, B. J., B. L. Rainish, M. C. Chase, J. A. Borton, J. A. Nelson, M. A. Jarvis, and D. C. Johnson. 2008b. Characterization of the human cytomegalovirus gH/gL/UL128-131 complex that mediates entry into epithelial and endothelial cells. J. Virol. 82:60-70.

Ryckman, B. J., M. C. Chase, and D. C. Johnson. 2008a. HCMV gH/gL/UL128-131 interferes with virus entry into epithelial cells: evidence for cell type-specific receptors. Proc. Natl. Acad. Sci. U.S.A. 105:14118-14123.

Ryckman, B. J., M. C. Chase, and D. C. Johnson. 2010. Human cytomegalovirus TR strain glycoprotein O acts as a chaperone promoting gH/gL incorporation into virions but is not present in virions. J. Virol. 84:2597-2609.

Saccoccio F, Sauer A, Cui X et al. 2011. Peptides from cytomegalovirus UL130 and UL131 proteins induce high titer antibodies that block viral entry into mucosal epithelial cells. Vaccine. 29:2705-2711.

Saccoccio, F. M., A. L. Sauer, X. Cui, A. E. Armstrong, e. Habib, D. C. Johnson, B. J. Ryckman, A. J. Klingelhutz, S. P. Adler, and M. A. McVoy. 2011. Peptides from cytomegalovirus UL130 and UL131 proteins induce high titer antibodies that block viral entry into mucosal epithelial cells. Vaccine 29:2705-2711.

Schleiss M R. Role of breast milk in acquisition of cytomegalovirus infection: recent advances. Curr Opin Pediatr. 2006a; 18:48-52.

Schleiss, M. R. 2006b. Nonprimate models of congenital cytomegalovirus (CMV) infection: gaining insight into pathogenesis and prevention of disease in newborns. ILAR. J. 47:65-72.

Schleiss, M. R. 2010. Cytomegalovirus vaccines and methods of production (WO20009049138): the emerging recognition of the importance of virus neutralization at the epithelial/endothelial interface. Expert. Opin. Ther. Pat 20:597-602.

Schleiss, M. R., A. McGregor, K. Y. Choi, S. V. Date, X. Cui, and M. A. McVoy. 2008. Analysis of the nucleotide sequence of the guinea pig cytomegalovirus (GPCMV) genome. Virol. J. 5:139.

Sequar, G., W. J. Britt, F. D. Lakeman, K. M. Lockridge, R. P. Tarara, D. R. Canfield, S. S. Zhou, M. B. Gardner, and P. A. Barry. 2002. Experimental coinfection of rhesus macaques with rhesus cytomegalovirus and simian immunodeficiency virus: pathogenesis. J. Virol. 76:7661-7671.

Shenk et al. U.S. Patent Application Publication No. 2008/0187545.

Shimamura, M., M. Mach, and W. J. Britt. 2006. Human cytomegalovirus infection elicits a glycoprotein M (gM)/gN-specific virus-neutralizing antibody response. J. Virol. 80:4591-4600.

Sinzger, C., M. Digel, and G. Jahn. 2008. Cytomegalovirus cell tropism. Curr. Top. Microbiol. Immunol. 325:63-83.

Stagno S, Reynolds D, Tsiantos A et al. Cervical cytomegalovirus excretion in pregnant and nonpregnant women: suppression in early gestation. J Infect Dis. 1975; 131: 522-527.

Stratton, K. R., J. S. Durch, and R. S. Lawrence. 2001. Vaccines for the 21st Century: A tool for Decisionmaking. Bethesda: National Academy Press.

Timm A, Enzinger C, Felder E, Chaplin P. Genetic stability of recombinant MVA-BN. Vaccine. 2006; 24:4618-4621.

Tischer, B. K., E. J. von, B. Kaufer, and N. Osterrieder. 2006. Two-step red-mediated recombination for versatile high-efficiency markerless DNA manipulation in *Escherichia coli*. Biotechniques 40:191-197.

Tischer, B. K., G. A. Smith, and N. Osterrieder. 2010. En passant mutagenesis: a two step markerless red recombination system. Methods Mol. Biol. 634:421-430.

Urban, M., M. Klein, W. J. Britt, E. Hassfurther, and M. Mach. 1996. Glycoprotein H of human cytomegalovirus is a major antigen for the neutralizing humoral immune response. J. Gen. Virol. 77 (Pt 7):1537-1547.

van Kooten, C. and J. Banchereau. 2000. CD40-CD40 ligand. J. Leukoc. Biol. 67:2-17.

Vanarsdall, A. L. and D. C. Johnson. 2012. Human cytomegalovirus entry into cells. Curr. Opin. Virol. 2:37-42.

Vanarsdall, A. L., B. J. Ryckman, M. C. Chase, and D. C. Johnson. 2008. Human cytomegalovirus glycoproteins gB and gH/gL mediate epithelial cell-cell fusion when expressed either in cis or in trans. J. Virol. 82:11837-11850.

Wang D, Li F, Freed D C et al. Quantitative analysis of neutralizing antibody response to human cytomegalovirus in natural infection. Vaccine. 2011. 29:9075-9080.

Wang Z, La Rosa C, Lacey S F et al. Attenuated poxvirus expressing three immunodominant CMV antigens as a vaccine strategy for CMV infection. J Clin Virol. 2006; 35:324-331.

Wang Z, La Rosa C, Mekhoubad S et al. Attenuated Poxviruses Generate Clinically Relevant Frequencies of CMV-Specific T cells. Blood. 2004; 104:847-856.

Wang Z, Zhou W, Srivastava T et al. A fusion protein of HCMV IE1 exon4 and IE2 exon5 stimulates potent cellular immunity in an MVA vaccine vector. Virology. 2008; 377:379-390.

Wang, D. and T. Shenk. 2005a. Human cytomegalovirus UL131 open reading frame is required for epithelial cell tropism. J. Virol. 79:10330-10338.

Wang, D. and T. Shenk. 2005b. Human cytomegalovirus virion protein complex required for epithelial and endothelial cell tropism. Proc. Natl. Acad. Sci. U.S.A. 102:18153-18158.

Wang, Z., J. Martinez, W. Zhou, R. C. La, T. Srivastava, A. Dasgupta, R. Rawal, Z. Li, W. J. Britt, and D. Diamond. 2010. Modified H5 promoter improves stability of insert genes while maintaining immunogenicity during extended passage of genetically engineered MVA vaccines. Vaccine 28:1547-1557.

Wang, Z., R. C. La, R. Maas, H. Ly, J. Brewer, S. Mekhoubad, P. Daftarian, J. Longmate, W. J. Britt, and D. J. Diamond. 2004. Recombinant modified vaccinia virus Ankara expressing a soluble form of glycoprotein B causes durable immunity and neutralizing antibodies against multiple strains of human cytomegalovirus. J. Virol. 78:3965-3976.

Wang, Z., R. C. La, Z. Li, H. Ly, A. Krishnan, J. Martinez, W. J. Britt, and D. J. Diamond. 2007. Vaccine properties of a novel marker gene-free recombinant modified vaccinia Ankara expressing immunodominant CMV antigens pp65 and IE1. Vaccine 25:1132-1141.

Wilck M B, Chu A, Wloch M et al. Interim Analysis of a Phase 2 Trial of TransVax™, a Therapeutic DNA Vaccine for Control of Cytomegalovirus in Transplant Recipients [abstract]. ICAAC. 2010.

Wille, P. T., A. J. Knoche, J. A. Nelson, M. A. Jarvis, and D. C. Johnson. 2010. A human cytomegalovirus gO-null mutant fails to incorporate gH/gL into the virion envelope and is unable to enter fibroblasts and epithelial and endothelial cells. J. Virol. 84:2585-2596.

Wloch M K, Smith L R, Boutsaboualoy S et al. Safety and immunogenicity of a bivalent cytomegalovirus DNA vaccine in healthy adult subjects. J Infect Dis. 2008; 197: 1634-1642.

Wussow F, Yue Y, Martinez J, Deere J D, Longmate J, Herrmann A, Barry P A, Diamond D J. 2013. A vaccine based on the rhesus cytomegalovirus UL128 complex induces broadly neutralizing antibodies in rhesus macaques. J Virol. 2013 February; 87(3): 1322-32.

Wyatt, L. S., P. L. Earl, W. Xiao, J. L. Americo, C. A. Cotter, J. Vogt, and B. Moss. 2009. Elucidating and minimizing the loss by recombinant vaccinia virus of human immunodeficiency virus gene expression resulting from spontaneous mutations and positive selection. J. Virol. 83:7176-7184.

Yamada, S., N. Nozawa, H. Katano, Y. Fukui, M. Tsuda, Y. Tsutsui, I. Kurane, and N. Inoue. 2009. Characterization of the guinea pig cytomegalovirus genome locus that encodes homologs of human cytomegalovirus major immediate-early genes, UL128, and UL130. Virology 391:99-106.

Yu D, Silva M C, Shenk T. Functional map of human cytomegalovirus AD169 defined by global mutational analysis. Proc Natl Acad Sci USA. 2003; 100:12396-12401.

Yue, Y. and P. A. Barry. 2008. Rhesus cytomegalovirus a nonhuman primate model for the study of human cytomegalovirus. Adv. Virus Res. 72:207-226.

Yue, Y., S. S. Zhou, and P. A. Barry. 2003. Antibody responses to rhesus cytomegalovirus glycoprotein B in naturally infected rhesus macaques. J. Gen. Virol. 84:3371-3379.

Yue, Y., Z. Wang, K. Abel, J. Li, L. Strelow, A. Mandarino, M. K. Eberhardt, K. A. Schmidt, D. J. Diamond, and P. A. Barry. 2008. Evaluation of recombinant modified vaccinia Ankara virus-based rhesus cytomegalovirus vaccines in rhesus macaques. Med. Microbiol. Immunol. 197:117-123.

Zhang, C. and R. F. Pass. 2004. Detection of cytomegalovirus infection during clinical trials of glycoprotein B vaccine. Vaccine 23:507-510.

Zhang, C., H. Buchanan, W. Andrews, A. Evans, and R. F. Pass. 2006. Detection of cytomegalovirus infection during a vaccine clinical trial in healthy young women: seroconversion and viral shedding. J. Clin. Virol. 35:338-342.

---

What is claimed is:

1. An expression system comprising a bacterial artificial chromosome (BAC) construct, the BAC construct comprising a viral vector inserted with DNA sequences that encode cytomegalovirus (CMV) proteins or antigenic fragments thereof that form a UL128 complex, wherein the viral vector is derived from a poxvirus.

2. The expression system of claim 1, wherein the viral vector is derived from an Avipoxvirus, an Orthopoxvirus, or a Parapoxvirus.

3. The expression system of claim 2, wherein the viral vector is a modified vaccinia Ankara (MVA) vector.

4. The expression system of claim 1, wherein the UL128 complex comprises a set of five CMV proteins or antigenic fragments thereof.

5. The expression system of claim 3, wherein the set of five CMV proteins or antigenic fragments thereof are UL128, UL130, UL131A, gL, and gH.

6. The expression system of claim 1, wherein the viral vector is further inserted with one or more additional DNA sequences that encode one or more additional CMV proteins or antigenic fragments thereof selected from pp65, gB or both.

7. A vaccine composition for inhibiting cytomegalovirus (CMV) infection comprising a viral vector capable of expressing CMV proteins or antigenic fragments thereof that form a UL128 complex; and a pharmaceutically acceptable carrier, adjuvant, additive or combination thereof, wherein the viral vector is derived from a poxvirus.

8. The vaccine composition of claim 7, wherein the viral vector comprises a set of DNA sequences that encode the UL128 complex.

9. The vaccine composition of claim 7, wherein the viral vector is derived from an Avipoxvirus, an Orthopoxvirus, or a Parapoxvirus.

10. The vaccine composition of claim 9, wherein the viral vector is a modified vaccinia Ankara (MVA) vector.

11. The vaccine composition of claim 7, wherein the UL128 complex comprises a set of CMV proteins or antigenic fragments thereof.

12. The vaccine composition of claim 11, wherein the set of five CMV proteins or antigenic fragments thereof comprises UL128, UL130, UL131A, gL, and gH.

13. The vaccine composition of claim 7, wherein the viral vector is capable of expressing one or more additional CMV proteins or antigenic fragments thereof selected from pp65, gB or both.

14. A method of inhibiting cytomegalovirus (CMV) entry into a cell comprising contacting the cell with an effective amount of a viral vector, the viral vector comprising a set of DNA sequences that encode CMV proteins or antigenic fragments thereof that form a UL128 complex, wherein the viral vector is derived from a poxvirus.

15. The method of claim 14, wherein the viral vector comprises a poxvirus vector derived from a bacterial artificial chromosome (BAC).

16. The method of claim 14, wherein the viral vector comprises an MVA vector derived from a bacterial artificial chromosome (BAC).

17. The method of claim 14, wherein the UL128 complex comprises a set of five CMV proteins or antigenic fragments thereof.

18. The method of claim 14, wherein the set of five CMV proteins or antigenic fragments thereof are UL128, UL130, UL131A, gL, and gH.

19. The method of claim 14, further comprising one or more DNA sequences that encode additional CMV proteins or antigenic fragments thereof selected from pp65, gB, or both, or from gM/gN and gO.

20. The method of claim 14, wherein the cell is an epithelial cell, an endothelial cell or a fibroblast.

\* \* \* \* \*

SEQUENCE LISTING

<160> NUMBER OF SEQ ID NOS: 30

<210> SEQ ID NO 1
<211> LENGTH: 33
<212> TYPE: DNA
<213> ORGANISM: Artificial Sequence
<220> FEATURE:
<223> OTHER INFORMATION: transfer plasmid

<400> SEQUENCE: 1
gagcagaaac tgatatctga agaggacctc tga        33

<210> SEQ ID NO 2
<211> LENGTH: 10
<212> TYPE: PRT
<213> ORGANISM: Artificial Sequence
<220> FEATURE:
<223> OTHER INFORMATION: myc-tag epitope transfer plasmid

<400> SEQUENCE: 2

Glu Gln Lys Leu Ile Ser Glu Glu Asp Leu
1               5                   10

<210> SEQ ID NO 3
<211> LENGTH: 9
<212> TYPE: DNA
<213> ORGANISM: Artificial Sequence
<220> FEATURE:
<223> OTHER INFORMATION: 5'-terminal Kozak transfer plasmid

<400> SEQUENCE: 3 gccaccacc        9

```
<210> SEQ ID NO 4
<211> LENGTH: 9
<212> TYPE: DNA
<213> ORGANISM: Artificial Sequence
<220> FEATURE:
<223> OTHER INFORMATION: 5'-terminal Kozak transfer plasmid

<400> SEQUENCE: 4 gccgccgcc                                                                   9

<210> SEQ ID NO 5
<211> LENGTH: 9
<212> TYPE: DNA
<213> ORGANISM: Artificial Sequence
<220> FEATURE:
<223> OTHER INFORMATION: 5'-terminal Kozak transfer plasmid

<400> SEQUENCE: 5 gccgccacc                                                                   9

<210> SEQ ID NO 6
<211> LENGTH: 77
<212> TYPE: DNA
<213> ORGANISM: Artificial Sequence
<220> FEATURE:
<223> OTHER INFORMATION: UL128 cloning primer

<400> SEQUENCE: 6
gtacaattgg ttccttaaga agctcctaga atatggaaaa aatgatactt atctagggat          60
aacagggtaa tcgattt                                                         77

<210> SEQ ID NO 7
<211> LENGTH: 32
<212> TYPE: DNA
<213> ORGANISM: Artificial Sequence
<220> FEATURE:
<223> OTHER INFORMATION: UL128 cloning primer

<400> SEQUENCE: 7
gcccaattgg ccagtgttac aaccaattaa cc                                        32

<210> SEQ ID NO 8
<211> LENGTH: 75
<212> TYPE: DNA
<213> ORGANISM: Artificial Sequence
<220> FEATURE:
<223> OTHER INFORMATION: UL130 cloning primer

<400> SEQUENCE: 8
cggtaccctc tagcgtcacg atatagttcc gcctggctgt ttaggcggca ttagggataa          60
cagggtaatc gattt                                                           75

<210> SEQ ID NO 9
<211> LENGTH: 30
<212> TYPE: DNA
<213> ORGANISM: Artificial Sequence
<220> FEATURE:
<223> OTHER INFORMATION: UL130 cloning primer

<400> SEQUENCE: 9
cggtaccgcc agtgttacaa ccaattaacc                                           30
```

```
<210> SEQ ID NO 10
<211> LENGTH: 77
<212> TYPE: DNA
<213> ORGANISM: Artificial Sequence
<220> FEATURE:
<223> OTHER INFORMATION: UL131 cloning primer

<400> SEQUENCE: 10
gtacaattgt tggaaaaaat aattaatgcg tcagtctcgt atcattacgc tactagggat      60
aacagggtaa tcgattt                                                    77

<210> SEQ ID NO 11
<211> LENGTH: 32
<212> TYPE: DNA
<213> ORGANISM: Artificial Sequence
<220> FEATURE:
<223> OTHER INFORMATION: UL131 cloning primer

<400> SEQUENCE: 11
gcccaattgg ccagtgttac aaccaattaa cc                                   32

<210> SEQ ID NO 12
<211> LENGTH: 77
<212> TYPE: DNA
<213> ORGANISM: Artificial Sequence
<220> FEATURE:
<223> OTHER INFORMATION: gH cloning primer

<400> SEQUENCE: 12
gtactgcaga agaagagcc atatttgcat ttgaaacagg actgtgctct ctatagggat      60
aacagggtaa tcgattt                                                    77

<210> SEQ ID NO 13
<211> LENGTH: 32
<212> TYPE: DNA
<213> ORGANISM: Artificial Sequence
<220> FEATURE:
<223> OTHER INFORMATION: gH cloning primer

<400> SEQUENCE: 13
gccctgcagg ccagtgttac aaccaattaa cc                                   32

<210> SEQ ID NO 14
<211> LENGTH: 77
<212> TYPE: DNA
<213> ORGANISM: Artificial Sequence
<220> FEATURE:
<223> OTHER INFORMATION: gL cloning primer

<400> SEQUENCE: 14
gtacacgtgt gtagataatg tgtgccgcgc gtacgacctt cgatatctca cattagggat      60
aacagggtaa tcgattt                                                    77

<210> SEQ ID NO 15
<211> LENGTH: 32
<212> TYPE: DNA
<213> ORGANISM: Artificial Sequence
<220> FEATURE:
<223> OTHER INFORMATION: gL cloning primer

<400> SEQUENCE: 15
gcccacgtgg ccagtgttac aaccaattaa cc                                   32
```

```
<210> SEQ ID NO 16
<211> LENGTH: 71
<212> TYPE: DNA
<213> ORGANISM: Artificial Sequence
<220> FEATURE:
<223> OTHER INFORMATION: UL128 primer for red recombination

<400> SEQUENCE: 16
aaaaaatata ttatttttat gttatttttgt taaaaataat catcgaatac tataaaaatt    60
tttatggcgc g                                                         71

<210> SEQ ID NO 17
<211> LENGTH: 75
<212> TYPE: DNA
<213> ORGANISM: Artificial Sequence
<220> FEATURE:
<223> OTHER INFORMATION: UL128 primer for red recombination

<400> SEQUENCE: 17
gaagatacca aaatagtaaa gattttgcta ttcagtggac tggatgattc gaaaaattga    60
aaataaatac aaagg                                                     75

<210> SEQ ID NO 18
<211> LENGTH: 80
<212> TYPE: DNA
<213> ORGANISM: Artificial Sequence
<220> FEATURE:
<223> OTHER INFORMATION: UL131 primer for red recombination

<400> SEQUENCE: 18
ttgtactttg taatataatg atatatattt tcactttatc tcatttgatt tttatgaaaa    60
attgaaaata aatacaaagg                                                80

<210> SEQ ID NO 19
<211> LENGTH: 71
<212> TYPE: DNA
<213> ORGANISM: Artificial Sequence
<220> FEATURE:
<223> OTHER INFORMATION: UL131 primer for red recombination

<400> SEQUENCE: 19
attccgaaat ctgtacatca tgcagtggtt aaacaaaaac atttttattc tataaaaatt    60
tttatggcgc g                                                         71

<210> SEQ ID NO 20
<211> LENGTH: 71
<212> TYPE: DNA
<213> ORGANISM: Artificial Sequence
<220> FEATURE:
<223> OTHER INFORMATION: gH primer for red recombination

<400> SEQUENCE: 20
atatgaatat gatttcagat actatatttg ttcctgtaga taataactaa tataaaaatt    60
tttatggcgc g                                                         71

<210> SEQ ID NO 21
<211> LENGTH: 80
<212> TYPE: DNA
<213> ORGANISM: Artificial Sequence
<220> FEATURE:
<223> OTHER INFORMATION: gH primer for red recombination
```

<400> SEQUENCE: 21
gtggaaaatt tttcatctct aaaaaaagat gtggtcatta gagtttgatt tttatgaaaa    60
attgaaaata aatacaaagg                                                80

<210> SEQ ID NO 22
<211> LENGTH: 71
<212> TYPE: DNA
<213> ORGANISM: Artificial Sequence
<220> FEATURE:
<223> OTHER INFORMATION: UL130 primer for red recombination

<400> SEQUENCE: 22
ttggggaaat atgaacctga catgattaag attgctcttt cggtggctgg tataaaaatt    60
tttatggcgc g                                                         71

<210> SEQ ID NO 23
<211> LENGTH: 75
<212> TYPE: DNA
<213> ORGANISM: Artificial Sequence
<220> FEATURE:
<223> OTHER INFORMATION: UL130 primer for red recombination

<400> SEQUENCE: 23
tacgccaagc tatttaggtg acactataga atactcaagc ttggccggcc gaaaaattga    60
aaataaatac aaagg                                                     75

<210> SEQ ID NO 24
<211> LENGTH: 75
<212> TYPE: DNA
<213> ORGANISM: Artificial Sequence
<220> FEATURE:
<223> OTHER INFORMATION: gL primer for red recombination

<400> SEQUENCE: 24
caaagtggat gaattcccag atccggcctt gccggcctcg agggccggcc gaaaaattga    60
aaataaatac aaagg                                                     75

<210> SEQ ID NO 25
<211> LENGTH: 71
<212> TYPE: DNA
<213> ORGANISM: Artificial Sequence
<220> FEATURE:
<223> OTHER INFORMATION: gL primer for red recombination

<400> SEQUENCE: 25
acaaaattat gtattttgtt ctatcaacta cctataaaac tttccaaata tataaaaatt    60
tttatggcgc g                                                         71

<210> SEQ ID NO 26
<211> LENGTH: 15
<212> TYPE: PRT
<213> ORGANISM: Artificial Sequence
<220> FEATURE:
<223> OTHER INFORMATION: RhUL128 polyclonal antiserum

<400> SEQUENCE: 26

Cys Ile Asp Ser Asp Ser Tyr Pro Tyr Glu Glu Asp Ile Asp Gly
1               5                   10                  15

```
<210> SEQ ID NO 27
<211> LENGTH: 15
<212> TYPE: PRT
<213> ORGANISM: Artificial Sequence
<220> FEATURE:
<223> OTHER INFORMATION: RhUL130 polyclonal antiserum

<400> SEQUENCE: 27

Cys Thr Pro Arg Ser Ala Pro Ala Lys Gln Val Ala Pro Lys Pro
1               5                   10                  15

<210> SEQ ID NO 28
<211> LENGTH: 15
<212> TYPE: PRT
<213> ORGANISM: Artificial Sequence
<220> FEATURE:
<223> OTHER INFORMATION: RhUL131 polyclonal antiserum

<400> SEQUENCE: 28

Cys Val Arg Pro Gly Glu Ile Asp Glu Cys Leu Tyr Arg Gln Gln
1               5                   10                  15

<210> SEQ ID NO 29
<211> LENGTH: 14
<212> TYPE: PRT
<213> ORGANISM: Artificial Sequence
<220> FEATURE:
<223> OTHER INFORMATION: RhgL polyclonal antiserum

<400> SEQUENCE: 29

Cys Phe Thr Gly Glu Thr Phe Ser Pro Glu Asp Asp Ser Trp
1               5                   10

<210> SEQ ID NO 30
<211> LENGTH: 15
<212> TYPE: PRT
<213> ORGANISM: Artificial Sequence
<220> FEATURE:
<223> OTHER INFORMATION: RhgH polyclonal antiserum

<400> SEQUENCE: 30

His Asn Ser Thr Lys Cys Asn Asn Asn Gly Thr Arg Arg Asn Cys
1               5                   10                  15
```

UNITED STATES PATENT AND TRADEMARK OFFICE
CERTIFICATE OF CORRECTION

PATENT NO. : 10,376,575 B2
APPLICATION NO. : 15/919110
DATED : August 13, 2019
INVENTOR(S) : Don J. Diamond et al.

It is certified that error appears in the above-identified patent and that said Letters Patent is hereby corrected as shown below:

In the Specification

In the Statement of Government Interest section, Column 1, Lines 17-21, please delete:
"The present invention was made with government support under Grant No. AI063356, awarded by the National Institute of Allergy and Infectious Diseases; and Grant No. CA030206, awarded by the National Cancer Institute. The Government has certain rights in the invention."
And replace with:
--This invention was made with government support under AI063356, and CA030206 awarded by the National Institutes of Health. The government has certain rights in the invention.--

Signed and Sealed this
Fifth Day of September, 2023

Katherine Kelly Vidal
*Director of the United States Patent and Trademark Office*